(12) United States Patent
Miller et al.

(10) Patent No.: US 7,098,449 B1
(45) Date of Patent: Aug. 29, 2006

(54) SPECTROMETER CHIP ASSEMBLY

(75) Inventors: Raanan A. Miller, Newton, MA (US); William L. Robbins, Newton, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 276 days.

(21) Appl. No.: 10/836,432

(22) Filed: Apr. 30, 2004

Related U.S. Application Data

(63) Continuation-in-part of application No. 10/205,667, filed on Jul. 25, 2002, now abandoned, which is a continuation of application No. 09/882,883, filed on Jun. 15, 2001, now abandoned, and a continuation-in-part of application No. 10/321,822, filed on Dec. 16, 2002, now Pat. No. 6,806,463, which is a continuation-in-part of application No. 09/358,312, filed on Jul. 21, 1999, now Pat. No. 6,495,823, and a continuation-in-part of application No. 10/082,083, filed on Feb. 21, 2002, now Pat. No. 6,815,669, and a continuation-in-part of application No. 09/439,543, filed on Nov. 12, 1999, now Pat. No. 6,512,224.

(51) Int. Cl.
*H01J 49/40* (2006.01)

(52) U.S. Cl. ............. 250/287; 250/290; 250/281; 250/282

(58) Field of Classification Search ............. None
See application file for complete search history.

(56) References Cited

U.S. PATENT DOCUMENTS

| | | | |
|---|---|---|---|
| 2,615,135 A | 10/1952 | Glenn | |
| 3,511,986 A | 5/1970 | Llewellyn | |
| 3,621,240 A | 11/1971 | Cohen et al. | |
| 3,931,589 A | 1/1976 | Aisenberg et al. | |
| 4,025,818 A | 5/1977 | Giguere et al. | |
| 4,201,921 A | 5/1980 | McCorkle | |
| 5,420,424 A | 5/1995 | Carnahan et al. | |
| 5,455,417 A | 10/1995 | Sacristan | |
| 5,492,867 A | 2/1996 | Kotvas et al. | |
| 5,536,939 A | 7/1996 | Freidhoff et al. | |
| 5,541,408 A | 7/1996 | Sittler | |
| 5,654,544 A | 8/1997 | Dresch | |
| 5,723,861 A | 3/1998 | Carnahan et al. | |
| 5,763,876 A | 6/1998 | Perinarides et al. | |

(Continued)

FOREIGN PATENT DOCUMENTS

SU 966583 10/1982

(Continued)

OTHER PUBLICATIONS

"A Micromachined Field Driven Radio Frequency-Ion Mobility Spectrometer for Trace Level Chemical Detection," A Draper Laboratory Proposal Against the "Advanced Cross-Enterprise Technology Development for NASA Missions," Solicitation, NASA NRA 99-OSS-05.

(Continued)

*Primary Examiner*—Nikita Wells
*Assistant Examiner*—Zia R. Hashmi
(74) *Attorney, Agent, or Firm*—Fish & Neave IP Group Ropes & Gray LLP

(57) ABSTRACT

Method and apparatus for high field asymmetric waveform ion mobility spectrometry in an electronic chip assembly,, including an input section, an ion filter and detection section and a control section, in which ion filtering proceeds in a planar chamber under influence of high field asymmetric periodic signals, with detection integrated into the flow path, for producing accurate, real-time, data for identification of a broad range of chemical compounds.

38 Claims, 33 Drawing Sheets

U.S. PATENT DOCUMENTS

| | | | |
|---|---|---|---|
| 5,789,745 | A | 8/1998 | Martin et al. |
| 5,801,379 | A | 9/1998 | Kouznetsov |
| 5,834,771 | A | 11/1998 | Yoon et al. |
| 5,838,003 | A | 11/1998 | Bertsch et al. |
| 5,965,882 | A | 10/1999 | Megerle et al. |
| 5,998,788 | A | 12/1999 | Breit |
| 6,051,832 | A | 4/2000 | Bradshaw |
| 6,055,151 | A | 4/2000 | Tormey et al. |
| 6,066,848 | A | 5/2000 | Kassel et al. |
| 6,124,592 | A | 9/2000 | Spangler |
| 6,323,482 | B1 | 11/2001 | Clemmer et al. |
| 6,479,815 | B1 | 11/2002 | Goebel et al. |
| 6,495,823 | B1 | 12/2002 | Miller et al. |
| 6,504,149 | B1 | 1/2003 | Guevremont et al. |
| 6,512,224 | B1 | 1/2003 | Miller et al. |
| 6,621,077 | B1 | 9/2003 | Guevremont et al. |
| 6,639,212 | B1 | 10/2003 | Guevremont |
| 6,653,627 | B1 | 11/2003 | Guevremont |
| 6,690,004 | B1 | 2/2004 | Miller et al. |
| 6,703,609 | B1 | 3/2004 | Guevremont |
| 6,713,758 | B1 | 3/2004 | Guevremont |
| 6,753,522 | B1 | 6/2004 | Guevremont |
| 6,770,875 | B1 | 8/2004 | Guevremont |
| 6,774,360 | B1 | 8/2004 | Guevremont |
| 6,787,765 | B1 | 9/2004 | Guevremont |
| 6,799,355 | B1 | 10/2004 | Guevremont |
| 6,806,466 | B1 | 10/2004 | Guevremont |
| 2001/0030285 | A1 | 10/2001 | Miller et al. |
| 2002/0070338 | A1 | 6/2002 | Loboda |
| 2002/0134932 | A1 | 9/2002 | Guevremont et al. |
| 2003/0020012 | A1 | 1/2003 | Guevremont et al. |
| 2003/0038235 | A1 | 2/2003 | Guevremont et al. |
| 2003/0052263 | A1 | 3/2003 | Kaufman et al. |
| 2003/0089847 | A1 | 5/2003 | Guevremont et al. |
| 2003/0132380 | A1 | 7/2003 | Miller et al. |
| 2004/0094704 | A1 | 5/2004 | Miller et al. |

FOREIGN PATENT DOCUMENTS

| | | |
|---|---|---|
| SU | 1337934 A2 | 9/1987 |
| SU | 1627984 A2 | 7/1988 |
| SU | 1412447 A1 | 6/1998 |
| SU | 1485808 | 10/1998 |
| WO | WO 00/08454 | 2/2000 |
| WO | WO 00/08455 | 2/2000 |
| WO | WO 00/08456 | 2/2000 |
| WO | WO 00/08457 | 2/2000 |
| WO | WO 01/08197 A1 | 2/2001 |
| WO | WO 01/22049 A2 | 3/2001 |
| WO | WO 01/35441 A1 | 5/2001 |
| WO | WO 01/69217 A2 | 9/2001 |
| WO | WO 01/69220 A2 | 9/2001 |
| WO | WO 01/69647 A2 | 9/2001 |
| WO | WO 02/071053 A | 9/2002 |
| WO | WO 02/083276 A1 | 10/2002 |
| WO | WO 03/005016 A1 | 1/2003 |
| WO | WO 03/015120 A1 | 2/2003 |

OTHER PUBLICATIONS

Barnett, D.A. et al., "Isotope Separation Using High-Field Asymmetric Waveform Ion Mobility Spectrometry," Nuclear Instruments & Methods in Physics Research (2000), pp. 179-185, 450(1).

Buryakov, I.A. et al., "Separation Ions According to Mobility in a Strong ac electric Field," Sov. Tech. Phs. Lett. (1991), pp. 446-447, 17(6).

Buryakov, I.A. et al., Device and Method For Gas Electrophoresis, Chemical Analysis fo Environment, edit. Prof. V.V. Malakhov, Novosibirsk; Nauka (1991), pp. 113-127.

Buryakov, I.A. et al., "A New Method of Separation of Multi-Atomic Ions by Mobility at Atmospheric Pressure Using a High-Frequency Amplitude-Asymmetric Strong Electric Field," International Journal of Mass Spectometry and Ion Processes (1993), pp. 143-148, 128.

Carnahan, B. et al., "Field Ion Spectrometry—A New Analytical Technology for Trace Gas Analysis," ISA, (1996), pp. 87-96, 51(1).

Carnahan, B. et al., "Field Ion Spectrometry—A New Technology for Cocaine and Heroin Detection," SPIE, (1997), pp. 106-119, 2937.

Eiceman, G.A., et al., "Miniature radio-frequency mobility analyzer as a gas chromatographic detector for oxygen-containing volatile organic compounds, pheromones, and other insect attractants," J. Chromatography, (2001), pp. 205-217, 917.

Guevremont, R. and Purves, R., "High Field Asymmetric Waveform Ion Mobility Spectometry-Mass Spectrometry: An Investigation of Leucine Enkephalin Ions Produced by Electrospray Ionization," J. Am. Soc. Mass. Spectrom, (1999), pp. 492-501, 10.

Guevremont, R. et al., "Calculation of Ion Mobilities From Electrospray Ionization High Field Asymmetric Waveform Ion Mobility Spectrometry Mass Spectrometry," Journal of Chemical Physics, (2001), pp. 10270-10277, 114(23).

Guevremont, R. et al., "Atmospheric Pressure In Focusing in a High-Field Asymmetric Waveform Ion Mobility Spectrometer," Review of Scientific Instruments, (1999), pp. 1370-1383, 70(2).

Handy, Russell et al., "Determination of nanomlar levels of perchlorate in water by ESI-FAIMS-MS," JAAS (2000), pp. 907-911, 15.

Krylov, E.V., "A Method of Reducing Diffusion Losses in a Drift Spectrometer," Technical Physics, (1999), pp. 113-116, 4d(1).

Krylov, E.V., "Pulses of Special Shapes Formed on a Capacitive Load," Instruments and Experimental Techniques, (1997), pp. 628, 40(5).

Miller, R.A. et al., "A MEMS Radio-Frequency Ion Mobility Spectrometer for Chemical Agent Detection," (Jun. 2000) Proceedings of the 2000 Solid State Sensors and Actuators Workshop, Hilton Head, SC.

Miller, R.A. et al., "A MEMS radio-frequency ion mobility spectrometer for chemical vapor detection," Sensors and Actuators, (2001), pp. 301-312, A91.

Miller, R.A. et al., "A Novel Micromachined High-Field Asymmetric Waveform-Ion Mobility Spectrometer," Sensors and Actuators B, (2000) pp. 300-306, B67 (3).

Pilzecker, P. et al., "On-Site Investigations of Gas Insulated Substations Using Ion Mobility Spectrometry for Remote Sensing of SF6 Decomposition," IEEE, (2000), pp. 400-403.

Riegner, D.E. et al., "Qualitative Evaluation of Field Ion Spectrometry for Chemical Warfare Agent Detection," Proceedings of the ASMS Conference on Mass Spectrometry and Allied Topics (Jun. 1997), pp. 473A-473B.

Schneider, A. et al., High Sensitivity GC-FIS for Simultaneous Detection of Chemical Warfare Agents, Mine Safety Appliances Co., Pittsburgh, PA, USA, (2000), AT-Process, pp. 124-136, 5(3,4), CODEN: APJCFR ISSN: 1077-419X.

Krylov, E.V., "Comparison of the Planar and Coaxial Field Asymmetrical Waveform Ion Mobility Spectrometer (FAIMS)," International Journal of Mass Spectrometry, 225, (2003) pp. 39-51.

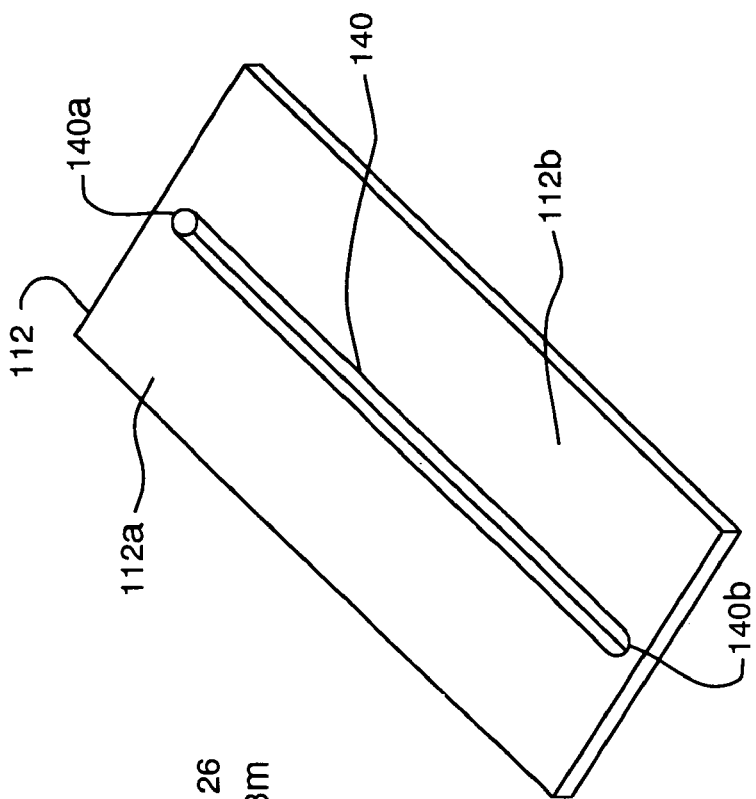
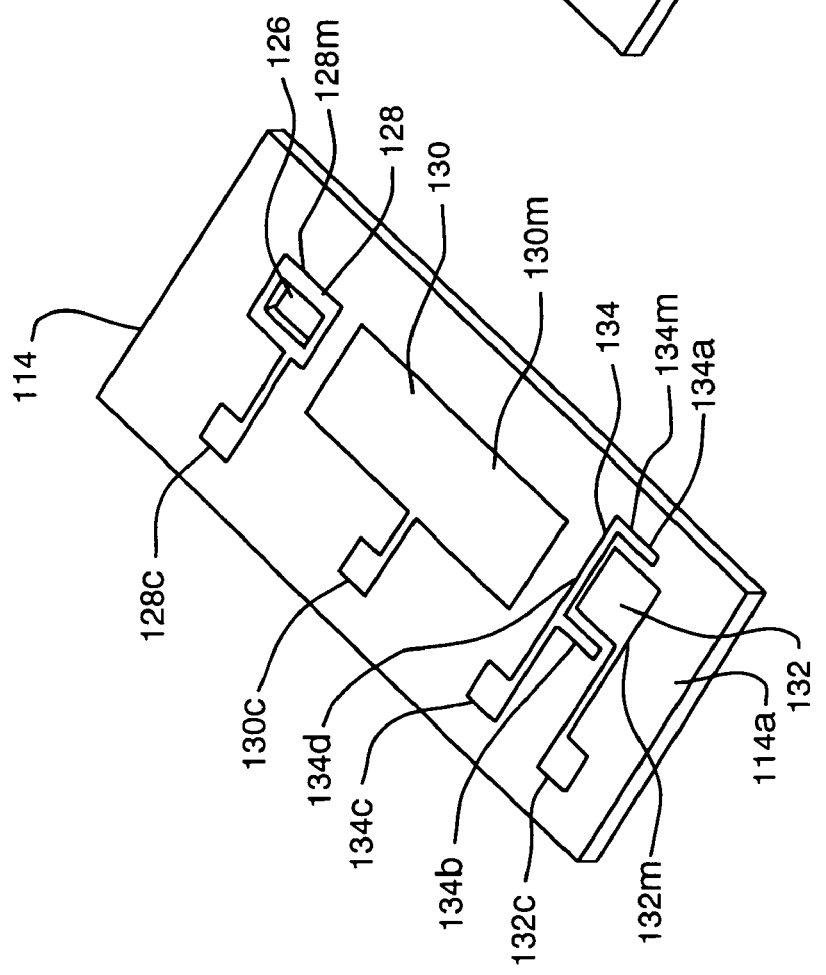
FIG. 8(d)
FIG. 8(c)

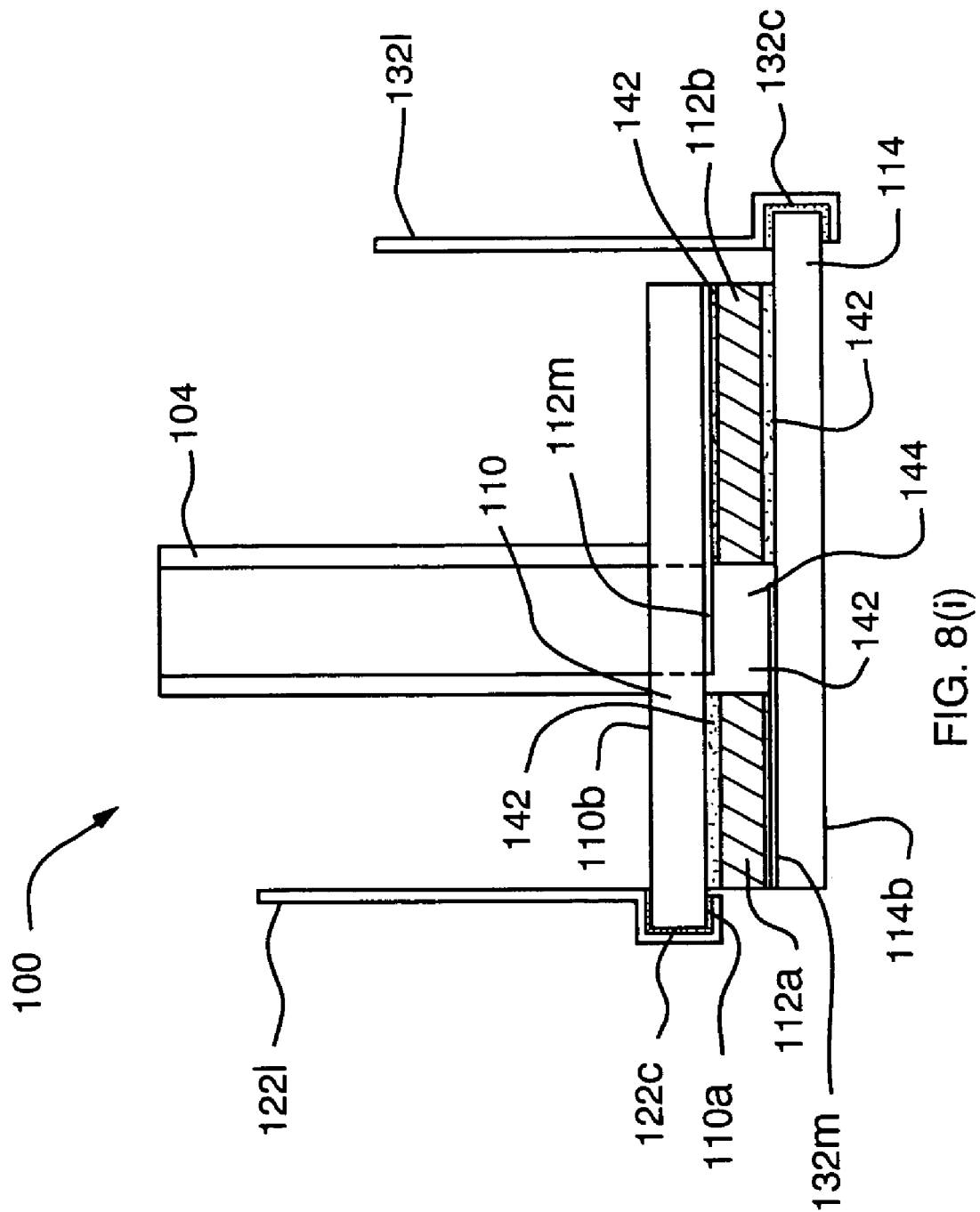

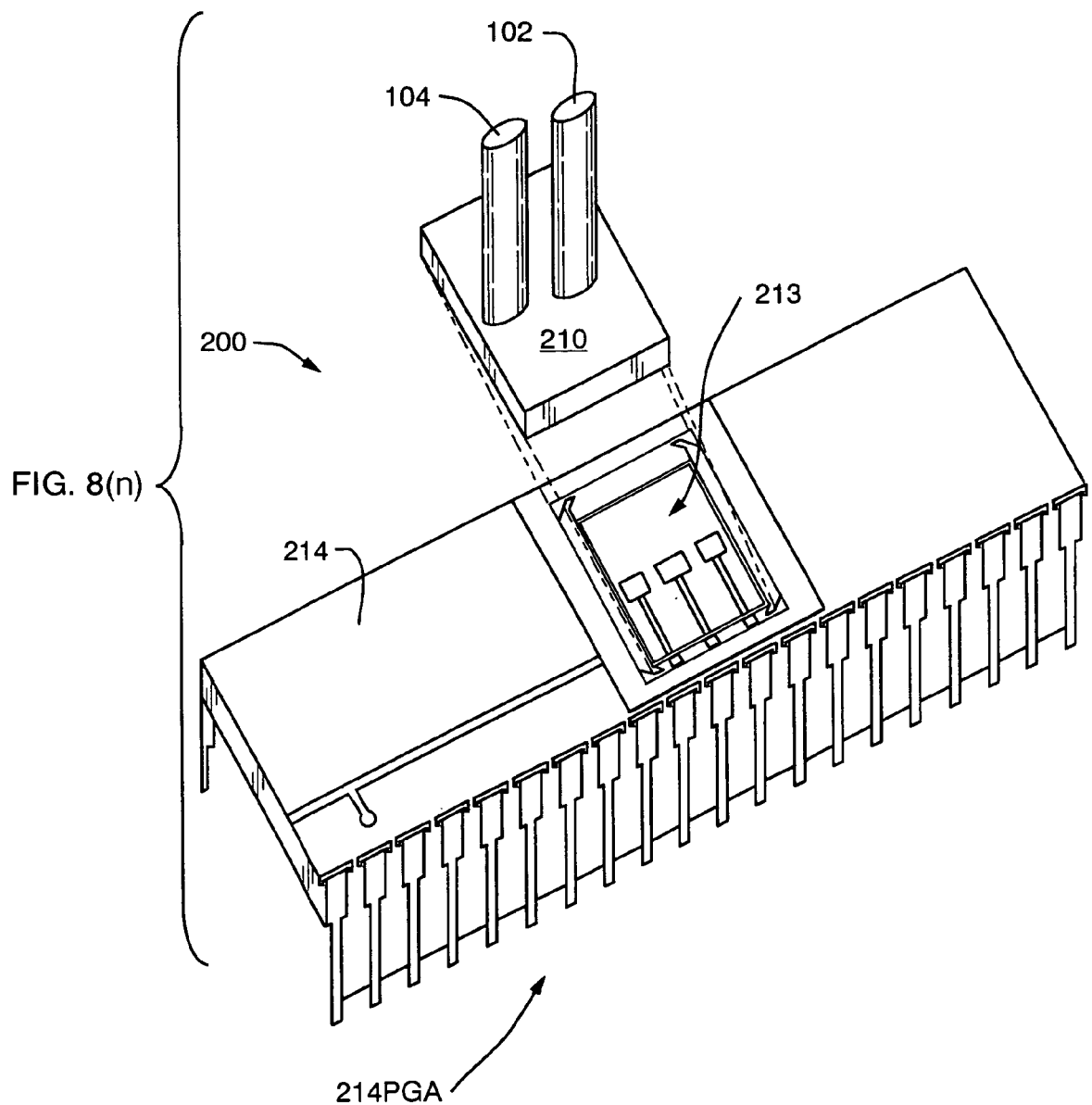

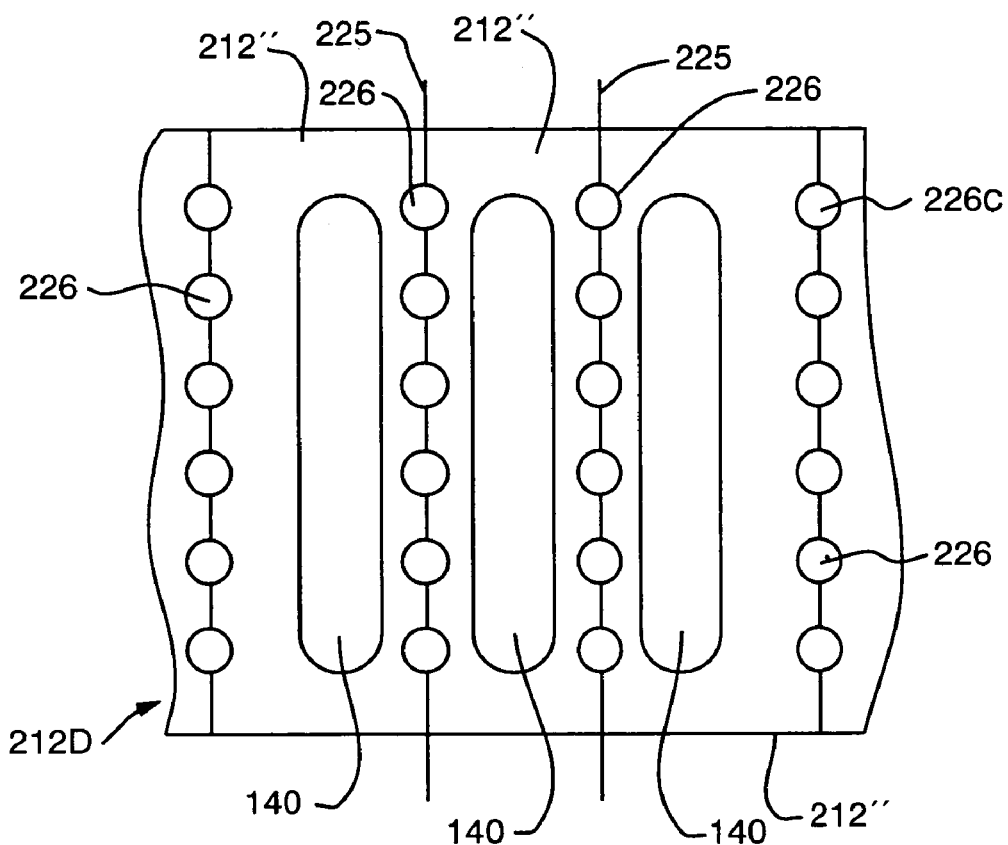
FIG. 8(s) (1)
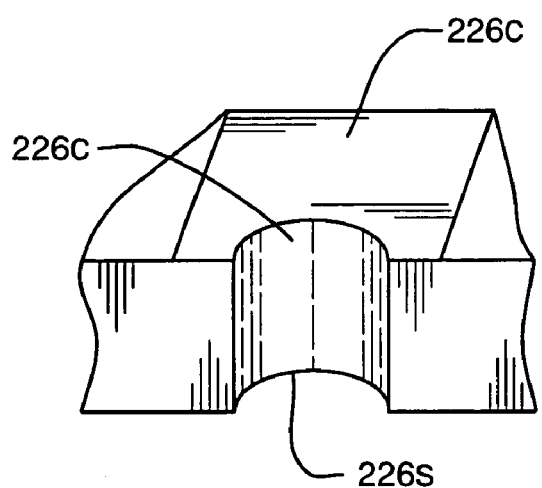
FIG. 8(s) (2)

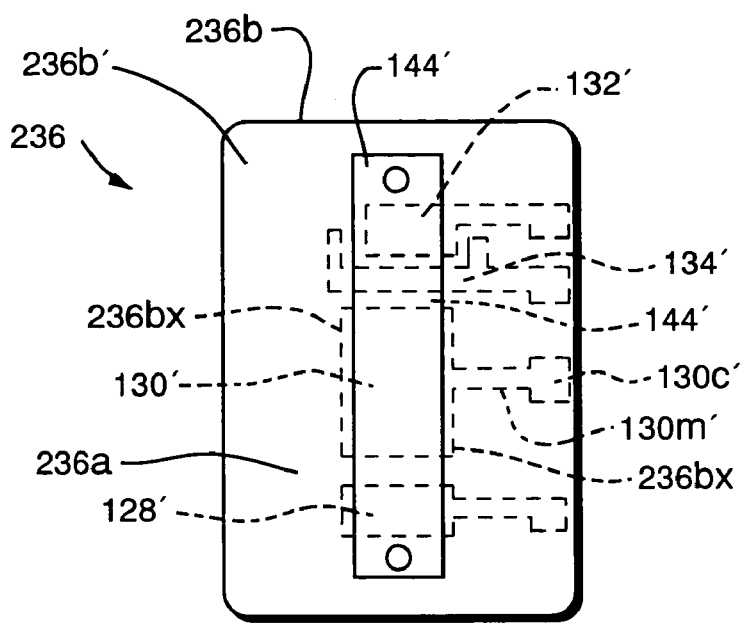
FIG. 8(t)(1)
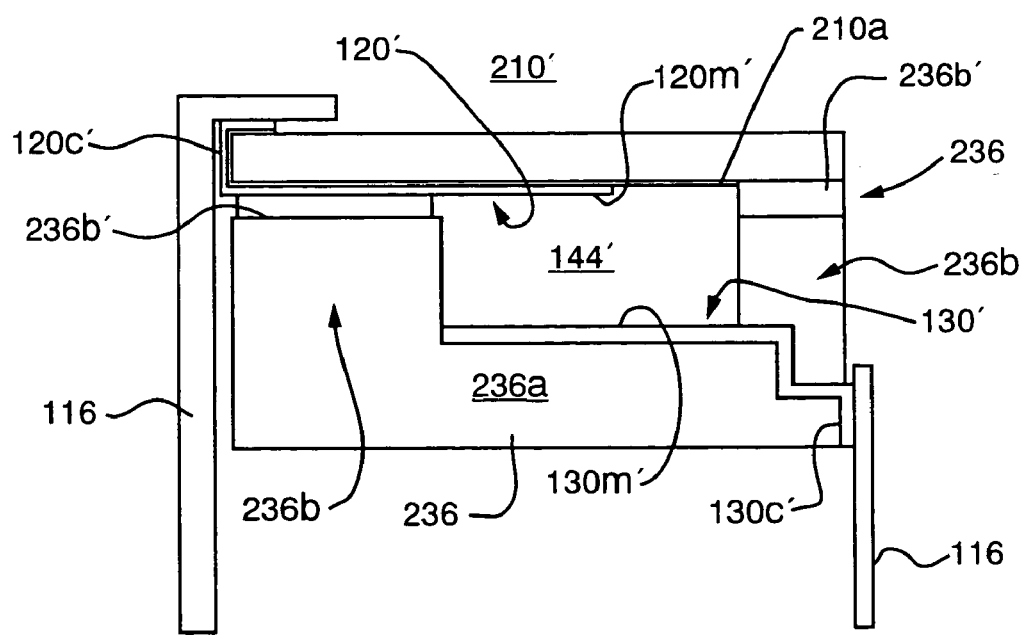
FIG. 8(t)(2)

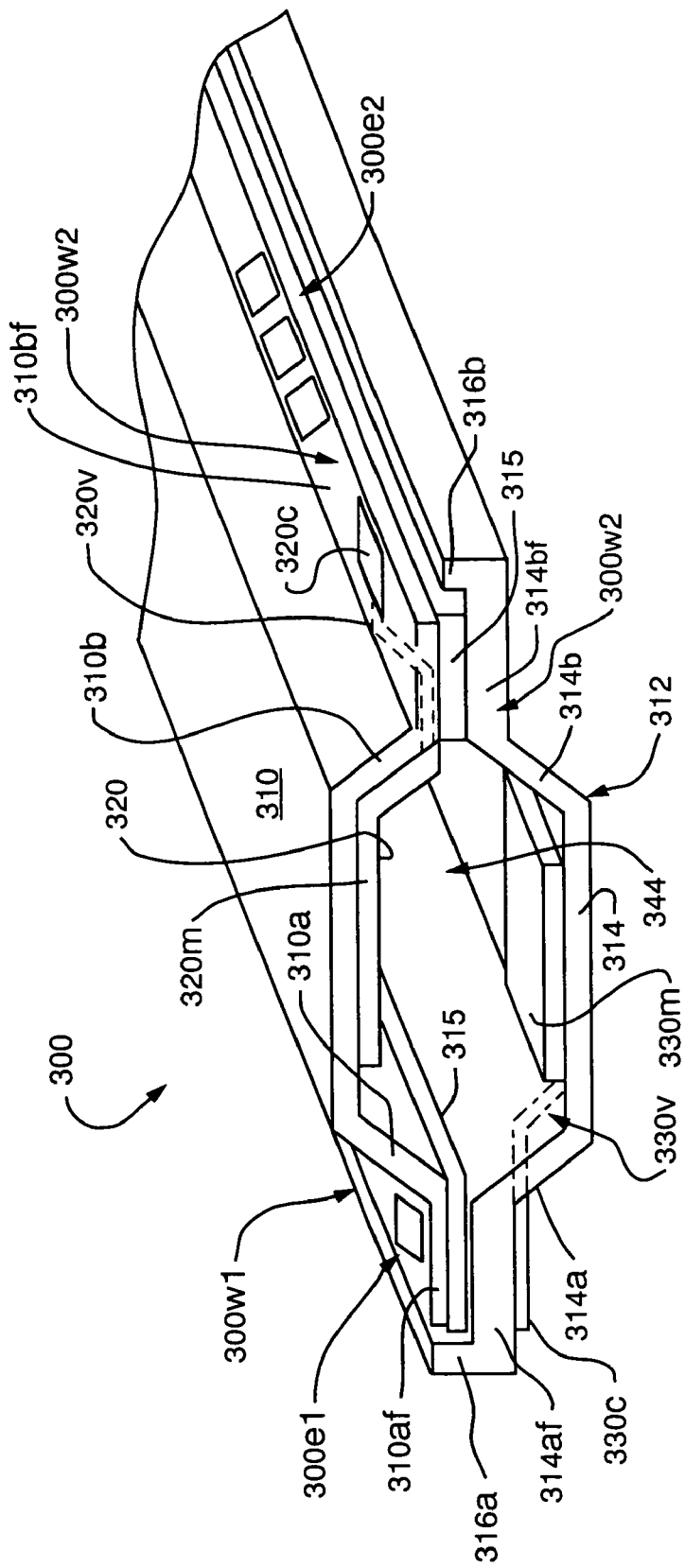
FIG. 8(t)(3)

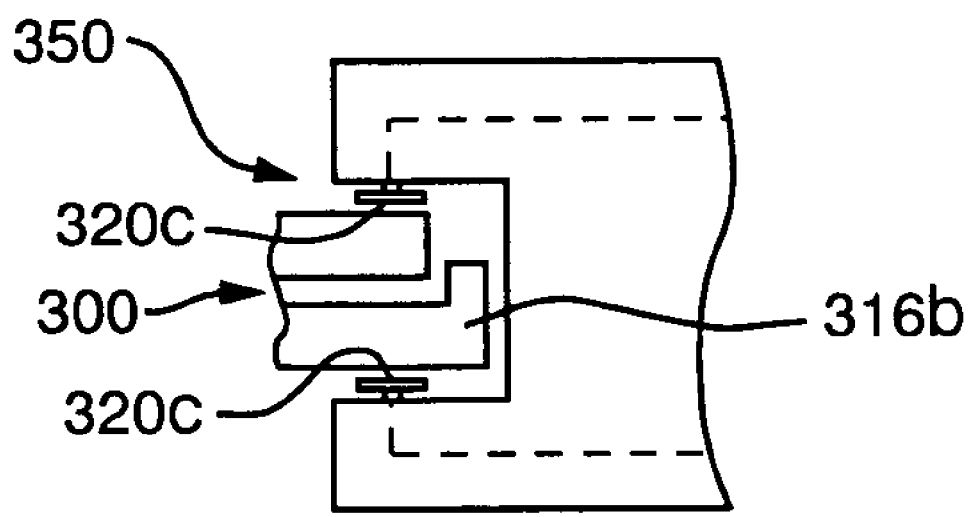
FIG. 8(t)(4)

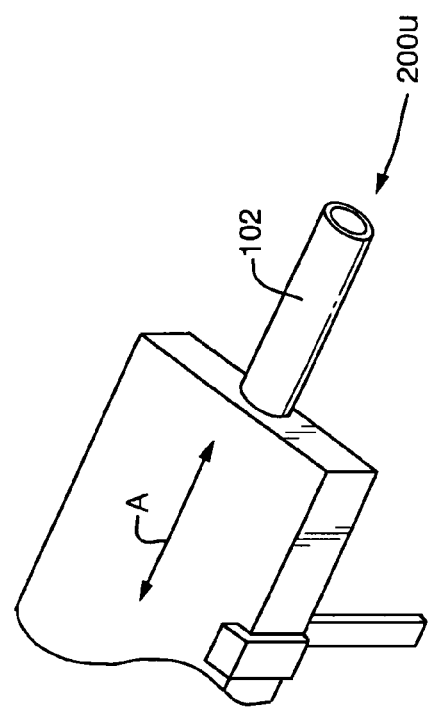
FIG. 8(u)(1)
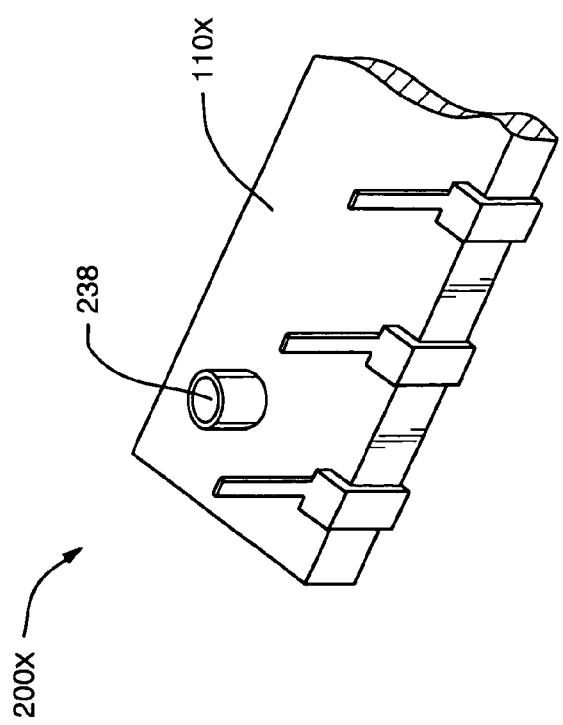
FIG. 8(v)

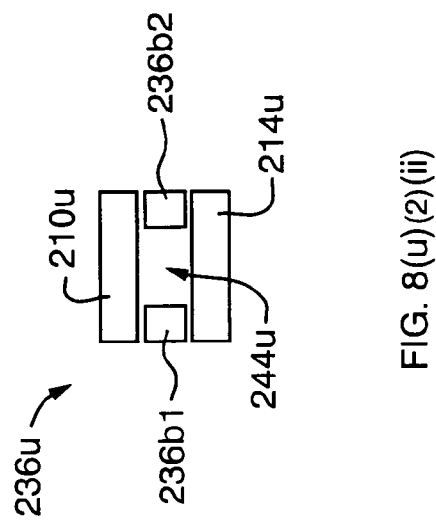
FIG. 8(u)(2)(ii)
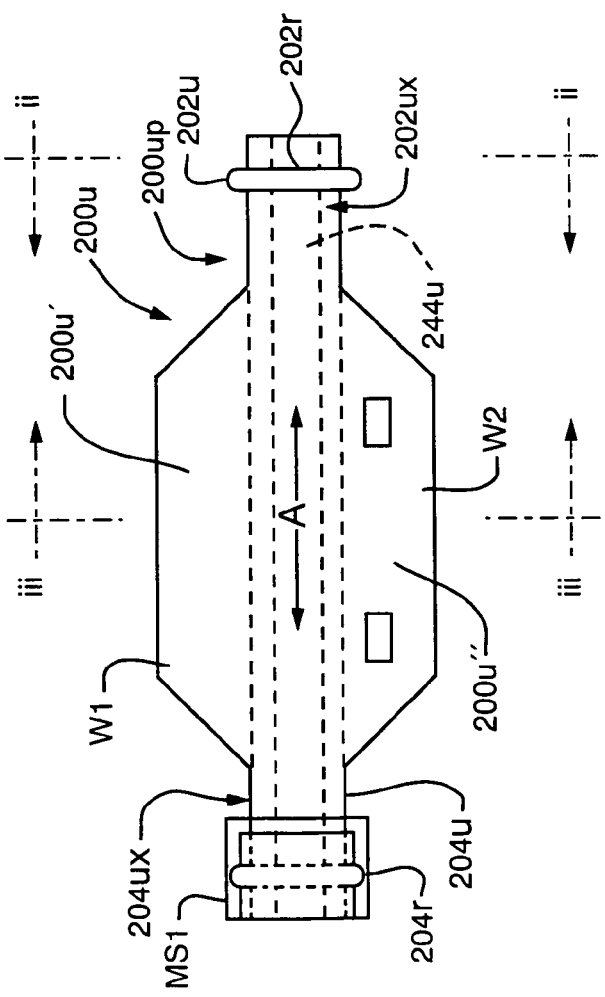
FIG. 8(u)(2)(i)

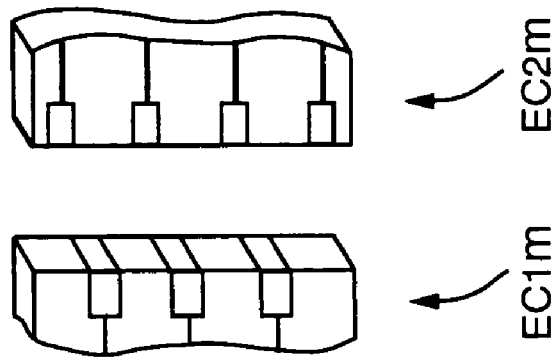
FIG. 8(u)(2)(iv)
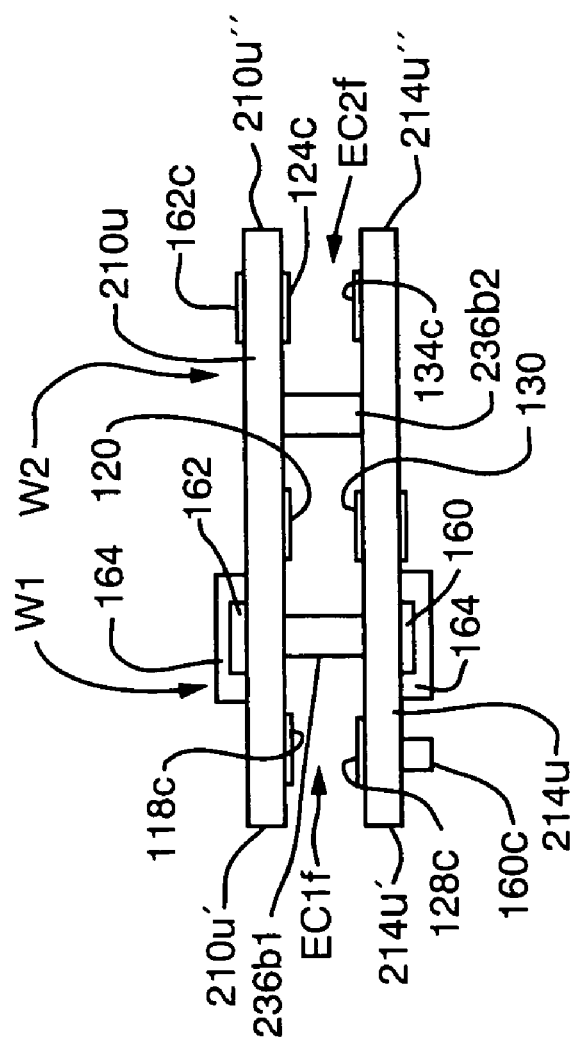
FIG. 8(u)(2)(iii)

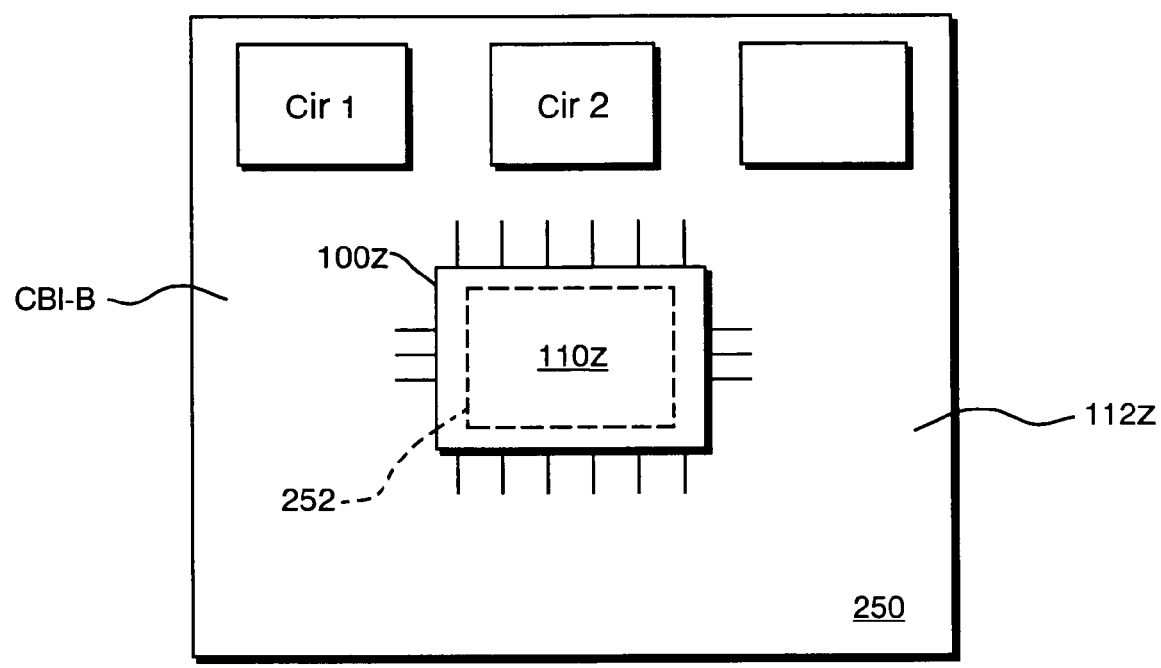
FIG. 8(z)(1)
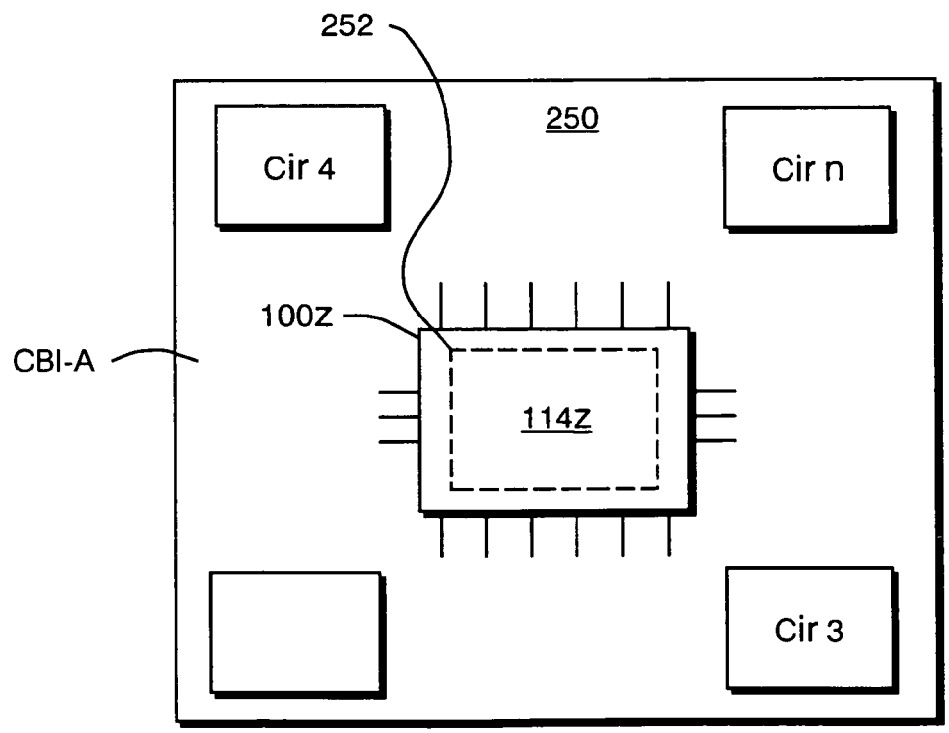
FIG. 8(z)(2)

SPECTROMETER CHIP ASSEMBLY

RELATED APPLICATION(S)

This application is a Continuation-in-Part of U.S. application Ser. No. 10/205,667, filed Jul. 25, 2002 now abandoned, which is a continuation of U.S. application Ser. No. 09/882,883, filed Jun. 15, 2001 now abandoned. This application is also a continuation-in-part of U.S. application Ser. No. 10/321,822, filed Dec. 16, 2002 now U.S. Pat. No. 6,806,463, which is a continuation-in-part of U.S. application Ser. No. 09/358,312, filed Jul. 21, 1999, the latter now issued as U.S. Pat. No. 6,495,823. This application is also a continuation-in-part of U.S. application Ser. No. 10/082,803, filed Feb. 21, 2002 now U.S. Pat. No. 6,815,669, which is a continuation-in-part of U.S. application Ser. No. 09/358,312, filed Jul. 21, 1999 now U.S. Pat. No. 6,495,823 and a continuation-in-part of U.S. application Ser. No. 09/439,543, filed Nov. 12, 1999, the latter now issued as U.S. Pat. No. 6,512,224. The contents of all of these patent applications are incorporated herein by reference.

BACKGROUND OF THE INVENTION

The present invention relates to spectrometry, and more particularly, to planar spectrometer devices that enable analysis of compounds by high field asymmetric waveform ion mobility techniques, and method of achieving same.

A chemical sensor system provides samples to a detector, i.e., a spectrometer, for identification. The device may take samples directly from the environment, or it may incorporate a front end device to separate compounds in a sample before detection.

In making such measurements, whether in the lab, the workplace or in the field, there is a need for unambiguous compound identification. One approach is to employ a combination of instruments capable of providing an orthogonal set of information for each chemical measurement. (The term orthogonal will be appreciated by those skilled in the art to mean data which enables accurate identification of a particular chemical species, and uses a different property of the compound for identification.)

One combination of known instruments is a gas chromatograph (GC) attached to a mass spectrometer (MS). The GC separates compounds in a gas sample that improves the chemical identification capability of the spectrometer. The mass spectrometer is generally considered one of the most accurate detectors for compound identification. A mass spectrometer can generate a fingerprint pattern of fragment ions based on mass corresponding to each compound eluting from the GC. Use of the mass spectrometer as the GC detector dramatically increases the value of analytical separation provided by the GC. The combined GC-MS information, in most cases, is sufficient for unambiguous identification of the compound.

Mass spectrometers are expensive, easily exceeding $100 K, and are difficult to deploy in the field. Mass spectrometers also suffer from the need to operate at low pressures resulting in complex systems, and their spectra can be difficult to interpret often requiring a highly trained operator. As well, the GC-MS is not well suited for small, low cost, fieldable instruments.

Lower cost and compact, reliable instrumentation for the laboratory and field is a desirable goal. In the lab, there is a continuing demand for improvements in affordable bench top analytical equipment. As well, there is a developing interest in making in situ measurements of chemicals present in complex mixtures at industrial and environmental venues. Therefore the search continues for low cost, high quality, and compact chemical detector equipment.

Time-of-flight Ion Mobility Spectrometers (TOF-IMS) have been described as functional detectors from early in the development of ion mobility spectrometry. High-speed response and low memory effects have been attained, and the gas phase ion chemistry inside the TOF-IMS can be highly reproducible providing the foundation to glean chemical class information from mobility spectra. Widespread use still remains a problem for TOF-IMS. Despite advances over the past decade, TOF-IMS flow channels (also referred to as drift tubes) are still comparatively large and expensive and suffer from losses in detection limits when made small.

The high field asymmetric waveform ion mobility spectrometer (FAIMS) is an alternative to the TOF-IMS. In a FAIMS device, a gas sample that contains a chemical compound is subjected to an ionization source. Ions from the ionized gas sample are drawn into an ion filter and subjected to a high field asymmetric waveform ion mobility filtering technique. Select ion species allowed through the filter are then passed to an ion detector, enabling indication of a selected species.

The FAIMS filtering technique involves passing ions in a carrier gas through strong electric fields between the filter electrodes. The fields are created by application of an asymmetric period voltage (typically along with a further control bias) to the filter electrodes.

The process achieves a filtering effect by accentuating differences in ion mobility. The asymmetric field alternates between a high and low field strength condition that causes the ions to move in response to the field according to their mobility. Typically the mobility in the high field differs from that of the low field. That mobility difference produces a net displacement of the ions as they travel in the gas flow through the filter. In absence of a compensating DC bias signal, the ions will hit one of the filter electrodes and will be neutralized. In the presence of a specific DC bias signal, a particular ion species will be returned toward the center of the flow path and will pass through the filter without neutralization. The amount of change in mobility in response to the asymmetric field is compound-dependent. This permits separation of ions from each other according to their species, in the presence of an appropriately set DC bias.

In the past, Mine Safety Appliances Co. (MSA) made an attempt at a functional FAIMS implementation in a cylindrical device with coaxial electrodes, such as disclosed in U.S. Pat. No. 5,420,424. (This FAIMS technology is referred to by MSA as Field Ion Spectrometry (FIS), see FIG. 1.) The device has been found to be complex, with many parts, and somewhat limited in utility.

A characteristic of known coaxial FAIMS devices is the relatively slow detection time. This can be a serious problem when coupling to a prefilter or separator, such as a GC. A GC operates so rapidly that known FAIMS devices cannot generate a complete spectra of the ions present under each GC peak. Therefore these prior art FAIMS devices would have to be limited to a single compound detection mode if coupled to a GC, with a response time of about 10 seconds. Any additional compound that is desired to be measured will take approximately an additional 10 seconds to measure. A FAIMS device with faster response times is much desired.

While the foregoing arrangements are adequate for a number of applications, it is still desirable to have a low cost and compact spectrometer that can render real-time or near real-time indications of detected chemical compounds, whether for the laboratory, the battlefield or in other environments, and whether as a stand alone detector or in cooperation with other devices such as a GC or an MS.

It is therefore an object of the present invention to provide a functional, small, spectrometer that overcomes the limitations of the prior art.

It is a further object of the present invention to provide a chemical sensor that features the benefits of FAIMS but is able to operate rapidly, affording real-time or near real-time detection.

It is a further object of the present invention to provide a chemical sensor that features the benefits of FAIMS and is able to detect multiple species simultaneously.

It is a further object of the present invention to provide a chemical sensor that features the benefits of FAIMS but is able to detect positive and negative ions simultaneously.

It is a further object of the present invention to provide a chemical sensor that features the benefits of FAIMS but is able to be part of a system that generates orthogonal data that fully identifies a detected species.

It is a further object of the present invention to enable a new class of chemical sensors that can rapidly produce unambiguous, real-time or near real-time, in-situ, orthogonal data for identification of a wide range of chemical compounds.

It is a further object of the present invention to provide a class of sensors that enable use of pattern recognition algorithms to extract species information.

It is a further object of the present invention to provide a class of sensors that do not require consumables for ionization.

It is a further object of the present invention to provide a class of sensors utilizing an arrays of FAIMS devices each tuned to detect a particular compound, such that multiple compounds can be detected rapidly, with simplified electronics.

It is a further object of the present invention to provide a class of sensors utilizing arrays of FAIMS devices to provide redundancy in ion detection.

It is a further object of the present invention to provide a class of sensors utilizing arrays of FAIMS devices where each ion filter has its own flow path (or flow channel) and is doped with a different dopant for better compound identification.

It is a further object of the present invention to provide a class of detectors that can provide information on the cluster state of ions and ion kinetics by varying the amplitude of the high voltage asymmetric electric field.

It is a further object of the present invention to provide a class of detectors that can provide information on the cluster state of ions and ion kinetics by adjusting the frequency of the asymmetric signal.

It is a further object of the present invention to provide a class of detectors that can provide information on the cluster state of ions and ion kinetics by adjusting the flow rate of ions through the device.

It is a further object of the present invention to provide a class of detectors that can provide information on the cluster state of ions and ion kinetics by varying the amplitude of the high voltage asymmetric electric field, or by adjusting the frequency of the asymmetric signal, or by adjusting the flow rate of ions through the device, or any combination of these techniques.

It is further an object of this invention to provide a class of sensors that can quantitatively detect samples over a wide range of concentrations through controlled dilution by regulating the amount of ions injected into the ion filter region by controlling the potentials on deflector electrodes.

SUMMARY OF THE INVENTION

Embodiments of the invention define spectrometer improvements in several variations, such as the following illustrative embodiments:

Preferably, a high field asymmetric waveform ion mobility spectrometer system for chemical analysis of compounds in a compound-carrying sample includes at least a pair of electrode-carrying surfaces facing each other across a gap, the gap defined in large part by a spacer part, the surfaces and the spacer part cooperating to form a flow channel, an ion filter formed on the surfaces in the flow channel, the filter including at least one pair of filter electrodes facing each other across the gap, with ions from an ion region flowing in the flow channel and having a flow path passing between the filter electrodes, the filter electrodes applying asymmetric mobility-controlling fields across the gap, the filter filtering the ions according to their mobility in the fields, ions with selected mobility passing though the filter, and electrical control part configured to apply a compensated asymmetric periodic voltage to the ion filter electrodes for generating the fields. Preferably the flow channel is hermetically sealed.

The system may include wherein the electrode-carrying surfaces are insulated and the flow channel is hermetically sealed, or wherein the flow channel extends from the ion region to an output part, the electrode-carrying surfaces presenting an essentially planar flow path for travel of the sample in the flow channel between the ion region to the output part, or further comprising substrates, the electrode-carrying surfaces being formed on the substrates.

The system may include wherein the flow channel extends along a longitudinal drift axis and is non-conducting, the flow channel having a plurality of conducting electrodes located thereon spaced from each other along the axis, or wherein the substrate has insulating surfaces that define an electrically insulated flow channel between the input part and the output part, the output part further comprising an ion detector region, or wherein the output part further includes a detector for detecting ions in the flow channel.

The system may include wherein the output part further includes at least a pair of electrodes disposed in the flow channel, one electrode formed on each substrate facing each other, for interaction with the selected ions passing though the filter into the output part, wherein the output part further comprises detector electrodes, or wherein the control part is further configured to enable simultaneous independent detection by the detector electrodes of different species of the selected ions passing though the filter.

The control part may include contact pads on the substrates for applying signals to the electrodes, and the output part further includes an array of ion detectors. The output part further may include a segmented detector, the detector formed by a plurality of electrodes placed along the flow channel one after the other in the output part.

The system may further comprise an array of ion filters, at least one filter electrode formed on each substrate. A separate flow channel is associated with each filter of the array, for passing ions in each flow channel to the output part for simultaneous detection of ion species.

The system further may include a source of ionized gas at the input part, a pump coupled to the substrate and communicating with the flow channel for flow of the ionized gas from the source to the output part, possibly further having a recirculation pump coupled one of the substrates and communicating with the flow channel for recirculating the gas in the flow channel, and further optional having a heater in the gas flow, the heater heating the flow channel and purging neutralized ions.

In a preferred embodiment, the substrates and a spacer have planar surfaces and extend to define a device housing for the flow channel. The substrates are discrete ceramic plates separate by a discrete a spacer, mated with a bonding material to form the flow channel.

Embodiments of the invention may further include an ion source for input of ions into the flow channel, the substrates forming an insulated housing along the drift axis, the housing holding the ion source, ion filter, control part and output part in fixed relationship to the flow channel axis.

The control part may further include an electrical connection for connection of the electrodes to an amplifier under direction of a microcomputer. The control part may include a controller circuit defined within the housing for controlling the ion filtering. The control part may operate to apply a bias voltage to provide the compensation of the compensated asymmetric periodic voltage across the ion filter electrodes for controlling the paths of the ions through the filter. The control part may further comprises a drive circuit for selectively adjusting the duty cycle to provides the compensation of the compensated asymmetric periodic voltage to target the selected ion passed by the filter.

Embodiments may further describe at least a pair of substrates for forming the electrode-carrying surfaces facing each other across a gap, the substrates mated together and forming an electronic spectrometer chip assembly. Preferably, a high field asymmetric waveform ion mobility system includes an input part and an output part, a pair of insulative substrates defining between them a flow channel a pair of ion filter electrodes disposed opposite each other in the flow channel, at least one electrode associated with each substrate, an electronic controller configured to apply a compensated asymmetric periodic voltage to the ion filter electrodes for controlling the path of ions in the flow channel, and the insulative substrates electrically insulating the filter electrodes from the output part, ions in the flow channel passing from the filter electrodes to the output part under influence of the applied asymmetric voltage controlled of the controller.

The insulated surfaces may form an insulated flow channel that are not held at a bias level. The substrates are planar and the insulated flow channel electrically insulates the filter electrodes from the output part. A detector is defined in the output part downstream from the filter for detecting the selected ions passing through the filter. The detector includes detector electrodes that are independent of each other and the controller further comprises electrical leads for simultaneously outputting signals representing the specific ion species detected on each of the detector electrodes.

In various embodiments, the trajectory of an ion passing through the filter is regulated by the electronic controller. With a segmented detector, downstream from the ion filter, it has segments that are separated along the flow channel longitudinal axis to detect ions spatially according to their trajectories. The device may have an array of electrodes, the electrodes being in the flow channel and under the control of the control part. The output part may further have a detection part, further with an ion source in the ion region for ionizing compounds in the sample and delivering ions from the sample in the flow channel, the ions being filtered by the filter electrodes in the flow channel and passing to the detection part for detection.

Preferably, in an embodiment of the invention, a high field asymmetric waveform ion mobility system defines an ion input part and a spectrometer part. The spectrometer part has an ion filter part, an isolation part, and an output part, ions being delivered to the ion filter part by the input part. The isolation part facilitates non-conductive connection of the filter part and the output part. A flow channel extends from the filter part through the isolation part to the output part. A controller part applies electrical potentials to the filter part, these electrical potentials including a compensated asymmetric periodic voltage for generating a control field. The spectrometer part further defining planar substrate surfaces opposite each other and each carrying an opposing electrode, the ion filter part including the opposing electrodes across from each other in the flow channel, the flow channel defining a first flow channel region for application of the control field to ions in the filter part. The ion filter part is located in the first flow channel region, the flow channel also defining a second flow channel region. The isolation part is located in the second flow channel region after the first region and before the output part. The ion filter part passes ions in the flow channel under influence of the control field, and ions that are passed by the filter part travel through the isolation part to the output part for detection. The isolation part isolates the control field from the output part. Preferably the device has a pair of substrates defining the flow channel. Electrodes are provided on the substrates that are electrically insulated and the substrates are electrically insulating. Preferably the substrates are essentially planar along the flow channel.

Preferably in another embodiment, a high field asymmetric waveform ion mobility system includes an input part and a detector part, at least pair of planar substrates defining between them a flow channel for the flow of ions, a plurality of electrodes, including a pair of ion filter electrodes opposite each other and disposed in the flow channel between the input part and detector part, one filter electrode associated with each substrate, the input configured for receiving samples included of a variety of ion species, an electronics part configured to apply controlling electric signals to the ion filter electrodes, the signals including a compensated asymmetric periodic voltage, the filter electrodes cooperating with the applied signals and the flow channel for simultaneously passing a selected plurality of ion species to the detector part from the sample, the detector part enabling simultaneous detection of the selected plurality of ion species passed by the filter; and the electronics part providing separate independent outputs at the detector part, the outputs providing signals representative of species detected simultaneously from within these samples. Preferably the detector part is formed with at least a pair of detector electrodes disposed in the flow channel. At least one detector electrode is formed on each substrate. The detector electrodes carrying signals to independent outputs representative of detected ion species. One detector electrode is held at a first bias level and the second detector electrode is held at a second bias level for simultaneous detection of different ion species passed by the filter.

Preferably in another embodiment, a high field asymmetric waveform ion mobility detection system includes an input part and an output part, at least pair of planar substrates defining between them a flow channel for the flow of ions from the input part to the output part, a plurality of electrodes opposite each other and defined in the flow channel to form an arrangement of electrodes, the plurality defining at least one filter electrode associated with each substrate to form an ion filter section, and a contact part configured to apply controlling signals to the electrodes, and the electronics part applying a compensated asymmetric periodic signal across the filter electrodes for changing the flow of ions in the flow channel. The electronics part may be further configured to sweep the applied controlling signals through a predetermined range according to the species being filtered. The input part may include an ionization source for the ionization of gas samples drawn by a flow pump, further comprising a second pump for recirculation of air in at least one flow channel.

Preferably in another embodiment, a high field asymmetric waveform ion mobility system includes a spacer and substrates forming a spectrometer chip housing extending along a longitudinal axis and defining an internal flow channel between a sample inlet and an outlet, an ion filter disposed in the flow channel and including a pair of spaced filter electrodes, the ion filter further defining planar substrate surfaces opposite each other and carrying the spaced filter electrodes opposite each other separated by the spacer; and an electrical controller for applying a compensated asymmetric periodic voltage across the ion filter electrodes and for generating a control field, the control field controlling the paths of ions traveling through the filter along the longitudinal axis toward the outlet.

The system may include: wherein the outlet further has a etection area, the spacer having a channel extending along the longitudinal axis and connecting the input to the detection area, ions passed by the filter traveling to the detection area for detection; or wherein the detection area includes at least a pair of detector electrodes, further having an isolation part separating the ion filter from the detector, the isolating part isolating the control field from the detector electrodes; or wherein the isolation part has an insulated surface area along the flow channel. The system may include wherein the isolation part further has a guard electrode on at least one substrate formed between the filter electrode and the detector electrode on the substrate; or wherein the spacer further is defined as longitudinal extensions extending along the longitudinal axis, and the flow channel between the longitudinal extensions extending along the longitudinal axis. The system may include a source of ions at the inlet, a pump communicating with the flow channel, the ions flowing through the filter under influence of the pump. A heater may be provided for heating the flow channel and purging neutralized ions, and the heater may have a pair of electrodes, the electrodes having at least one additional function, or they may be formed as heater elements. The electrical controller may be configured to selectively apply a current through the filter electrodes to generate heat.

Preferably in another embodiment, a micromechanical high field asymmetric waveform ion mobility system includes a pair of spaced planar substrates defining between them a flow channel between a sample inlet and an outlet, an ion filter disposed in the path, further including at least a pair of spaced electrodes, the filter defining at least one of the electrodes on each substrate opposite each other, an electrical controller for applying voltages, including a compensated asymmetric periodic voltage applied to the filter, for controlling the paths of ions through the filter; and a heater for heating the flow channel. Optionally, wherein a pair of the electrodes on the substrates is used as a heat source for the heater, the electrical controller configured to deliver a heater signal to the heat source. The electrodes may further define a pair of detector electrodes. The filter electrodes may be a heat source for the heater, the electrical controller configured to deliver a bias voltage and a heater voltage to the filter electrodes.

Preferably in another embodiment, a high field asymmetric waveform ion mobility system includes a flow channel extending between a sample inlet and an outlet, an ion filter disposed in the flow channel, the ion filter further defining electrodes opposite each other, an electrical controller configured to apply a compensated asymmetric periodic voltage across the ion filter electrodes for controlling the path of ions through the ion filter; and a selection circuit configured for selectively adjusting the duty cycle of the asymmetric periodic voltage to enable ion species from the sample inlet to be separated, with desired species being passing through the filter for detection. Preferably, wherein the asymmetric periodic voltage is not compensated with a bias voltage, further including a detector downstream from the ion filter for detecting ion species that are passed by the filter.

Preferably, in an ion mobility filter system having a flow channel that defines an ion inlet, an output, and an ion filter in the flow channel between the inlet and the output, the filter passing ions flowing from the inlet to the output, a method for filtering ions, the method defines the steps of: applying a compensated asymmetric periodic voltage to the ion filter for controlling the path of ions in the filter, adjusting the duty cycle of the asymmetric periodic voltage to enable ion species to be separated according to their mobilities, and passing species through the filter according to the duty cycle for detection at the output part.

Preferably, an ion mobility filter system defines a spectrometer chip with a pair of electrode-carrying surfaces facing each other across a gap, the gap influenced by a spacer part, the substrate surfaces and the spacer part cooperating to form a flow channel, including at least a pair of filter electrodes facing each other across the gap, an ion supply region, ions from the region flowing in the flow channel and having a flow path passing between the filter electrodes, the filter electrodes applying compensated asymmetric mobility-controlling fields across the gap, the filter filtering the ions according to their mobility in the fields, with selected ions with selected mobility passing though the filter, and electrical contacts through which an asymmetric periodic voltage is applied to the ion filter electrodes for generating the fields and controlling the filtering. Preferably the flow channel is hermetically sealed (except, of course, at the inlet and outlet), so as to minimize sample loss.

Preferably, an ion mobility filter system defines a spectrometer chip assembly (or package) with a pair of electrode-carrying surfaces facing each other across a gap, the gap fixed by the package, the package forming a hermetically sealed flow channel for the flow of samples between an inlet and ion region and an outlet region, at least a pair of filter electrodes along the flow channel facing each other across the gap, ions flowing in the flow channel from the ion region along the flow channel and passing between the filter electrodes, the filter electrodes applying compensated asymmetric mobility-controlling fields across the gap and filtering the ions according to their mobility in the fields, with selected ions with selected mobility passing though the filter in the flow channel to the outlet region, where the passage is correlated with the applied fields. Preferably the flow channel has generally planar surfaces and the electrode-carrying surfaces are defined by insulative substrates.

Electrical contact pads on the spectrometer chip assembly may be provided through which the asymmetric periodic voltage is applied to the filter electrodes for generating the fields and controlling the filtering. The contact pads on the spectrometer chip assembly avail electrical connection with a controller, the controller providing the voltage and bias signal to the filter electrodes. The system may further have contact pads on the spectrometer chip assembly for connection of the detector electrodes to the controller for control of the detector electrodes and for output of detection signals that are correlated with the compensated applied asymmetric voltages.

Preferably in another embodiment, an ion detection system based on ion mobility defines a spectrometer chip assembly having internal electrodes for generation of an electric field based on an applied compensated asymmetric waveform, the spectrometer chip assembly further defining an internal flow channel for flow of ions in an ionized sample, the ions flowing in the flow channel between the pair of electrodes and being subjected to the field for separating the ions based on their mobility in the field. The system may have the flow channel with a sample inlet for receipt of a sample in a carrier flow, the sample being subjected to an ionization source to create the ionized sample. The flow channel has an outlet for the carrier flow exiting the flow channel. The system further having an ion source in the flow channel for ionization of the sample.

A spacer defines a channel in the chip assembly and the flow channel is defined along the length of the channel. The package has insulating substrates, the substrates cooperating with a spacer to define the flow channel. The system further has an I/O section, a planar FAIMS section and a control section, wherein the sample is ionized in section and is filtered at the filter of the filter section by the application of the compensated asymmetric waveform. Preferably the I/O section includes an ion section defined between the substrates and the PFAIMS section includes a filter and detector defined between the substrates. The system may further include an on-board detector formed by electrodes defined on the substrates, wherein the filtered ions are delivered to the detector for detection, wherein the planar FAIMS section is controlled and ion detection signals are evaluated and reported by the controller section.

In an embodiment of the invention, the controller section comprises electrical contacts on the package for communication with off-board circuits, wherein the planar FAIMS section is controlled and ion detection signals are evaluated and reported by the off-board circuits.

The I/O section further includes ionization source to ionize the gas flow from inlet as it is drawn through the PFAIMS filter and detector, under direction of drive and control electronics. The system further has a control circuit to enable detecting a mixture of ion species in the sample, the control circuit causing electric fields applied between the filter electrodes to be scanned over a range and a spectrum to be generated. The substrates are planar ceramic substrates and the spacer frame acts for separation of the substrates.

In an embodiment, the substrates are planar substrates, one substrate further comprising a spacer for separation of the substrates facing each other. Any of the substrates and spacer frame are ceramic. The substrates and spacer frame are hermetically sealed together to form a housing. The system further defining a housing, wherein an inlet tube, outlet tube, ion source and electrical leads mounted on the housing. The housing is formed by the substrates and spacer. Electrodes are formed with metalization segments, including filter electrodes and detector electrodes, and one the metalization segment further defining a shielding electrode to shield a the detector electrode from the fields. The electrodes may further define heater electrodes.

In this system, an ionization access port is defined in one substrate for receipt of ions from an ionization source and an attraction electrode on the other substrate for attraction of the ions into the flow channel. In various embodiments bonding pads are defined on the substrates that mate with bonding pads on the receiver assembly, for connection to leads for connection to off board circuits. The substrates and spacer cooperate to form a hermetically sealed flow channel wherein the substrates have planar working surfaces and with spacer cooperate to form a spectrometer chip housing. The substrates include ion filter electrodes and detector electrodes, and may include other electrodes and a heater electrode.

In embodiments of the invention, a spectrometer system defines a chip assembly formed having at least a pair of substrates separated by a spacer. The substrates and spacer define a multi-layer package. One substrate and the spacer form a socket receiver assembly, and the other substrate mounts into the socket receiver assembly. The spacer in one example is a 0.5 mm thick planar co-fired ceramic and forms the flow channel side walls while acting as a spacer to establish separation between the ion filter electrodes. The spacer and bottom substrate are formed as one piece. The substrates and spacer are bonded together using glass flit as a bonding agent. One substrate includes an inlet tube and an outlet tube coupled thereto. Connection to a lead for one substrate filter electrode is made between a bonding pad of the upper substrate to a bonding pad on the upper surface of the receiver assembly, which directly connects to a lead.

Preferably, the spectrometer includes a pin grid array, wherein the spacer cooperates with one substrate to provide electrical connection to the second substrate. In an embodiment, chip assembly is formed with the substrate and spacer sections and the pin grid array is formed as part of at least one of the sections. In an embodiment, the spacer has vias or castellations to provide electrical connection from one side of the spacer to the other, to enable communication from one substrate to the other through the spacer. Preferably the flow channel is hermetically sealed.

It will be appreciated that the spacer is a mechanical separator, forming sidebars or sidewalls of the chip assembly, a precision locator of the substrates that must face each other precisely across a gap established by the spacer, and an electrical connector or bridge enabling electrical communication through the spacer. Preferably, one substrate is placed on the spacer with its bonding pads contacting metalized sidewalls of the spacer directly or with addition of solder ball bonding, and addition of sealing, preferably glass frit, such that the substrate is in communication with pins 216 on the other substrate, while forming a hermetically sealed flow channel.

Preferably, a spectrometer system of the invention defines a substrate mounted to a combined spacer-substrate assembly. The assembly defines integral spacer walls and a substrate. In this embodiment, the spectrometer further has metalization patterns on the substrates forming electrodes, wherein the lower surface of the upper substrate is bonded to the top surface of the sidewalls to form a hermetically sealed flow channel. The spacer walls extend over the edges of the electrodes to guide the flowing sample over and between the filter electrodes.

Preferably, a spectrometer system of the invention has substrates mated via a spacer with electrodes on the substrates facing each other over a gap. The spacer defines the gap. The substrates and spacer define a flow channel. The spacer further includes sidewalls, the sidewalls overlapping the electrodes. This configuration assures that ions passing down the flow channel must pass between the filter electrodes or hit the sidewalls. Preferably, one substrate and the spacer form a substrate with shoulders. This assembly is mated to a substrate with shoulders. This forms two shoulder pairs. The shoulder pairs cooperate to form a spacer assembly performing a spacing function that assures a precise gap and a parallel relationship of the electrodes facing each other in the flow channel. These shoulders extend into flanges, wherein the substrates are joined and the flanges are mated together with bonding agent to form a hermetically sealed flow channel. The system further defines lips to provide for accurate alignment, mating and seating of substrate with substrate during assembly.

The mated flanges of the mated substrates form wings. Metalization patterns are formed on these wings and forming edge connectors with pinouts. The substrates and spacer form a chip assembly, further defining an inlet tube and outlet tube on the package. The package is tapered to define an inlet tube as a longitudinal extension of the chip assembly, extending along a longitudinal axis A. The extension has an external coupling detail to assist coupling to an external connector. The substrates and spacer form a chip assembly, the package tapered to define an outlet tube as a longitudinal extension of the chip assembly, extending along the longitudinal axis A. The extension forms a coupling mechanism and may have an external coupling detail to assist coupling to an external connector.

In still another embodiment, preferably the spacer is formed with two spacer bars that cooperate with the substrates to define the flow channel. The spacer bars define the area of the flow channel and restrict the sample flow path to be over and between the electrode surfaces.

Preferably, the system further defines heater elements and contact pads formed on the substrates. The heater elements are preferably covered with a thermally insulating layer.

Preferably the spacer and the substrates are ceramic, wherein the spacer and the substrates form a chip assembly and the package mid-section extends laterally into chip assembly wings, formed by substrate wings. The spacer sidewalls are formed as spacer bars and the package wings extend laterally beyond the spacer bars to define an area between each set of substrate wings to form wing areas. This further defines bonding pads on the substrates in these wing areas, forming edge connectors. Also provided are mating edge connectors on a connector assembly to facilitate off-chip connection. A coupling on one substrate for coupling to an external detector is provided, wherein the substrate includes a detector outlet port formed as an orifice in the substrate through detector electrode for output of ions to the intake of a detector, such as an MS. In this system, a shielding electrode is formed adjacent the detector electrode to guard same from the filter signal.

In a further embodiment, a circuit board defines the spacer. The circuit board defines a window, wherein the substrates are mounted over the window facing each other and forming a flow channel, the circuit board performing a spacing function that assures a precise gap and a parallel relationship of the electrodes on the substrates facing each other in the flow channel. Additional components can be mounted on the circuit board, including any driver, control and i/o circuits.

In a process for forming a spectrometer chip, steps include: forming a spacer die from insulating material, forming a plurality of spacers in the die, forming each the spacer with a defined spacer channel, forming the die with dicing lines running through a series of vias, forming metalized sidewalls in the vias, and dicing the die along the dicing lines into separate spacers with metalized sidewall vias.

A spectrometer system has at least a pair of substrates that are separated by a spacer, the substrates and spacer define a multi-layer package. One substrate and the spacer form a socket receiver assembly. Another substrate mounts into the socket receiver assembly. Connection to a lead for one substrate filter electrode is made between a bonding pad of one substrate to a bonding pad on the upper surface of the receiver assembly, which directly connects to a lead for connection off-chip. The steps of forming spectrometer include loading a solder ball at the connection point between bonding pads and surrounding area with a sea of glass frit, heating same, and forming a sealed, preferably hermetically sealed, flow channel while establishing electrical connections between the substrates, spacer and electrical lead.

Another process for forming a spectrometer chip defines the steps of forming electrodes and bonding pads on one substrate, forming the spacer as a spacer frame, forming the spacer frame from glass tape with punched holes, and loading metal therein, loading this loaded spacer on the other the substrate with a layer of bonding agent in between, and loading a layer of bonding agent on the spacer and loading the other substrate thereon, and heating same to melt the metal to form electrical paths and to melt the bonding agent to make a hermetic seal in forming the flow channel.

In a spectrometer system having at least a pair of substrates and separated by a spacer, the substrates and spacer define a multi-layer package. One substrate and the spacer form a socket receiver assembly. Another substrate mounts into the socket receiver assembly. Connection to a lead for one substrate filter electrode is made between a bonding pad of one the substrate to a bonding pad on the upper surface of the receiver assembly. This directly connects to a lead for connection to off-board circuits.

In a process for forming the spectrometer, the steps include placing a spacer on a lower substrate along with solder balls and glass frit, and heating same to form a rigid workpiece.

As will be appreciated by a person skilled in the art, operationally the pressure in the flow channel in practice of the invention may be either higher or lower than the pressure outside of the substrates. Nevertheless, in these cases, the invention may be referred to as operating at ambient pressure. Mass spectrometers operate on samples in a low pressure environment. IMS is said to operate at ambient pressure, and the present invention may be so characterized.

While preferred embodiments of the invention are set forth above, still additional features and aspects of the invention are set forth below in the detailed description. These and other objects are well met by the presently disclosed invention. The present invention overcomes cost, size or performance limitations of MS, TOF-IMS, FAIMS, FIS and other prior art devices, in a novel method and apparatus for chemical species discrimination based on differences in ion mobility in a compact package.

The present invention provides apparatus for the analysis of compounds using high field asymmetric waveform ion mobility spectrometry (FAIMS). Preferably the apparatus is formed as a FAIMS spectrometer chip. Methods of operation and manufacture are disclosed.

In one embodiment of the present invention, planar electrodes are formed on planar substrate surfaces. This structure enables use of state of the art mass production processes, and results in low-cost, high-quality spectrometer chips and systems.

Preferably the planar surfaces of the substrates are used as a platform for the forming of the electrodes of the FAIMS spectrometer on a chip. This planar FAIMS innovation is referred to as "PFAIMS". The average PFAIMS detection limits are comparable to or better than those of much larger IMS systems.

Unlike a mass spectrometer or an IMS, the PFAIMS allows the simultaneous detection of both positive and negative spectra, such as where detector electrodes are each run as independent outputs to the data system, eliminating the need for serial analysis under different instrumental conditions. It is also possible when coupled to a GC to present a unique 2-dimensional plot of compensation voltage versus retention time for discrimination of ion species.

One advantage of the PFAIMS invention is that a combined GC-PFAIMS offers the ability to obtain unambiguous compound identification, based on a combination of generated data that provides a means of fingerprinting the compounds eluted from the GC into the PFAIMS sensor system. In the field, or under particular conditions, such as environmental conditions, variable humidity or sample concentrations, the retention times of compounds may shift from their expected values. When analyzing an unknown complex mixture, this is a serious problem. In order to correct for this shift, a known standard, at a known concentration, is run through the GC first to calibrate the GC. Running a standard however, takes time and adds complexity; furthermore, the standard is a consumable, and is inconvenient to use in the field. Because the PFAIMS provides a second dimension of information, even though the GC retention time for the different compounds may shift, the additional information provided by the PFAIMS spectra can provide an accurate identification of the compound without the need of a standard.

Simultaneous detection of positive and negative ions cuts down on analysis time, since only one scan is required to obtain multiple species detection, which is a generally valuable improvement, and is specifically important when limited samples are available and measurements can only be performed once. Also the invention provides a much richer information content compared to TOF-IMS, so that one can get a better identification of the ion species being detected.

Embodiments of the claimed invention result in PFAIMS devices that achieve high resolution, fast operation and high sensitivity, yet with a low parts count and in configurations that can be cost-effectively manufactured and assembled in high volume. Quite remarkably, packaging is very compact for such a capable device, with sensitivity as low as of parts per billion or trillion. In addition, the reduced real estate of this smaller device leads to reduced power requirements, whether in sensing ions or in heating the device surfaces, and can enable use of a smaller battery. This reduced power requirement and size can be very important in fielding portable devices, such as in fielding a portable chemical sensor, for example, made in practice of the invention.

It will therefore be appreciated by a person skilled in the art that the claimed invention provides the possibility of a small PFAIMS device with low parts count, with parts that themselves are simplified in design. Devices of the invention can be volume-manufactured with high production yields. The simplicity of the structure also quite remarkably leads to favorable performance improvements. The result is a compact, low-cost device with high quality and performance.

Nothing like the claimed invention has been disclosed or achieved in the past. The novel breakthrough of the present invention, in one aspect, can be attributed to providing a multi-use housing/substrate structure that simplifies formation of the component parts. Additional features include the possibility to use the substrate as a physical platform for add-on equipment, such as to build a GC receiver in proper alignment with an ionizer, and further to be able to build the filter and detector on the substrate. In short, to be able to give structure to the whole device, to use the substrate as an insulated platform or enclosure that defines the flow path through the device, and/or to be able use the substrate to provide an isolating structure that improves performance. Multiple electrode formations, and a functional spacer arrangement are also taught, which again improve performance and capability.

In practice of the PFAIMS apparatus of the invention, filtering employs the asymmetric period voltage applied to the filters along with a control component, and this component need not be a bias voltage but may be supplied simply by control of the duty cycle of the same asymmetric signal. A spacer can be incorporated into the device, which provides both a defining structure and also the possibility of a pair of electrodes for further biasing control. Also, this compact arrangement enables inclusion of a heater for purging ions, and may even include use of the filter or detector electrodes for heating/temperature control.

The preferred embodiment of the present invention employs a field asymmetric ion mobility filtering technique that uses high frequency high voltage waveforms. The fields are applied perpendicular to ion transport, favoring a planar configuration. This planar configuration allows flow channels to be fabricated inexpensively with small dimensions. Also, electronics can be miniaturized, and total estimated power can be as low as a few watts, a level that is suitable for field instrumentation.

Another advantage of the PFAIMS device over the FIS device is the ability to incorporate arrays of devices. The fact that arrays of PFAIMS filters is possible means that each filter in the array can be set to detect a particular compound. Rather than having to change the filter conditions to a different setting to detect a different compound, a number of compounds, defined by the number of filters in the array, can be detected simultaneously.

It will now be appreciated that the present invention provides improvements in methodology and apparatus for high field asymmetric waveform ion mobility spectrometry, from the environment or from other sources, such as gas chromatographic analyzer intimately coupled with the ionization section. With a separator, the device includes an ion filter section, and an ion detection section, in which the sample compounds are at least somewhat separated prior to ionization, and ion filtering proceeds in a planar chamber under influence of high field asymmetric periodic signals, with detection integrated into the flow path, for producing accurate, real-time, orthogonal data for identification of a broad range of chemical compounds. Ceramic embodiments of the present invention also provide PFAIMS devices capable of withstanding a wide range of temperatures and conditions.

Application of embodiments of the invention enable robust, compact, reduced cost, high performance, chemical detection and analysis systems. These are operable in laboratory and factory locations, as well as on-board in mobile equipment and mobile installations. Portable equipment in practice of the invention includes chemical detectors and explosives sensors, and the like. It will be appreciated that the term flow channel refers to a physical structure such as a channel defined in cooperation with substrates to form a flow channel. The flow path is the path that the sample travels from inlet to outlet, which includes travel in the flow channel. The terms flow path and flow channel may be used interchangeably in the following description and still remain in the scope of the invention.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 8(c) is a perspective view of a substrate with electrodes in practice of the invention.

FIG. 8(d) is a perspective view of spacer in practice of the embodiment of FIG. 8(a).

FIG. 8(i) is a cross-sectional view taken through line i—i of FIG. 8(h) in practice of the invention.

FIG. 8(n) is an exploded perspective view of a chip assembly in practice of the invention.

FIG. 8(o) is a partial side cross sectional view of a chip assembly in practice of the invention.

FIG. 8(q) is a side cross sectional view of a chip assembly in practice of the invention showing electrical connection of one substrate to another using a spacer frame with electrical feed through.

FIG. 8(s)(1) is plan view of a die in practice of the invention.

FIG. 8(s)(2) is a perspective view of a metalized wall of the die of FIG. 8(s)(1).

FIG. 8(t)(1) is a plan view of a combined spacer and substrate assembly in practice of the invention.

FIG. 8(t)(2) is cross sectional view of an embodiment of the invention incorporating the combined spacer and substrate assembly of FIG. 8(t)(1).

FIG. 8(t)(3) is a partial side cross section view of an alternative combined spacer and substrate assembly in practice of the invention.

FIG. 8(t)(4) is a partial side view of a socket, which cooperates with the edge connectors of the embodiment of FIG. 8(t)(4).

FIG. 8(u)(1) is a partial perspective view of an alternative inlet location in practice of the invention.

FIG. 8(u)(2)(i) is a top view of an alternative chip configuration in practice of the invention.

FIG. 8(u)(2)(ii) is a cross section taken through line ii—ii of FIG. 8(u)(2)(i).

FIG. 8(u)(2)(iii) is a cross section taken through line iii—iii of FIG. 8(u)(2)(i).

FIG. 8(u)(2)(iv) partial perspective view of mating edge connector assembly in practice of the invention.

FIG. 8(v) is a partial perspective view of an alternative embodiment of the invention for coupling to an external detector in practice of the invention.

FIG. 8(z)(1–2) are plan views of a circuit board spectrometer in practice of the invention.

DETAILED DESCRIPTION OF A PREFERRED EMBODIMENT

A description of preferred embodiments of the invention follows.

The present invention provides apparatus for the analysis of compounds using principals of high field asymmetric waveform ion mobility spectrometry (FAIMS). Preferably, the apparatus is a spectrometer chip or spectrometer engine that performs the FAIMS function and provides a useful output representative of filtered ions.

Figures 1, 2A:
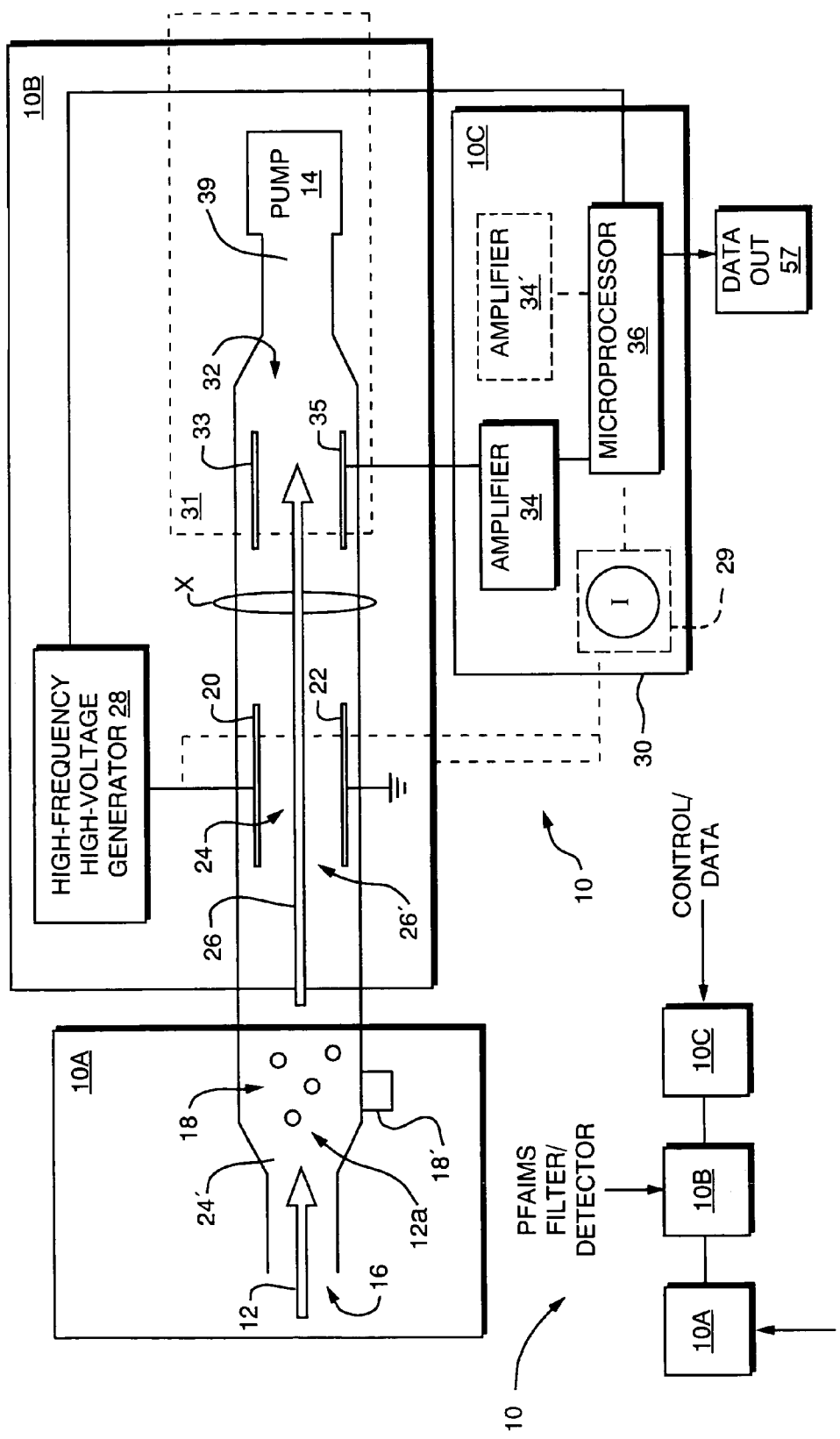
FIG. 1 is a block diagram of a chemical analysis system of the present invention.
FIG. 2(a) is a schematic of a PFAIMS device of the invention.

As shown in FIG. 1, a Planar FAIMS (PFAIMS) chemical sensor system 10 according to the invention includes front end section 10A, electrode section 10B, and control section 10C. Front end section 10A may open directly to the environment for receipt of samples or may receive conditioned samples, such as those eluting from a liquid or gas chromatograph or the like, and then provides ionized samples to filter/detector section 10B for filtering and detection of ions, all under control of control section 10C.

In one embodiment, shown in the schematic of FIG. 2(a), front end section 10A includes a sample inlet 16 for receipt of compounds in carrier gas flow 12 which flows into ionization region 18. Preferably gas flow 12 is heated before or during delivery into inlet 16.

The samples are ionized in ionization region 18 by an ionization source 18'. The ionization source may be internal or external to region 18, but in either event causes ionization of compounds passing through region 18 along flow path 26 in gas flow 12, and flowing into filter 24 of filter/detector section 10B.

Figure 3A:
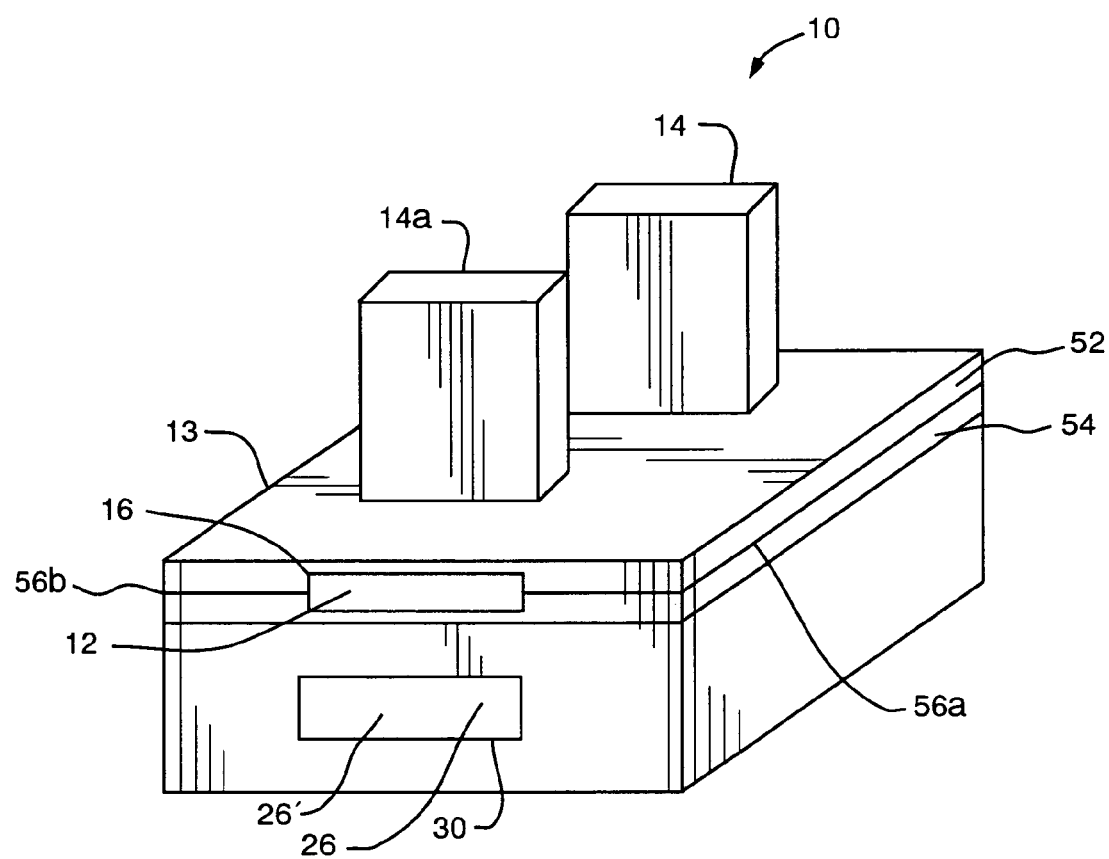
FIG. 3(a) is a perspective view of a PFAIMS embodiment of the invention.
Figure 3B:
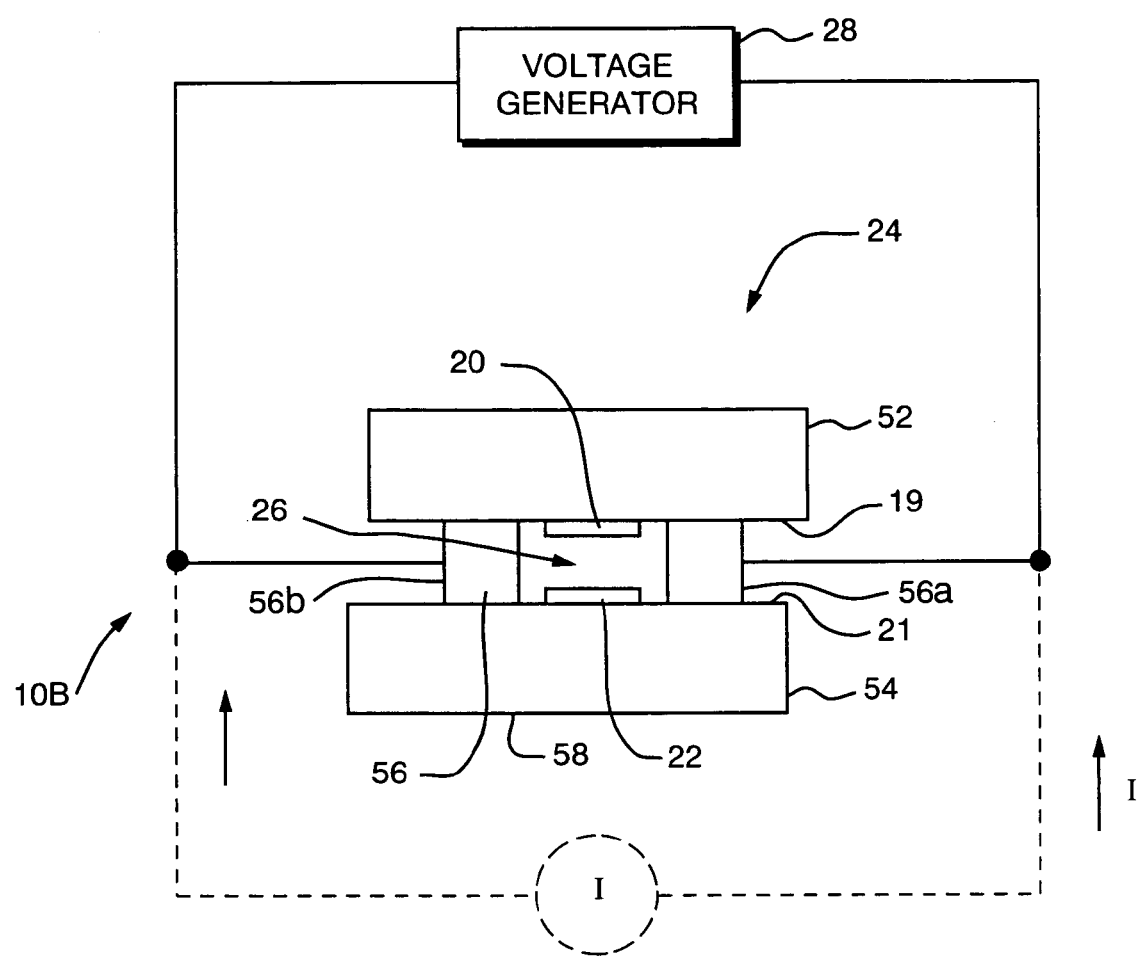
FIG. 3(b) is a side cross-sectional view of the embodiment of FIG. 3(a) (without pumps) showing the spacer and spaced substrates.

Filter/detector section 10B is defined in FIG. 3(b) by spaced insulated or insulating substrates 52, 54, (e.g., Pyrex® glass, Teflon®, ceramic, pc-board, silicon nitride, or the like). Filter electrodes 20, 22 are formed of conducting material (e.g., gold, platinum, silver, palladium, tungsten, or the like) on insulated surfaces 19, 21 of substrates 52, 54. The substrates 52, 54 and spacer 56 further define between themselves the inlet 16 and output region 31, along flow path 26. Preferably output region 31 also includes a detector 32, with detector electrodes 33, 35 mounted on insulated surfaces 19, 21, facing each other across the flow path 26. Substrates 52, 54 may also cooperate to structurally form front end section 10A.

In one embodiment, control section 10C includes an output and display device 57 to provide detection indications when ions passed by filter electrodes 20, 22 strike detector electrodes 33, 35. However, in another embodiment, output region 31 may couple directly to a mass spectrometer or other detector devices, which themselves may provide detection indications of the ions passed by filter electrodes 20, 22.

As shown in the illustrative embodiment of FIG. 3(a, b), a pump 14 may be provided that generates air flow for carrier gas flow 12, for drawing the ionized sample through section 10B and filtered ions into output region 31 and out via outlet 39 into the pump. Pump 14 may be part of the device or it may be separate. A pump 14a can be used for recirculation to supply conditioned air to the flow path 26; (see flow path 26", FIG. 6). However, it will also be appreciated that the gas flow can be generated by an inflow eluting from a GC under pressure and exiting out outlet 39 to the environment, without the need for pump 14.

It will now be appreciated that front end section 10A in the schematic of FIG. 1 includes inlet 16 and outlet 39 as well as flow control. Flow control may be supplied by pump 14 under direction of controller 10C. Flow control may be provided by the flow from the GC without the need of pump 14. Flow control may also include output 39 coupling to the input of an MS, where ions out passed by the filter section 10B flow into the MS for detection.

As shown in FIG. 3(b), substrates 52, 54 are precisely positioned as parallel planes facing each other across flow path 26. This parallelism is established by a spacer 56 (having spacer segments 56a, 56b). Cooperation of the substrates and spacers defines flow channel 26' along which flow path 26 runs. In one embodiment, the substrates and spacers are made of an insulating material, or at least their working surfaces are insulated. The spacers may be integral with a substrate or may be discrete and bonded thereto.

Preferably electrodes 20, 22, 33, 35 are formed on insulated surfaces 19, 21 of substrates 52, 54. The benefit of being able to lay down electrodes on a planar insulating surface is that it lends itself to compact packaging and volume manufacturing techniques. By forming the electrodes on highly insulative substrates, the ion filter electrodes and detector electrodes can be positioned closer together, which enhances ion collection efficiency and favorably reduces the device's mass that needs to be regulated, heated and controlled. This also shortens the flow path and reduces power requirements. Furthermore, use of small electrodes reduces capacitance which also results in reduced power consumption.

Filter electrodes 20, 22 are separated from detector electrodes 33, 35 by an isolation region X, FIG. 2(a). As such, the ion filter is defined on these insulated surfaces by the filter electrodes, facing each other over the flow path, while the insulated surfaces of the substrates, such at region X, isolate the control signal at the filter electrodes from the detector electrodes. The result is lower noise and improved performance.

As ions pass through filter 24, some are neutralized as they collide with the filter electrodes, while others pass to detector 32, depending upon signals on the filter electrodes and characteristics of the ions present. Controller 10C regulates the signal on the filter electrodes, thus regulating which ion species will pass through ion filter 24.

The ionization source 18', such as an ultraviolet photoionization lamp, converts a gas sample into a mixture of ion species with each ion type corresponding to a particular chemical in the gas sample. The ion species are then passed through ion filter 24 where the applied electric fields between electrodes selects an ion type, that is allowed to pass through the filter. Once through the filter, the ion hits a detector electrode 33, 35 and produces an electrical signal. To detect a mixture of ion species in the sample the electric fields applied between the filter electrodes can be scanned over a range and a spectrum generated.

Figure 2B:
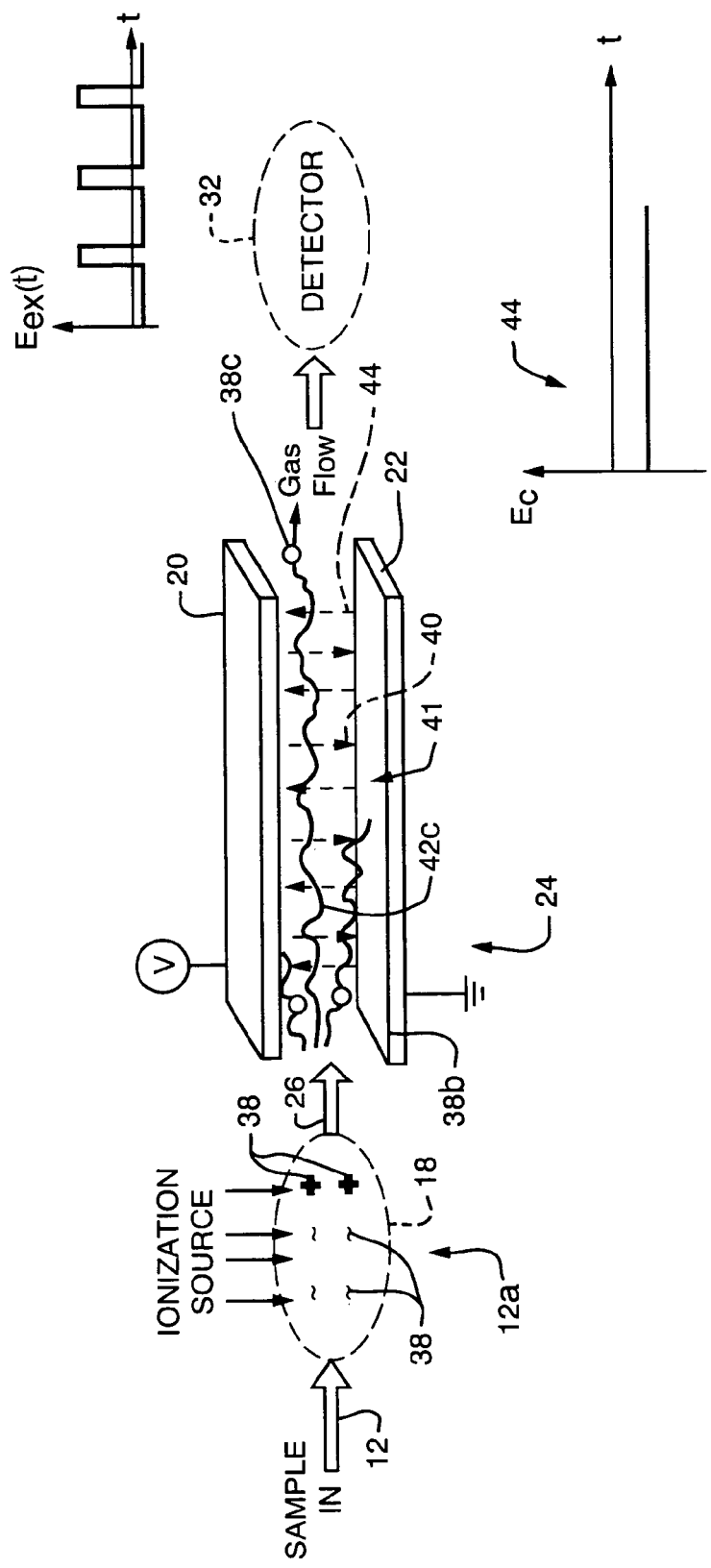
FIG. 2(b) is an exploded view of the filter electrodes and ions passing between the electrodes under influence of the applied electric field in practice of the invention.

More specifically, as shown in FIG. 2(b), FAIMS ion filtering may be achieved through the combined action of two electric fields generated between the ion filter electrodes: first is the asymmetric, periodic, radio frequency (RF) electric field 40, and second is a compensation field 41, which may be generated as a DC compensation electric field 44. The asymmetric RF field has a significant difference between its peak positive field strength and negative field strength. The asymmetric RF field scatters the ions and causes them to deflect to the ion filter electrodes 20, 22 where they are neutralized upon contact. The compensation field prevents the scattering of a particular ion species, allowing it to pass through to the detector. Thus the ions are separated due to the compound dependent behavior of their mobility at high electric fields relative to their mobility at low electric fields.

In an illustrative embodiment of the invention, the RF field is produced by a soft-switched semi-resonant circuit that incorporates a flyback transformer to rapidly generate the high voltage pulses. The circuit provides a peak-to-peak RF voltage of at least 1400 volts at a frequency of around 100 KHz–4 MHz with a duty cycle of about 10–70%. Sample RF waveforms for driving the filter electrodes are shown in FIG. 2(b), although variations thereof are also within practice of the invention.

In operation of an embodiment of the invention, ionized gas sample 12a is drawn along flow path 26 (such as under a flow generated by pump 14). The ionized sample 12a flows between the parallel filter electrode plates 20, 22 of ion filter 24, while being subjected to the high intensity asymmetric field 40 and compensation field 41. In practice of one embodiment of the invention, as shown in FIG. 2(b), the asymmetric electric signal is applied in conjunction with a compensating DC bias 44, and the result is that the filter passes ion species dictated by that compensation. In another embodiment, the asymmetric electric signal enables passing of the desired ion species where the compensation signal is in the form of variances in the duty cycle of the asymmetric electric signal that generates field 40, without the need for compensating bias voltage.

The gas flow, ionization, electric signals and filtering/detecting is under direction and control of system controller section 10C. Controller 10C receives, interprets and enables display of detection data from the detector. By sweeping compensation signal 41 over a predetermined range, the controller can generate a complete spectrum for ionized compounds in sample 12 by correlating detection signals (such as at detector 32) with applied bias levels, and then complete the detection based on historical spectra data for device 10.

It will be appreciated that embodiments of the invention feature a multi-functional use of the PFAIMS substrates. The substrates are platforms (or a physical support structure) for the precise definition and location of the component parts or sections of the device. The substrates also form a housing, enclosing the flow path with filter and perhaps detector enclosed. This multi-functional design reduces parts count while also precisely locating the component parts so that quality and consistency in volume manufacture can be achieved. The smaller device also has unexpected performance improvements, because of the shorter flow channel and also because the substrates also perform an electronic isolation function.

By being insulating or an insulator (e.g., glass or ceramic), the substrates form a direct platform for formation of components, such as electrodes, without the need for additional support and alignment structures, and with improved performance characteristics. The PFAIMS sensor with insulated substrate/flow path achieves excellent performance in a simplified structure. The use of an electrically insulated flow path in a PFAIMS device enables the applied asymmetric periodic voltage to be well isolated from the output part (e.g., from the electrodes of the detector), where detection takes place. The result is a more sensitive spectrometer in a compact and low cost volume manufacturable package. Sensitivity of parts per billion and parts per trillion can be achieved in practice of the invention.

It is further noted that use of the substrates as a support/housing does not preclude yet other "housing" parts or other structures to be built around a PFAIMS device. For example, it might be desirable to put a humidity barrier over the device. As well, additional components, like batteries, can be mounted to the outside of the substrate/housing, e.g., in an enclosure. As well, other components can be on the housing surface, such as thermocouples, heaters, other circuits, and the like. Nevertheless, embodiments of the presently claimed PFAIMS invention stand over the prior art by virtue of performance and unique structure generally, and the substrate insulation function, support function, multi-functional housing functions, specifically, as well as other novel features discussed herein.

One embodiment of the PFAIMS device is shown in FIG. 3(a), where it will be appreciated that the generally planar substrates cooperate to form a generally planar housing 13. This multi-use, low parts-count housing configuration lessens real estate requirements and leads to a smaller and more efficient operating PFAIMS system, perhaps as small as 1"×1"×1" or smaller.

In the front cross-sectional view of FIG. 3(b), the compact and self-contained embodiment of the invention 10 has the electrodes 20 and 22 formed on insulating substrates 52 and 54. Either insulating or conducting spacers 56a and 56b serve to provide a controlled gap between electrodes 20 and 22. Spacers 56a, 56b may be formed as an extension of one of the substrates or as separate components by etching or dicing silicon wafers or may be made of patterned Teflon, ceramic, or other insulators. The thickness of spacers 56a, 56b defines the distance between the substrates and electrodes 20, 22. Spacers 56a, 56b may be electrodes.

In operation, some ions will be driven into the electrodes 20, 22 and will be neutralized. These ions can be purged by heating. This heating may be accomplished in one embodiment by heating the flow path 26, such as by applying a current to filter electrodes 20, 22, or to spacers 56a, 56b. Such heating can be used to heat and regulate the ion filter region to make it insensitive to external temperature variations.

The devices of the invention have various electrode arrangements, possibly including pairs, arrays and segments. Filtering may include the single pair of filter electrodes 20, 22 (FIGS. 2a,b). But device performance may be enhanced by having a filter array 62. It will be appreciated that FIGS. 4(a,b) has multiple filters (i.e., an array 62) in a single flow channel, and FIG. 5 has multiple flow channels, each with at least a single filter or an array 62.

Filter array 62 may include a plurality of paired filter electrodes 20a–e and 22a–e and may simultaneously pass different ion species by control of the applied signals for each electrode pair. In addition, it is possible to sweep the control component for each pair over a voltage range for filtering a spectrum of ions.

Further, with an array of filters, a complete spectral range of compensation voltages can be more rapidly scanned than with a single filter. In an array configuration, each filter can be used to scan over a smaller voltage range. The combination of all of these scans results in sweeping the desired full spectrum in a reduced time period. If there are three filters, for example, the spectrum can be divided into three portions and each is assigned to one of the filters, and all three can be measured simultaneously.

In another mode, filter array 62 may include paired filter electrodes 20a–e and 22a–e and may simultaneously enable detection of different ion species by applying a different compensation bias voltage 44 to each filter of the array, without sweeping. In this case, only an ion species that can be compensated by this fixed compensation voltage will pass through each filter, and the intensity will be measured. In practice of the invention, array 62 may include any number of filters depending on the size and use of the spectrometer.

Figure 5:
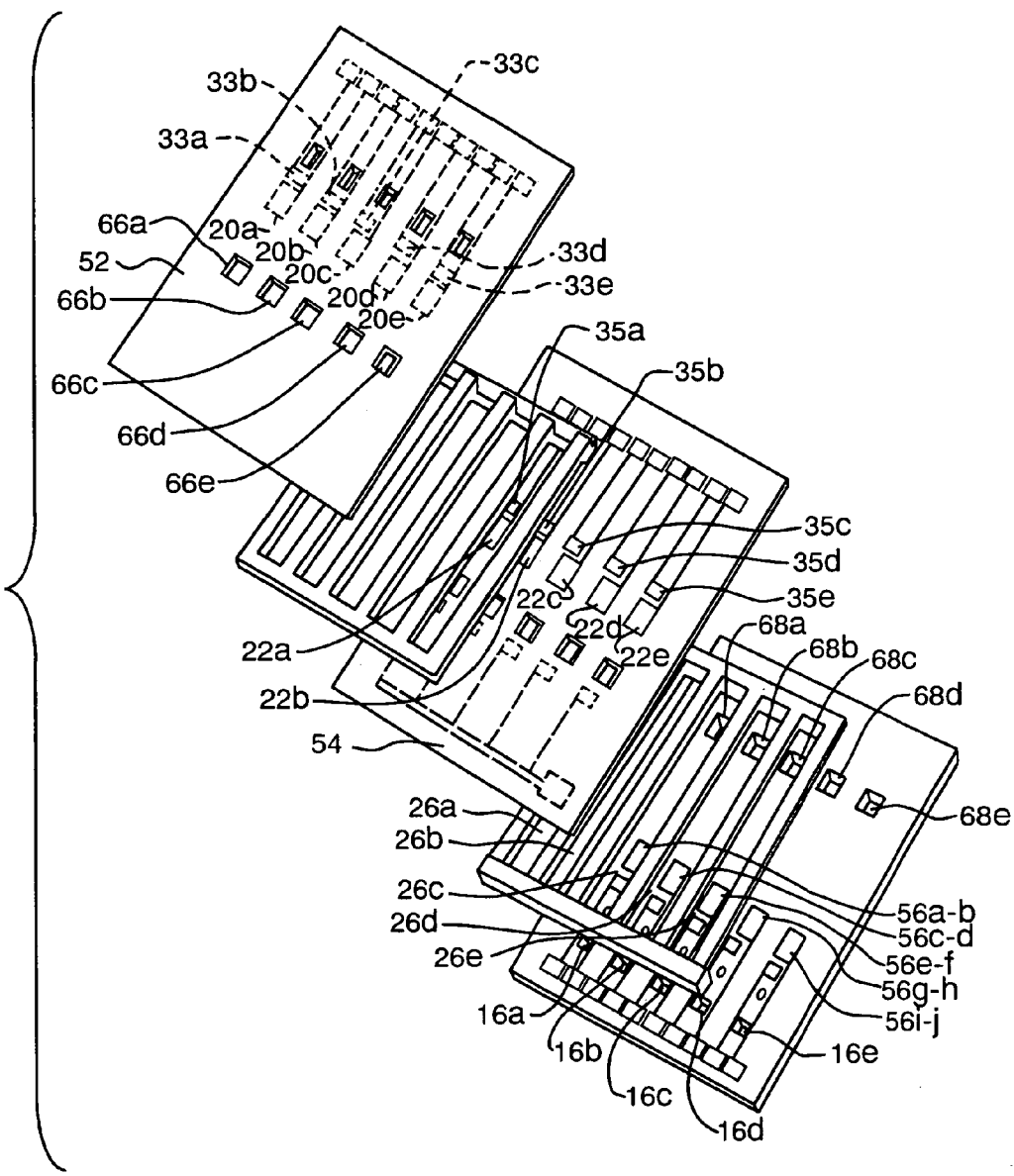
FIG. 5 is an exploded view of an array of filters and detectors with multiple flow paths.

The filter array 62 may have one common flow path 26 or individual flow paths 26a–e (FIG. 5). For each flow path, this may include an independent component set, such as for example inlet 16a, ionization region 18a, confining electrodes 56a', 56b', ion filter electrode pair 20a, 22a, detector electrode pair 33a, 35a, and exit port 68a, that may detect a particular ion species while other species are being detected. Having multiple channels provides additional information and additional flexibility in the sampling process.

Use of arrays is important when there is a desire to measure a number, perhaps even a dozen or so, compounds in a very short amount of time. Furthermore, if a fast GC is used as the front end to a PFAIMS, the widths of the chemical peaks eluting from the GC can be as short as a few seconds. In order to obtain a complete spectral sweep over the required compensation voltage range in time to capture the information contained in the GC the spectral range can be subdivided amongst the ion filters in the array. This allows a simultaneous detection of all the constituents in the given GC peak.

Figure 6:
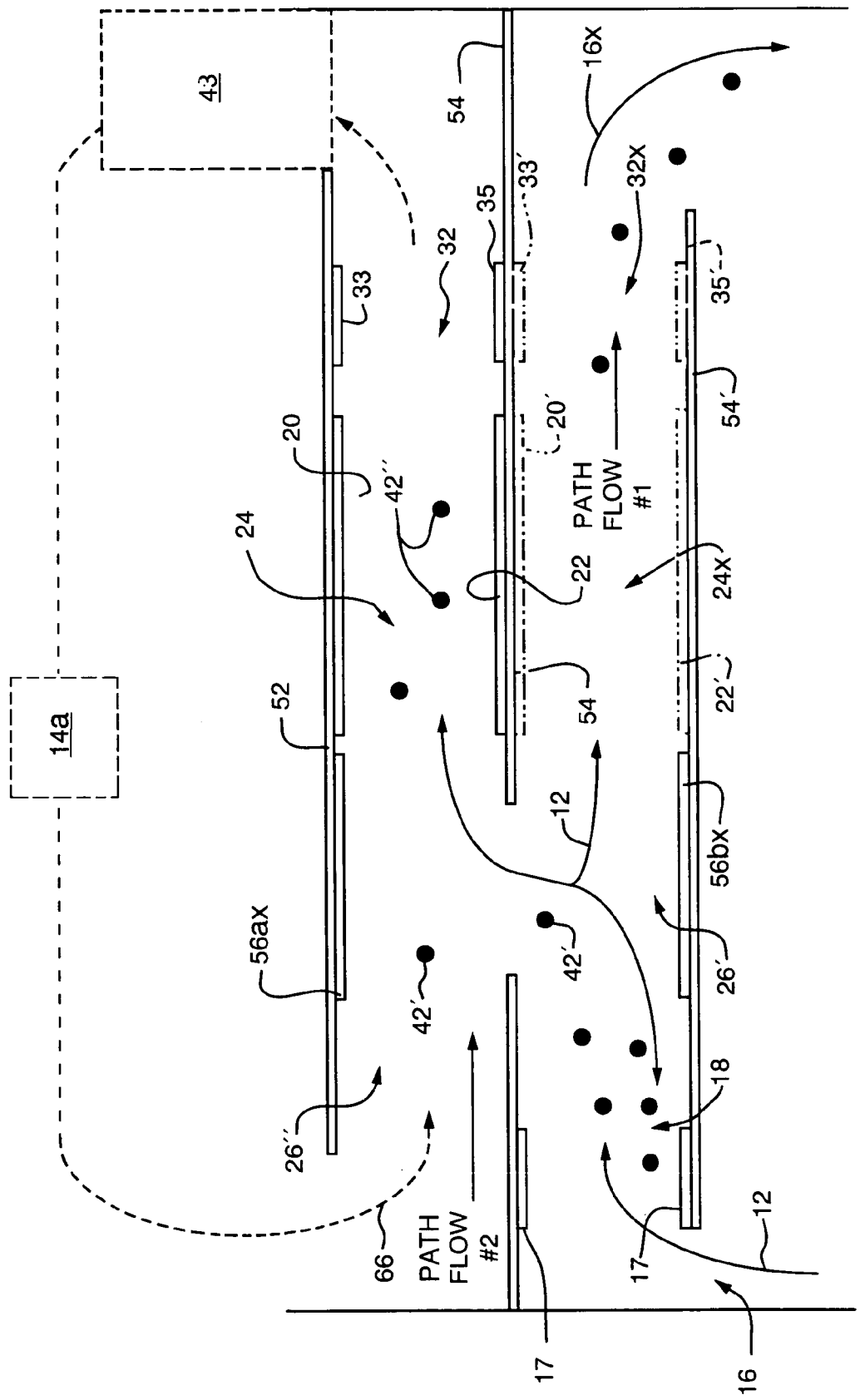
FIG. 6 is a schematic of a multi-layer PFAIMS in practice of the invention.

In further practice of the invention, detector 32 can detect single or multiple species at the same time. In one embodiment, a detector 32 includes a top electrode 33 at a predetermined voltage and a bottom electrode 35 at another level, perhaps at ground. Top electrode 33 deflects ions of the correct polarity downward to electrode 35 for detection. This arrangement is shown in FIG. 6, for example, but is not limited to this configuration. The embodiment of FIG. 6 might also have a different detector arrangement, such as a single electrode, a deflector electrodes, an MS, or other schemes, within the scope of the invention.

The design of FIG. 6 has several advantages under particular sample analysis conditions. The PFAIMS device described in FIG. 6 has two flow paths 26', 26". The sample 12 from the environment or eluting from the GC column enters inlet 16 and is ionized at ionization region 18 of flow path 26'. In this embodiment, electrodes 18 provide ionization in this region.

The ions pass between steering electrodes 56ax, 56bx and flow into flow path 26", which may contain filtered or conditioned 26'. The balance of the flow is exhausted out the gas exhaust 16x along flow path 26'. Once introduced into the ionization region 18, the sample molecules are ionized and these ions 42' are steered by electrodes 56ax, 56bx and flow into flow path 26" where they travel through the ion filter 24 electrodes 20, 22 to be detected at detector 32. According to ion mobility and the applied voltages, ions 42" pass to the detector 32. The gas is exhausted and may be cleaned, filtered and pumped at handler 43 and returned as clean filtered gas 66 back into the flow path 26".

There are several advantages of this design. Firstly, this design allows for independent control of the flow rates in flow path 26' and 26", provided the pressures are controlled at the open region between the flow paths. This means that a higher or lower flow rate of the sample can be used, depending on the input environment, such as a GC, while the flow rate of the ions through the ion filter can be maintained constant allowing, consistent, reproducible results. If the flow rate through the ion filter had to be changed due to the sample introduction system this would adversely effect the PFAIMS measurement. The efficiency of the ion filtering would be impacted and the location of the peaks (via compensation voltages) in the PFAIMS spectrometer would be different at the different flow rates. This in turn would require different high voltage high frequency fields to be used which would make for a complicated electronics system.

A second advantage is that the ion filter region can be kept free of sample neutrals. This is important when measuring samples at high concentrations coming out of a GC column. Because the amount of ions the ionization source can provide is fixed, if there are too many sample molecules, some of the neutral sample molecules may cluster with the sample ions and create large ions which do not look at all like the individual sample ions. By injecting the ions immediately into the clean gas flow in flow path 26", and due to the effect of the high voltage high frequency field, the molecules will de-cluster, and the ions will produce the expected spectra.

A third advantage is that the dynamic range of the PFAIMS detector is extended. By adjusting the ratios of the drift gas and GC-sample/carrier gas volume flow rates coming into ionization region 18 (FIG. 6) the concentration of the compounds eluting from the GC can be controlled/diluted in a known manner so that samples are delivered to the PFAIMS ion filter 24 at concentrations which are optimized for the PFAIMS filter and detector to handle. In addition, steering electrodes 56ax, 56bx can be pulsed or otherwise controlled to determine how many ions at a given time enter into flow path 26".

Flow path 26' in FIG. 6 may also contain ion filter 24x. In this arrangement, parallel PFAIMS devices are presented, where filter 24x has electrodes 20', 22', as shown in phantom, and possibly also detector 32x having electrodes 33', 35', in phantom.

In this embodiment, different gas conditions may be presented in each. With a suitable control applied to the two steering electrode 56ax, 56bx selection can be made as to which region (i.e., flow path) the ions are sent. Because each chamber can have its own gas and bias condition, multiple sets of data can be generated for a single sample. This enables improved species discrimination in a simple structure, whether or not a GC is used for sample introduction.

An electronics controller 30 supplies controlling electronic signals to the system, as in FIG. 2(*a*). A control circuit could be on-board, as in FIG. 2(*a*), or off-board, where PFAIMS spectrometer system 10 has at least the leads and electrical bonding pads that enable connection to a control circuit. The signals from the controller are applied to the filter electrodes via electric leads 71, such as shown on the substrate in FIG. 4*b*.

Electronic controller 30 may include, for example, amplifier 34 and microprocessor 36. Amplifier 34 amplifies the output of detector 32, which is a function of the charge collected on electrode 35 and provides the output to microprocessor 36 for analysis. Similarly, amplifier 34' may be provided where electrode 33 is also utilized as a detector. Thus, either electrode may detect ions depending on the ion charge and the voltage applied to the electrodes; multiple ions may be detected by using top electrode 33 as one detector at one polarity and bottom electrode 35 as a second detector at another polarity, and using two different amplifiers. Thus a PFAIMS sensor of the invention may achieve multiple simultaneous detections of different ion species.

Figure 4:
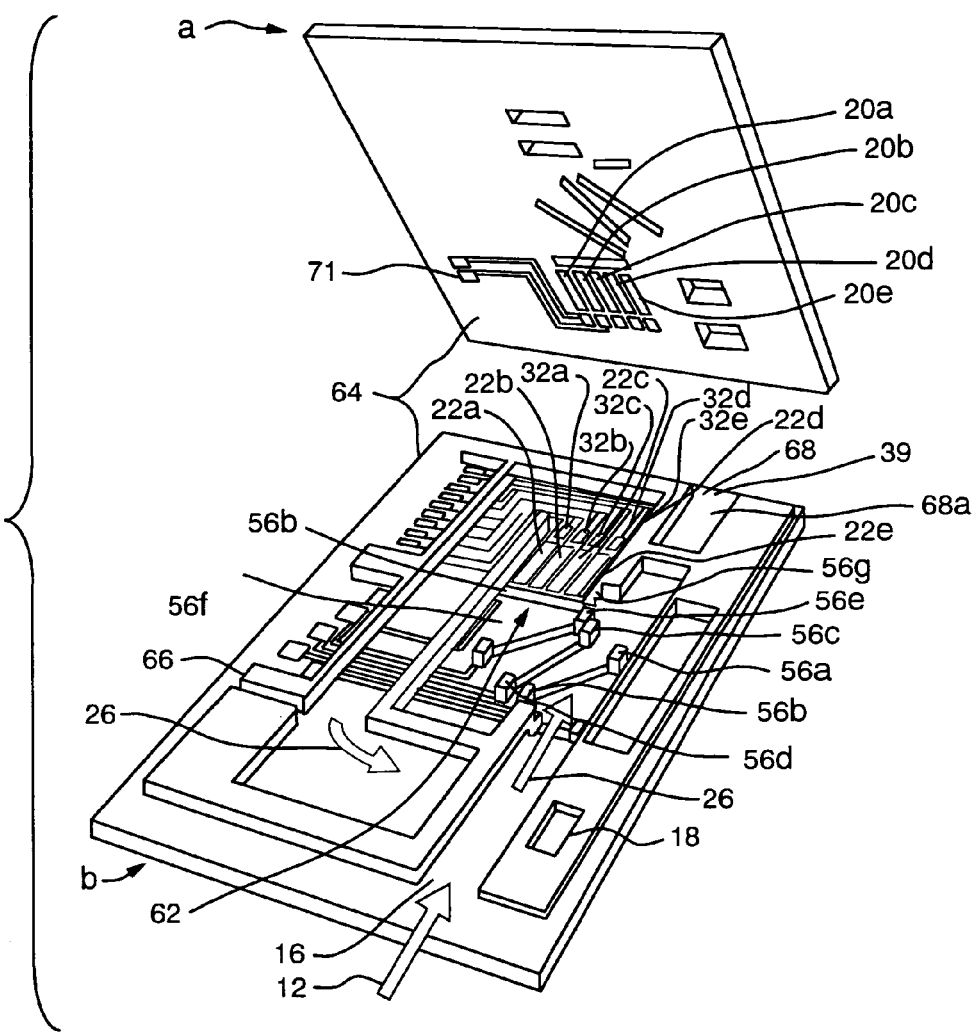
FIG. 4 is a schematic views of arrays of filter and detector electrodes in a single flow path.

Furthermore, detector array 64 may be provided with detectors 32*a*–*e* to detect multiple selected ions species simultaneously, providing faster performance by reducing the time necessary to obtain a spectrum of the gas sample (FIG. 4).

Figure 7:
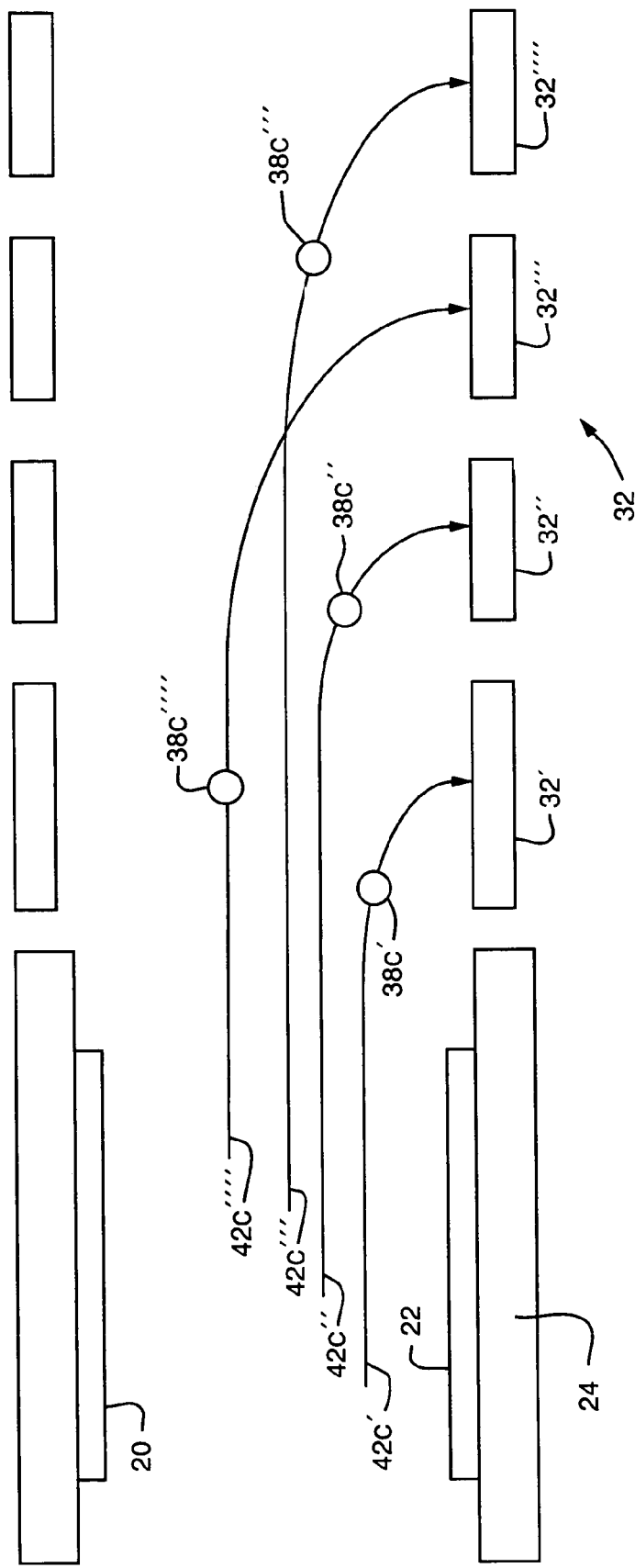
FIG. 7 is a schematic of segmented detector electrodes in practice of the invention.

In one further embodiment, to improve the PFAIMS device resolution, detector 32 may be segmented, as shown in FIG. 7. As ions pass through filter 24 between filter electrodes 20 and 22, the individual ions 38*c'*–38*c''''* may be detected by spatial separation, the ions having their trajectories 42*c'*–42*c''''* determined according to their size, charge and cross-section. Thus detector segment 32' will have a concentration of one species of ion while detector segment 32" will have a different ion species concentration, increasing the spectrum resolution as each segment may detect a particular ion species.

Turning now to FIG. 8(*a*–*z*), preferred embodiments of the invention include integrated circuit-like spectrometer packages, which may be referred to herein interchangeably as spectrometer systems, assemblies, packages, chips or engines.

These spectrometer chips may be formed using thin film, thick film, co-fired ceramic "green tape", pc-board, or other methods of manufacture. It will be appreciated that preferred spectrometer assemblies of the invention include an I/O section, PFAIMS section, and control section. The control section at least includes pinouts for off-board system control and data processing and readout. In various embodiments, the control section may be entirely on-board, including controllers, processors, drivers, amplifiers, and displays.

Figure 8A:
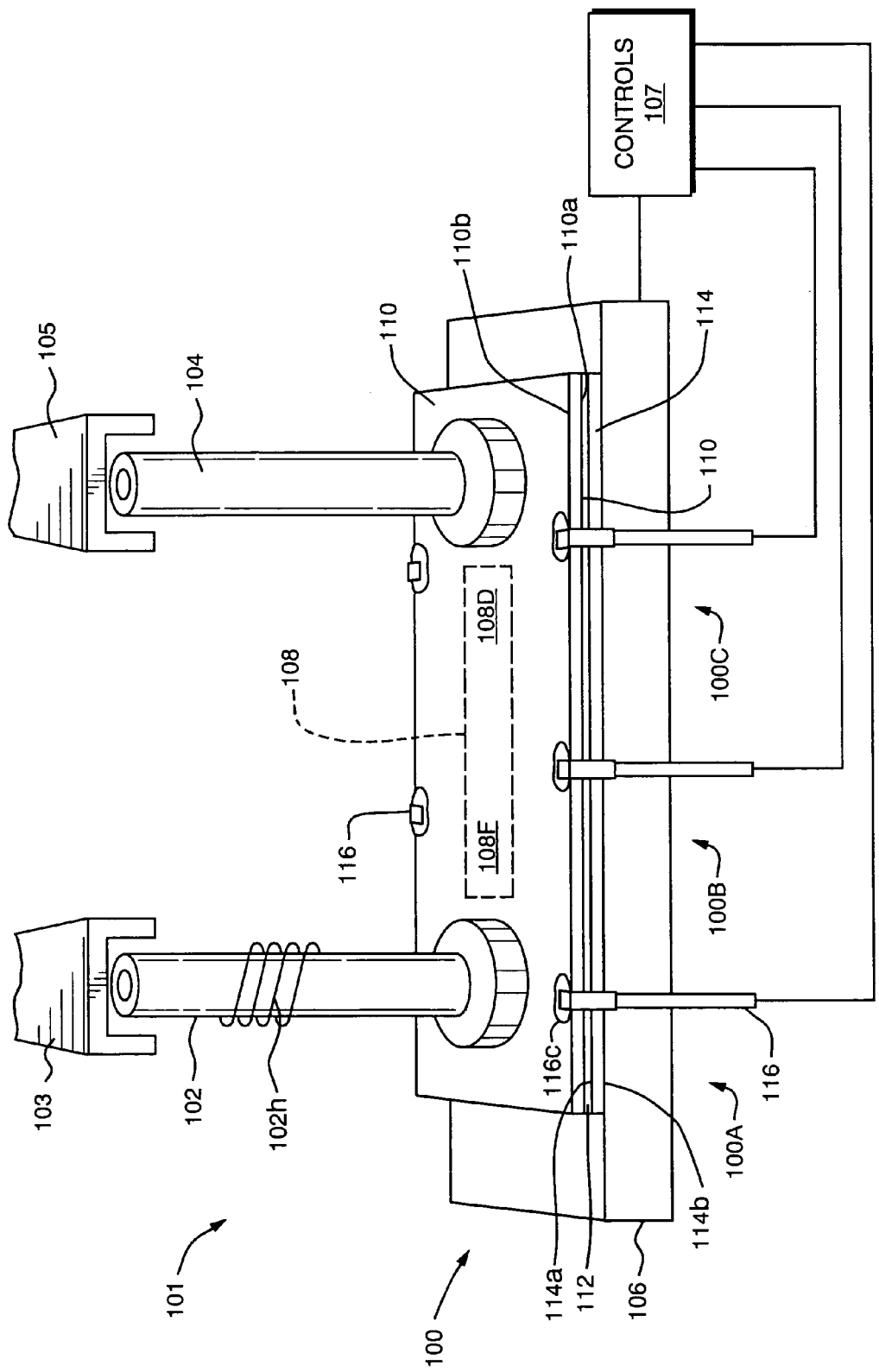
FIG. 8(a) is a schematic of an preferred embodiment of the invention.
Figure 8E:
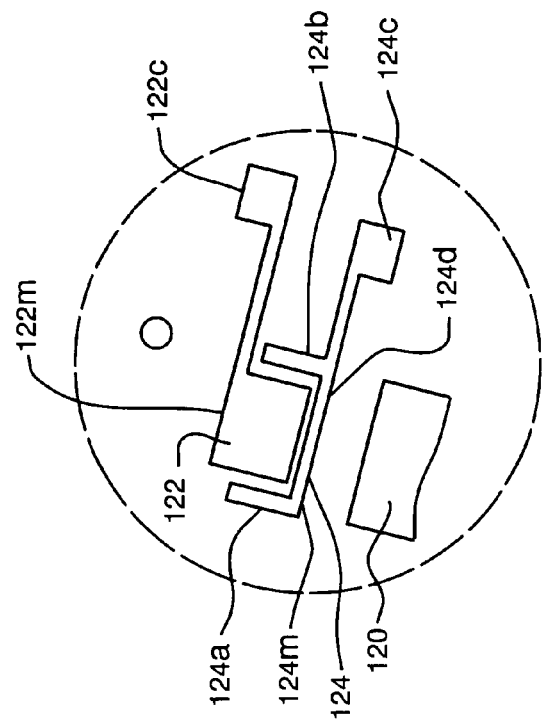
FIG. 8(e) is an expanded view of a shielded detector electrode in practice of the invention.
Figure 8B:
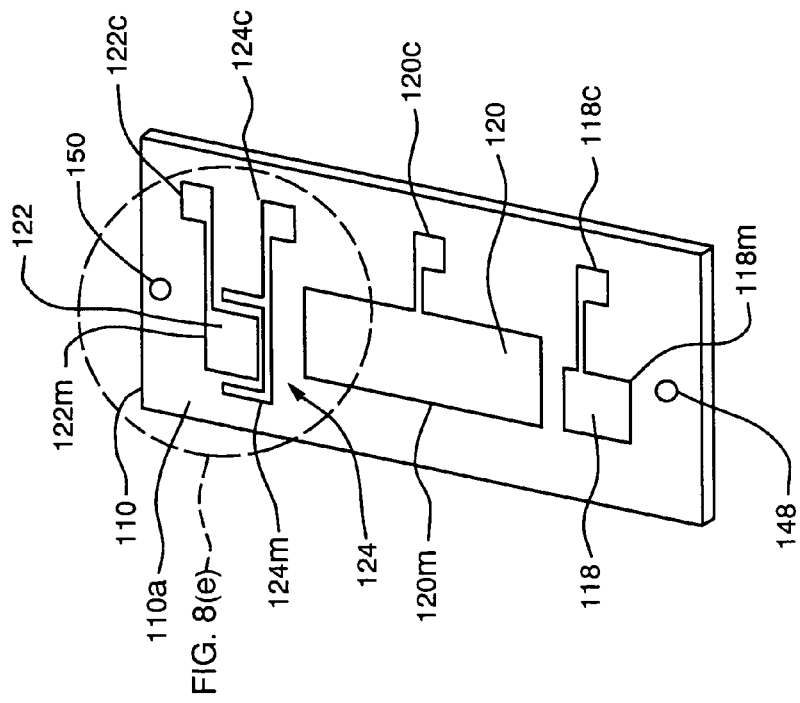
FIG. 8(b) is a perspective view of a substrate with electrodes in practice of the invention.

A preferred PFAIMS spectrometer system 101 is shown in FIG. 8(a) with chip assembly 100 defining an I/O section, a PFAIMS section 108 and a control section. The I/O section includes an inlet tube 102 for receipt of a gas sample from the environment (or from a GC outlet 103 or the like), and an outlet tube 104 which may be coupled to a pump 105 for exhaust of the air flow. Chip 100 is mounted directly to a substrate or preferably into socket 106, which may be a conventional DIP or a custom socket, for off-board connection of the chip, such as for communication with off-board drive and control electronics 107, similar to the function of section 10C discussed above.

Spectrometer system 101 functions similar to that of system 10 described above, wherein the flowing sample is ionized in the I/O section and is filtered in the filter section 108 according to the high field asymmetric waveform ion mobility method described above. PFAIMS section 100B preferably includes a PFAIMS filter 108F and also detector 108D (indicated by dotted box 108 on the face of chip 100 in FIG. 8(a)). The filtered ions are delivered to a detector, which is preferably onboard, such as detector 108D. The detected ions result in a detection signal that is processed by control electronics 107 for reporting of detected ions. More specifically, system 101 is controlled and ion detection signals are evaluated and reported by the controller section.

The spectrometer chip 100 has electrical connectors, such as leads 116, or at least bonding pads 116c, enabling connection to off-board controls, if the controls are not on-board the chip.

Figure 8F:
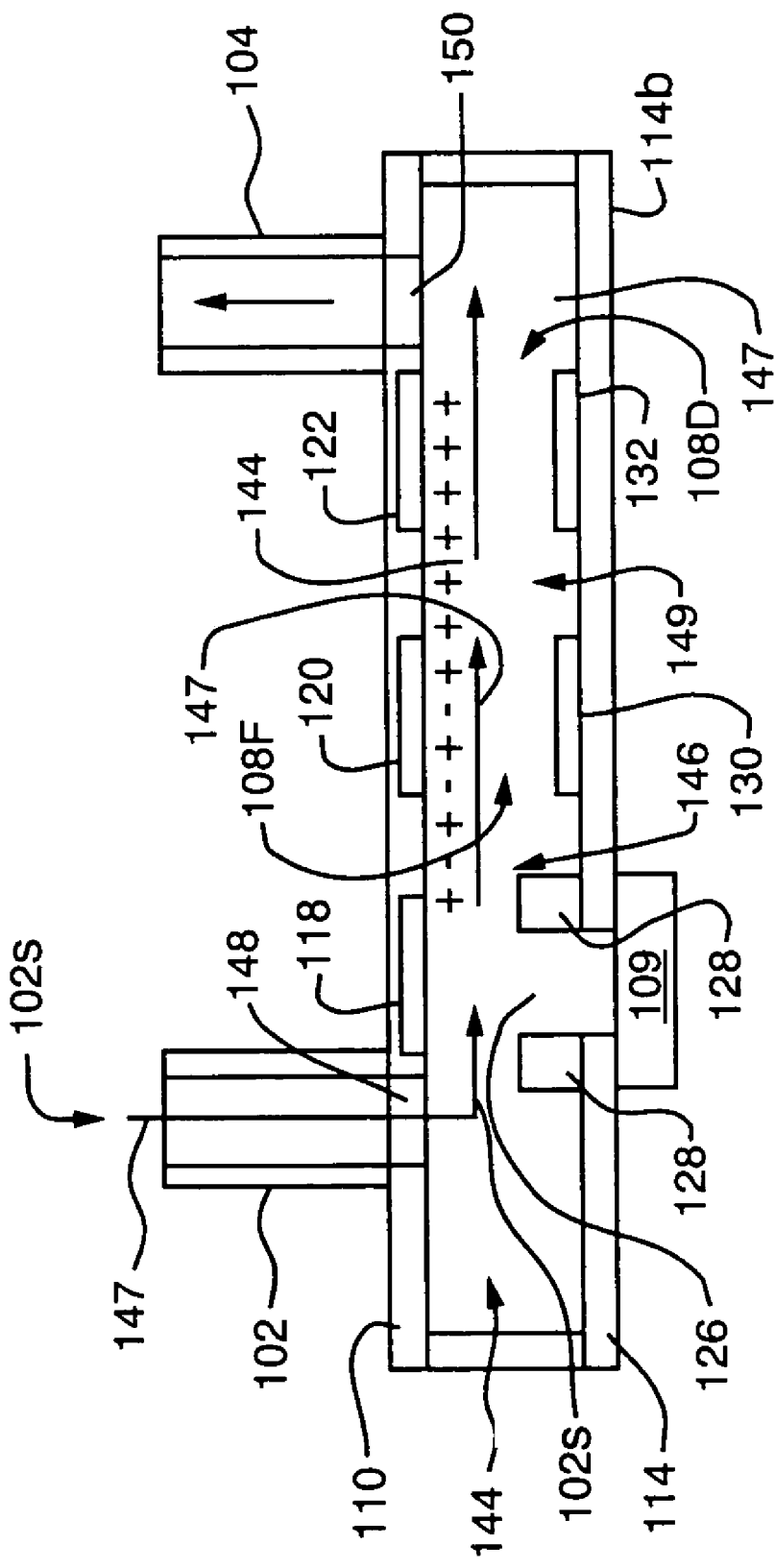
FIG. 8(f) is a side view of substrate with electrodes in practice of the invention.

An ionization source 109 is integrated with or within chip 100 (e.g., source 109, FIG. 8(f)) to ionize the sample in the gas flow from inlet 102, which is drawn through the PFAIMS section 108 by pump 105, under direction of drive and control electronics 107, similar to the function described above for chemical sensor system 10.

Ionization source 109, such as an ultra violet photo-ionization lamp, a radioactive source, or the like, converts the gas sample into a mixture of ion species with each ion type corresponding to a particular chemical in the gas sample. The ion species are then passed through ion filter 108F where the applied electric fields between the filter electrodes selects an ion type that is allowed to pass through the filter. Once through the filter, the ion is detected in detector 108D and produces an electrical signal. To detect a mixture of ion species in the sample the electric fields applied between the filter electrodes can be scanned over a range and a spectrum can be generated.

Preferably chip 100 includes a planar ceramic substrate 110 and planar ceramic substrate 114, either of which can be a top or bottom substrate. These substrates are separated by a spacer frame 112, FIG. 8(d), also preferably ceramic. Substrates 110 and 114 and spacer frame 112 are sealed together to form a hermetically sealed housing 115 (see FIG. 8(g)) on which the inlet tube 102, outlet tube 104, ion source 109 and electrical leads 116 are mounted. While a particular pinout is shown in FIG. 8(a) for mounting in socket 106, alternative configurations are possible, all within the scope of the invention.

In the embodiment of FIG. 8(a), inlet tube 102 and outlet tube 104 are mounted to the back surface 110b of substrate 110. The inner working surface 110a of substrate 110 and inner working surface 114a of substrate 114 include metalization patterns that define operation of the PFAIMS filter. These patterns result from forming electrical conductors, such as by screen printing electrodes, or by masking and etching a metalization layer, or other techniques of applying a conductive circuit. After processing the substrate surfaces, differing metalization (or metalized) sections (or segments or portions) remain with functions described below.

Figure 8G:
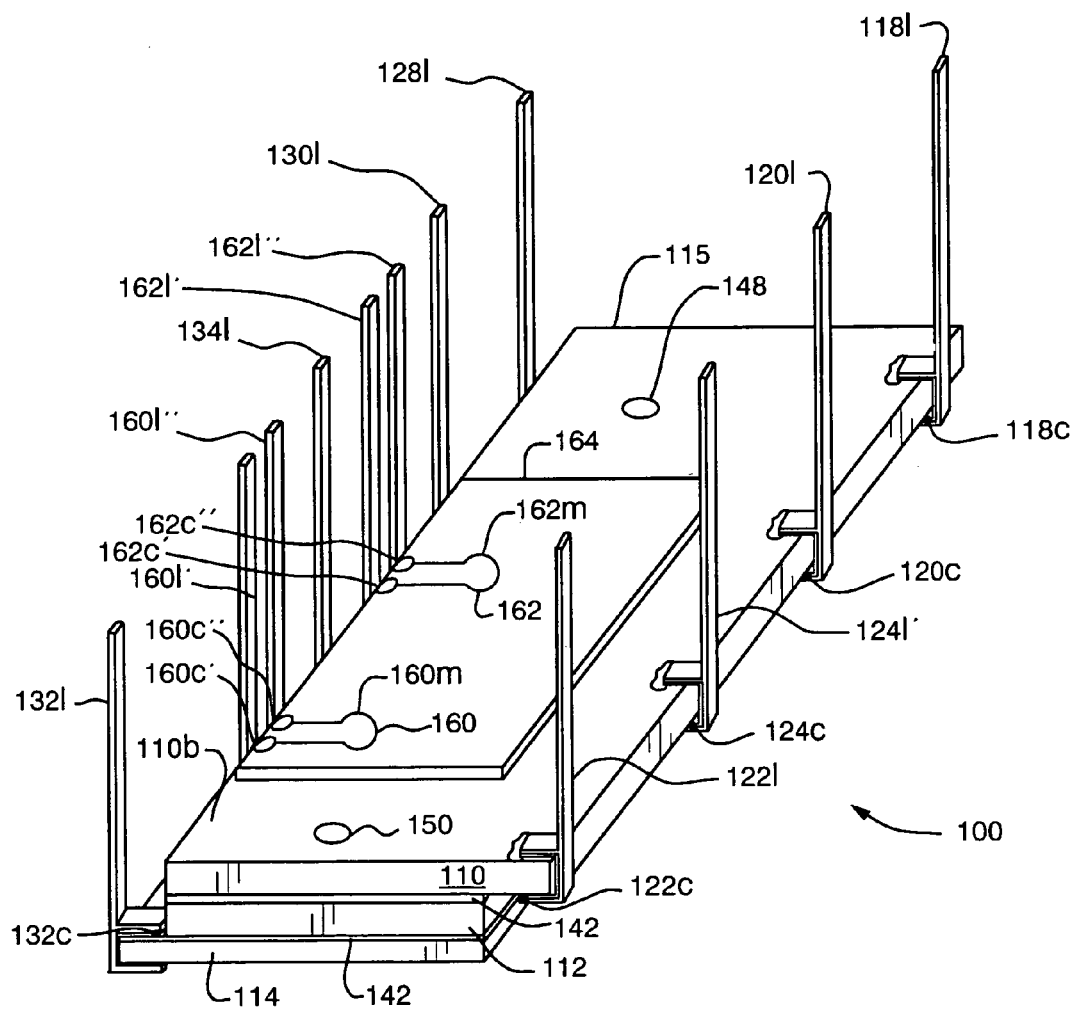
FIG. 8(g) is a perspective view of an assembly in practice of the invention.

In FIGS. 8(a–g), substrate 110 includes first metalization portion 118m that defines attraction electrode 118 and its extension that forms bonding pad 118c to which a lead 118l (shown in FIG. 8(g)) is attached. Substrate 110 further includes second metalization portion 120m that defines filter electrode 120 and its extension that forms bonding pad 120c to which a lead 120l is attached. Substrate 110 also includes third metalization portion 122m that defines detector electrode 122 and its extension that forms bonding pad 122c to which a lead 122l is attached.

First substrate 110 includes fourth metalization portion 124m that defines shielding electrode 124 and its extension that forms bonding pad 124c (to which a lead 124l will be attached). Shielding electrode 124 further defines shields 124a, 124b, 124d which shield detector electrode 122 from the filter signals, thus reducing leakage current between the ion filter 108F and detector electrode 122 of detector 108D and thus reducing noise in the ion detection signal.

An ionization access port 126 (a via or through hole) is defined in either or both substrates to enable ionization sources 109 to interact with the sample. Source 109 is shown mounted on the back side 114b of substrate 114 in FIG. 8(f), in one embodiment. As shown in FIG. 8(c), the front side 114a of substrate 114 includes first metalization portion 128m, through which port 126 extends, and defines an attraction electrode 128 and its extension that forms bonding pad 128c to which a lead 128l is attached, shown in FIG. 8(g).

Substrate 114 further includes second metalization portion 130m that defines filter electrode 130 and its extension that forms bonding pad 130c to which a lead 130l is attached. Substrate 114 also includes third metalization portion 132m that defines detector electrode 132 and its extension that forms bonding pad 132c to which a lead 132l is attached.

Substrate 114 also includes fourth metalization portion 134m that defines shielding electrode 134 and its extension that forms bonding pad 134c to which a lead 134l is attached. Segment 134m further defines shields 134a, 134b, 134d which shield detector electrode 132 from the filter signals, thus reducing leakage current between filter 108F and detector electrode 132 and thus reducing noise in the ion detection signal.

Spacer (or spacer frame) 112 is preferably a single planar strip of ceramic with a through slot which defines a drift channel 140. Drift channel 140 is contained within frame extensions 112a and 112b.

Referring to FIG. 8(g), planar substrate 110 is placed on one side of spacer 112 with bonding agent 142 (e.g., glass frit or epoxy) in between, and planar substrate 114 is placed on the other side of spacer 112 with bonding agent 142 in between. The workpiece is processed to set the bonding agent.

Use of glass frit as a bonding agent, as well as use of ceramic substrates and spacer, is preferred because these materials are inert, relatively impervious to contaminants, can withstand high heat, do not outgas, and make for rugged and robust structures. Also advantageously, substantial regularity and evenness of seal dimensions can be achieved with glass frit, which is beneficial in producing the spectrometer chip with precisely positioned substrates with a precise separation gap. All of this leads to a highly reproducible spectrometer chips in practice of the invention with predictable characteristics even in high volume manufacture.

This structure forms the basic chip assembly 100 and defines an enclosed and hermetically sealed flow channel 144. The flow channel is accessed at one end 140a by, and is in communication with, inlet tube 102 mounted over port (or through hole) 148 in substrate 110. The flow channel 144 is vented at the other end by, and is in communication with, outlet tube 104 mounted over port (or through hole) 150 in substrate 110.

Gas sample 102s is introduced into flow channel 144 via inlet tube 102, and then passes into ionization region 146 and is subjected to the ionization source 109. Source 109 emits ions that pass through port 126, guided by a bias applied to guiding electrode 128 (e.g., a positive bias for a positive ion) and attracted by attraction electrode 118 into the flowing sample 102s. The attraction electrode is driven by an attraction bias (e.g., a negative bias for a positive ions). The ions ionize compounds in sample 102s creating ions ("+","–") that are carried in the carrier gas flow 147 between electrodes 120, 130 of filter 108F, where the ions are subjected to high field asymmetric waveform ion mobility techniques (as described earlier), and filtered (selected) ions ("+") pass through the filter and are detected at electrodes 122, 132 of detector 108D. The carrier gas flow then vents from the flow channel 144 at outlet 104.

As will be appreciated by a person skilled in the art, flow channel 144 may be at, above or below ambient pressure. In some applications, the carrier gas and sample flow is generated by higher pressure at the inlet, such as produced when eluting samples from a GC, and the sample is carried along the flow channel thereby. In another application, the flow is generated by a pressure gradient at the detector, such as at the inlet of an MS and the gas is drawn thereby. The gas flow may also be generated by a pump 105 at outlet 104, FIG. 8(a).

FIG. 8(g) is a variation of the embodiment of chip 100 of FIG. 8(a) having the leads extending upward, but otherwise is the same but for the addition of optional heater elements 160, 162. More particularly, surface 10b of substrate 110 includes metalization portion 160m that defines heater element 160 and its extension that forms bonding pads 160c' and 160c" to which lead 160l' and 160l" are attached. Substrate 110 further includes metalization portion 162m that defines heater element 162 and its extension that forms bonding pads 162c' and 160c" to which leads 162l' and 162l" are attached. These heaters are preferably coated with an insulating thermally insulating layer 164 (drawn transparent in the figure) to trap the generated heat within the chip. These optional heaters may be actuated by control circuit 107 for heating the flow channel for purging neutralized ions and for maintaining an operating temperature, as needed. The entire assembly may be encapsulated in this thermally insulating material.

In an alternative method, the gas sample 102s is preheated such as by a preheater 102h (see FIG. 8(a)), to achieve a well-defined operating temperature, to reduce clustering and to reduce moisture effects.

Figure 8H:
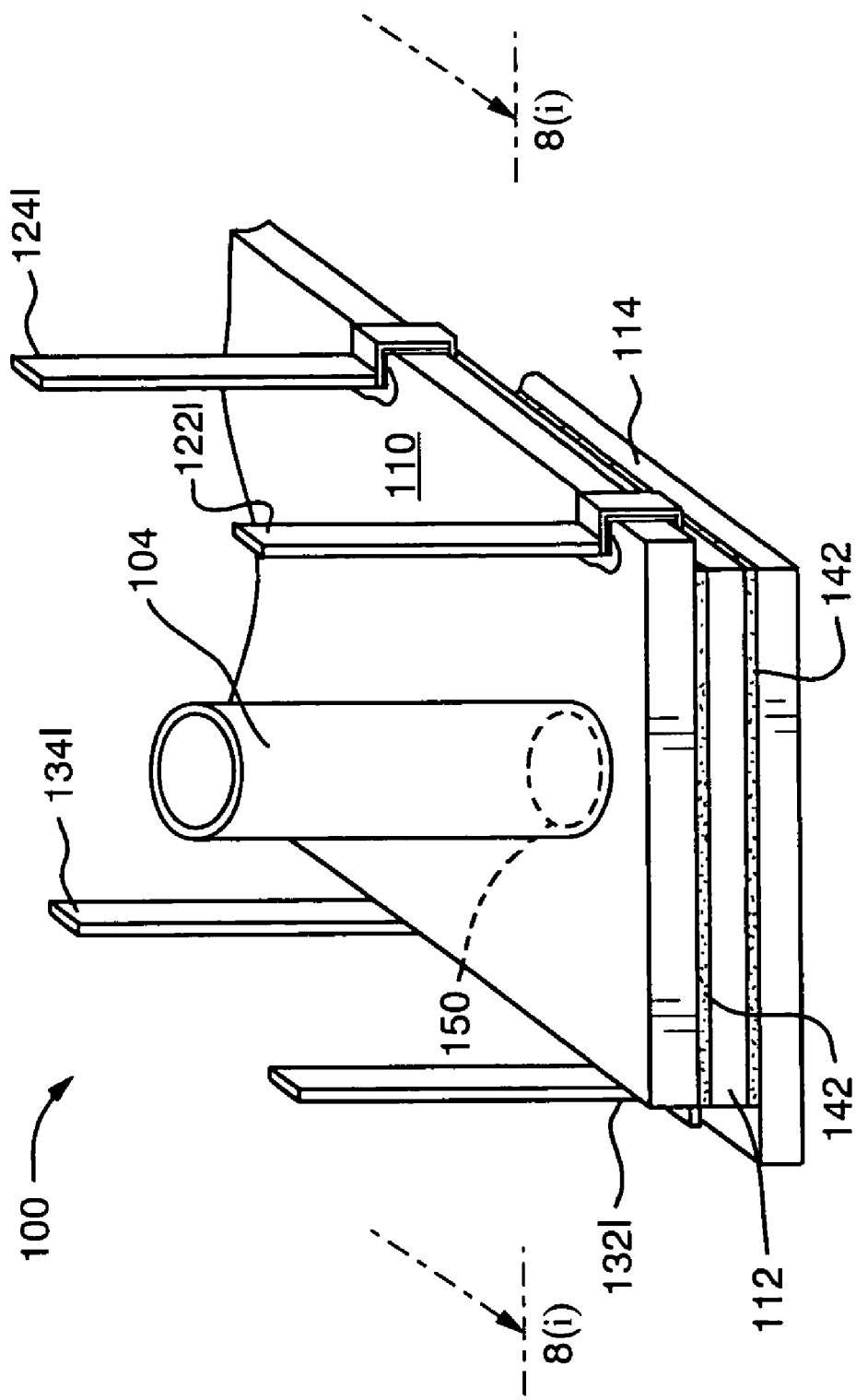
FIG. 8(h) is a partial view of the assembly of FIG. 8(g) with input tube in practice of the invention.

FIG. 8(h) shows a segment of chip 100 with outlet tube 104 mounted over outlet port 150. FIG. 8(i) is a sectional view taken along line i—i of FIG. 8(h) showing metalization section 122m on the inner side 110a of substrate 110 and showing metalization section 132m on the inner side 114a of substrate 114, with the trapped and sealing-making bonding agent 142, and showing outlet port 104 in the background.

Figure 8J:
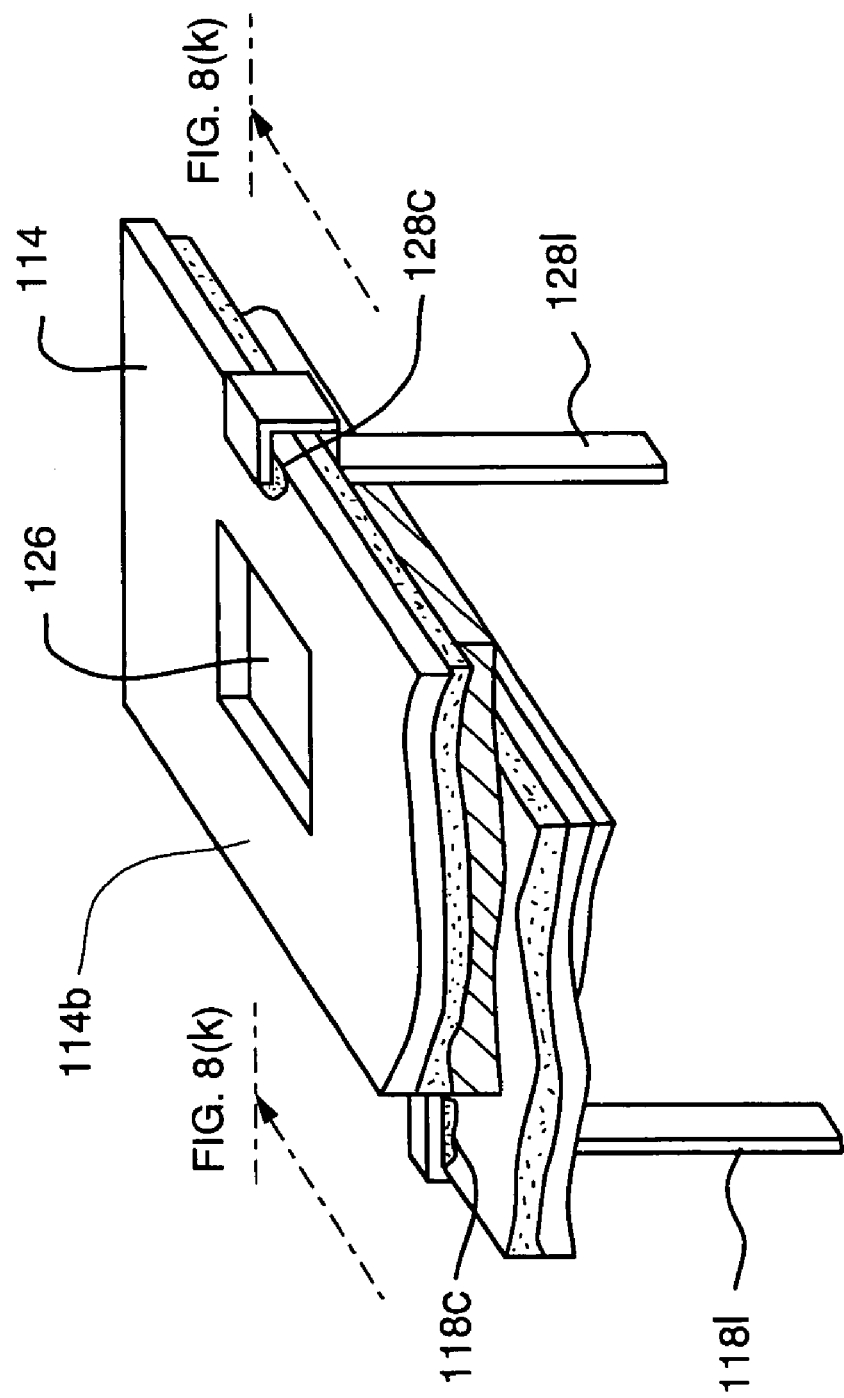
Figure 8K:
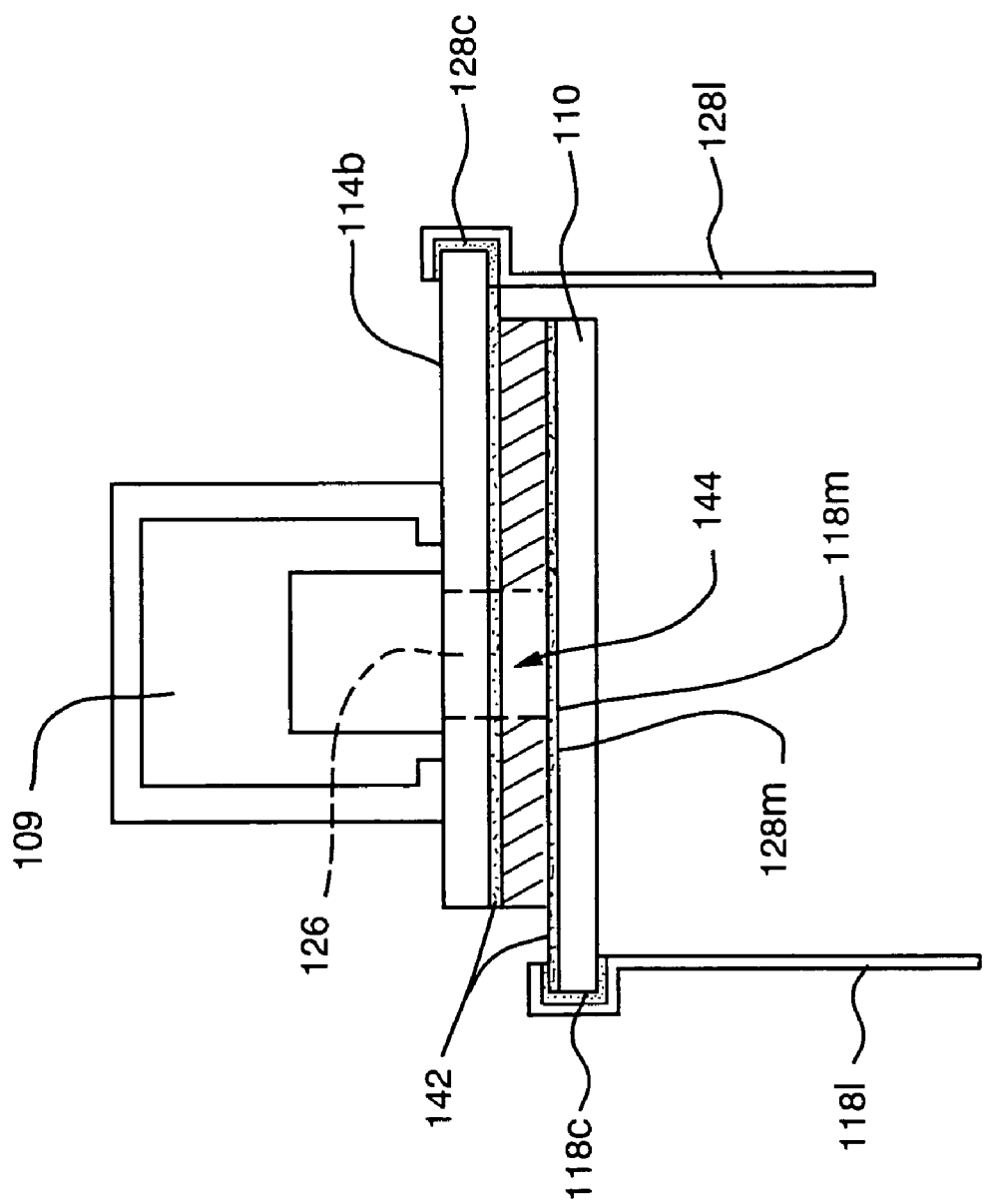
FIG. 8(k) is a cross-sectional view taken through line k—k of FIG. 8(j) in practice of the invention.
Figure 8L:
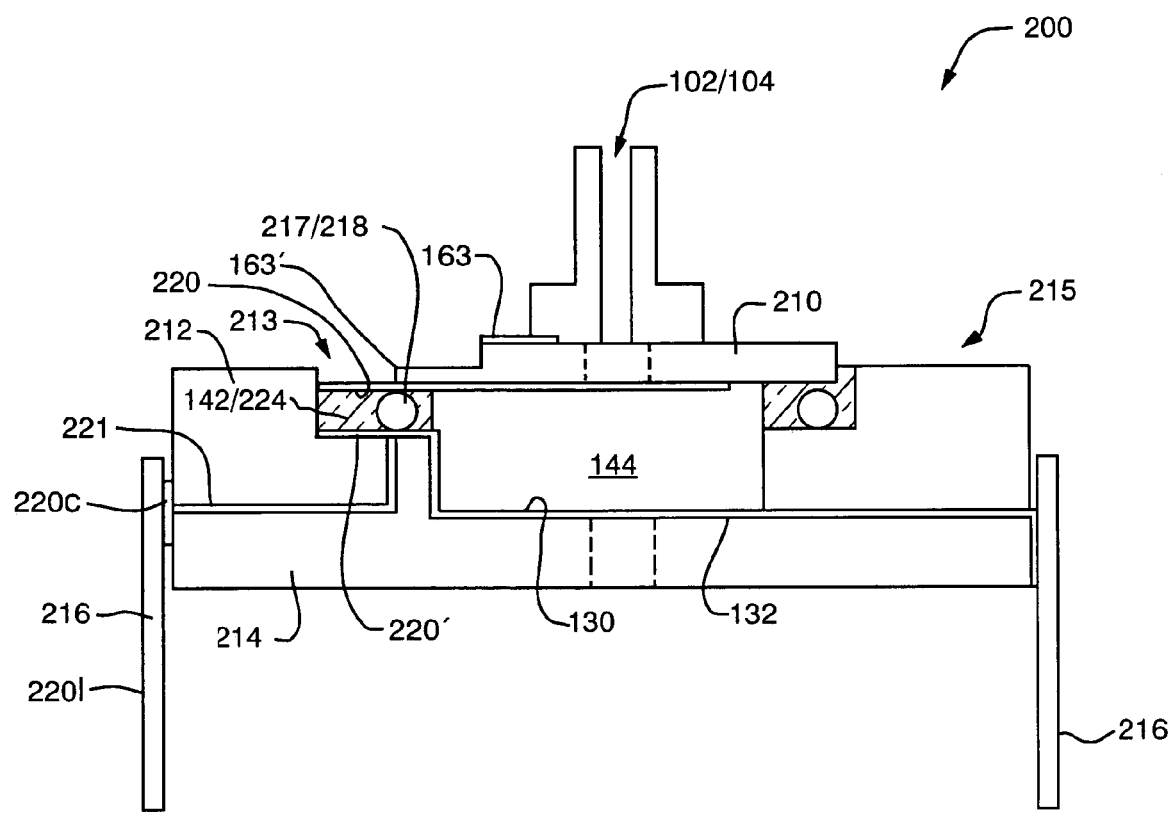
FIG. 8(l) is a side cross sectional view of a chip assembly in practice of the invention showing a double-sided circuit board substrate and electrical connection from one substrate to another through the spacer part.
Figure 8M:
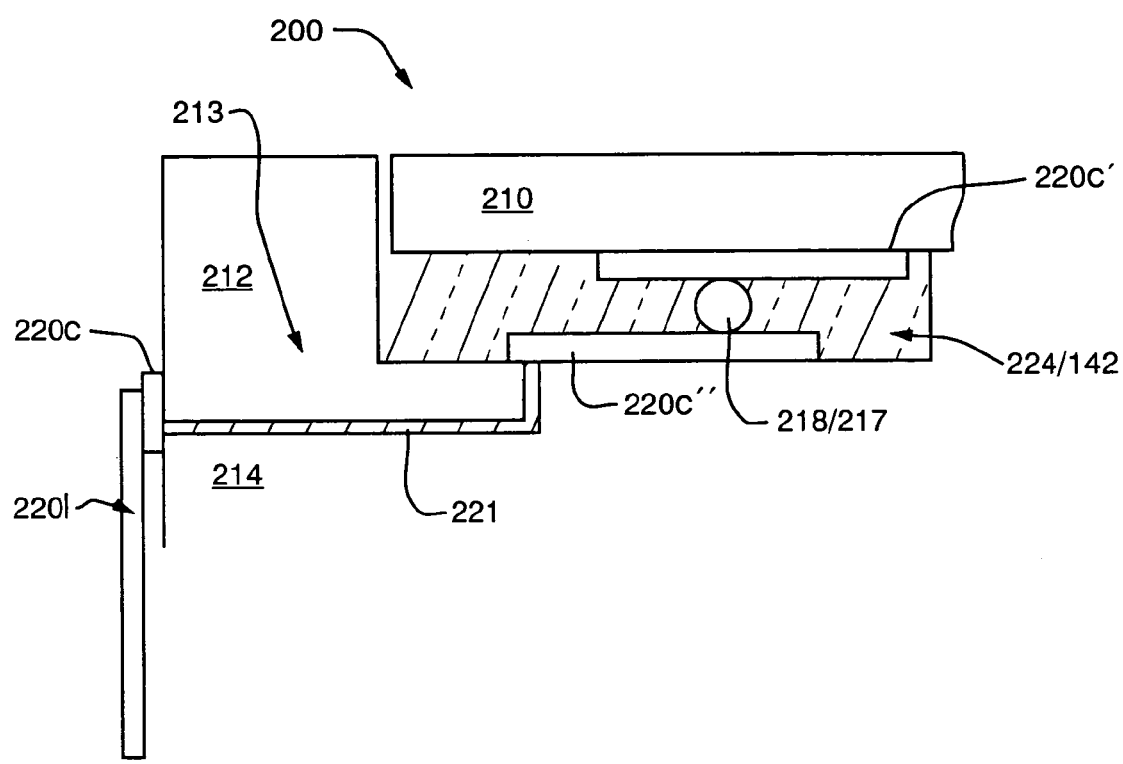
FIG. 8(m) is a partial detail side-cross sectional view of the chip assembly of FIG. 8(l) in practice of the invention.
Figure 8O:
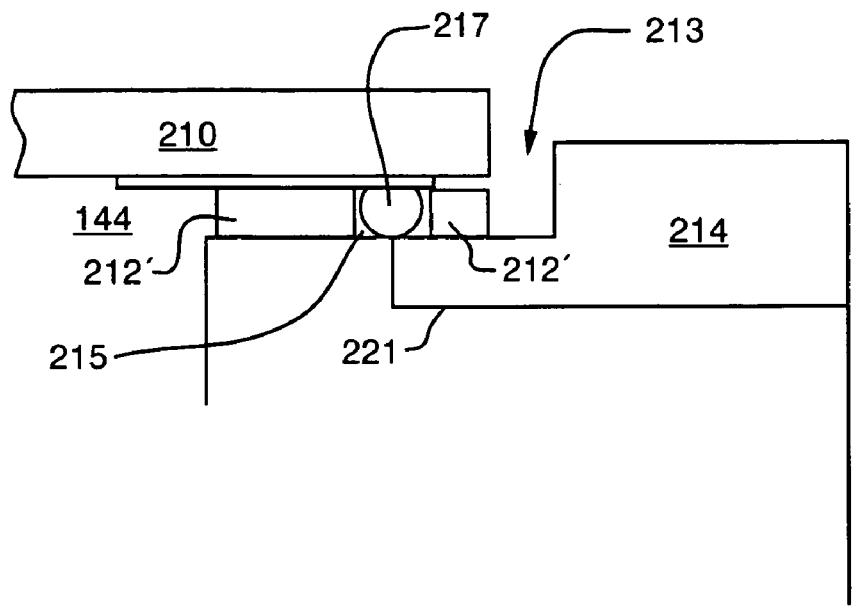
FIG. 8O) is a partial view of the under side of the assembly of FIG. 8(g) in practice of the invention.
Figure 8P:
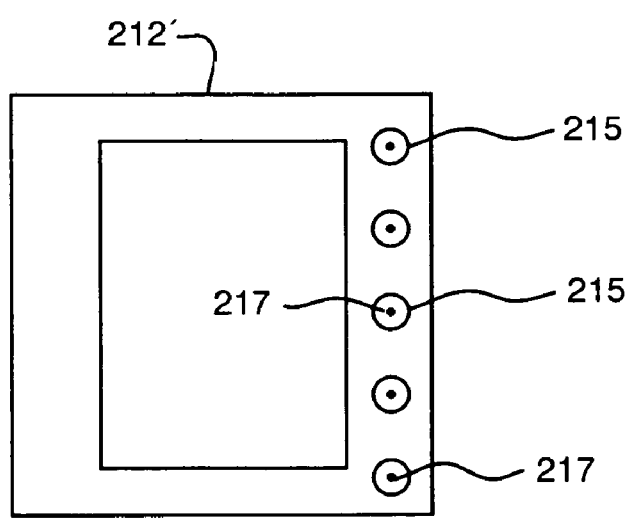
FIG. 8(p) is a plan view of a spacer frame in practice of the invention.

FIG. 8(j) shows a segment of chip 100 rotated 180 degrees and showing the bottom surface 114b of substrate 114 with ionization port 126 exposed. FIG. 8(k) is a sectional view taken along line k—k of FIG. 8(j) showing metalization section 128m on the inner side 114a of substrate 114 and showing metalization section 118m on the inner side 110a of substrate 110, with the trapped and sealing-making bonding agent 142, and showing ionization source 109 in direct communication with flow channel 144 via port 126.

Spectrometer chips in practice of the invention may be manufactured using thick film or other processes. In one preferred embodiment, chip 100 is manufactured using a "green tape" co-fired ceramic process to generate an integrated circuit-like chip 100. The fabrication process begins with an unsintered flexible ceramic tape (made mostly of alumina) which is cut into sheets. Holes are punched in the sheets and selective holes are filled with metal to form vias. Metal electrodes can be screen printed on the top surface of each green tape sheet. Multiple sheets are aligned, stacked, and then laminated together. The sheets are cut into individual subassemblies and these are then co-fired, producing a tough, impervious package.

In embodiments of the invention shown in FIGS. 8(l–n), a chip assembly 200 is fabricated as a multilayer co-fired package, where the lower substrate 214 and spacer 212 are bonded together to form a socket or receiver assembly 213. Substrate 210 is mounted into receiver assembly 213. The bonding pads on substrate 210 are mated with bonding pads on the receiver assembly 213, ultimately to run out to leads, e.g., 216 and 220.

The flow channel results when the three co-fired pieces are bonded together and an entire chip assembly 200 or housing 215 is created. The substrates are preferably formed as planar ceramic parts. Substrate 214 includes the ion filter electrode 130 and detector electrode 132 described above, and may include a heater electrode. In one embodiment, the spacer 212 is 0.5 mm thick planar co-fired ceramic and forms the flow channel side walls while acting as a spacer to provide the gap between the ion filter electrodes. The spacer and bottom substrate are bonded together (preferably using glass frit, or epoxy) and then the planar co-fired ceramic top substrate 240 is bonded to the receiver 213 to form the enclosed flow channel 144 and chip 200. In one embodiment, the inlet 102 and outlet 104 tubes are affixed to the top of substrate 210 before the assembling and bonding.

The electrode structure discussed with respect to chip 100 may also be applied to chip 200. In an illustrative embodiment, substrate 210 will be understood as equivalent to substrate 110, substrate 214 to substrate 114 and spacer 212 to spacer 112, except for differences noted below.

For example, connection to lead 2201 for upper substrate filter electrode 220 is made by making connection between bonding pad 220c' of upper substrate 210 to a bonding pad 220c" on the upper surface of receiver 213, which directly connects to lead 220l through via 221 and contact 220c. In one practice of the invention, a solder ball 218 is loaded at the connection point between bonding pad 220c' and 220c" surround by a sea of glass frit 224. Upon heating, the glass frit forms a hermetic seal like layer 142 while the molten solder 217 completes an electrical connection between bonding pads 220c' and 220c" and through via'd metal run 221 and contact 220c to lead 220l. (This is a process that is preferably followed at all contact locations needing electrical connection.)

In further embodiments of the invention, chip 200 is shown in FIGS. 8 (o–p) demonstrating alternative methods for attaching the upper substrate 210 and making electrical connection to the pinout on the receiver assembly 213. Upper substrate 210 has the electrode and bonding pad configuration of substrate 110. Spacer frame 212' is formed from glass tape and has punched holes 215 with a metal ball 217 (or a via hole 215 with a metal paste fill 217). This loaded spacer 212' is placed on the lower substrate 214 with a layer of bonding agent (like grass frit 224 or epoxy) in between and then another layer of bonding agent is loaded on the spacer 212' and the upper substrate 210 is loaded thereon. The assembly is heated to melt the metal balls to form electrical paths and to melt the glass frit to make a hermetic seal in forming the flow channel 144. The via'd metal run 221 and attached leads are shown as part of lower layer 214 in FIG. 8(n). (This is a process that may be followed at all contact or bonding locations needing connection.)

In another alternative embodiment of the invention shown in FIGS. 8(q and r), a spectrometer chip of the invention includes a pin grid array 214PGA. Spacers 212" cooperate with substrate 214' to provide electrical connection of the second substrate 210 to assigned pins of array 214PGA.

Figure 8Q:
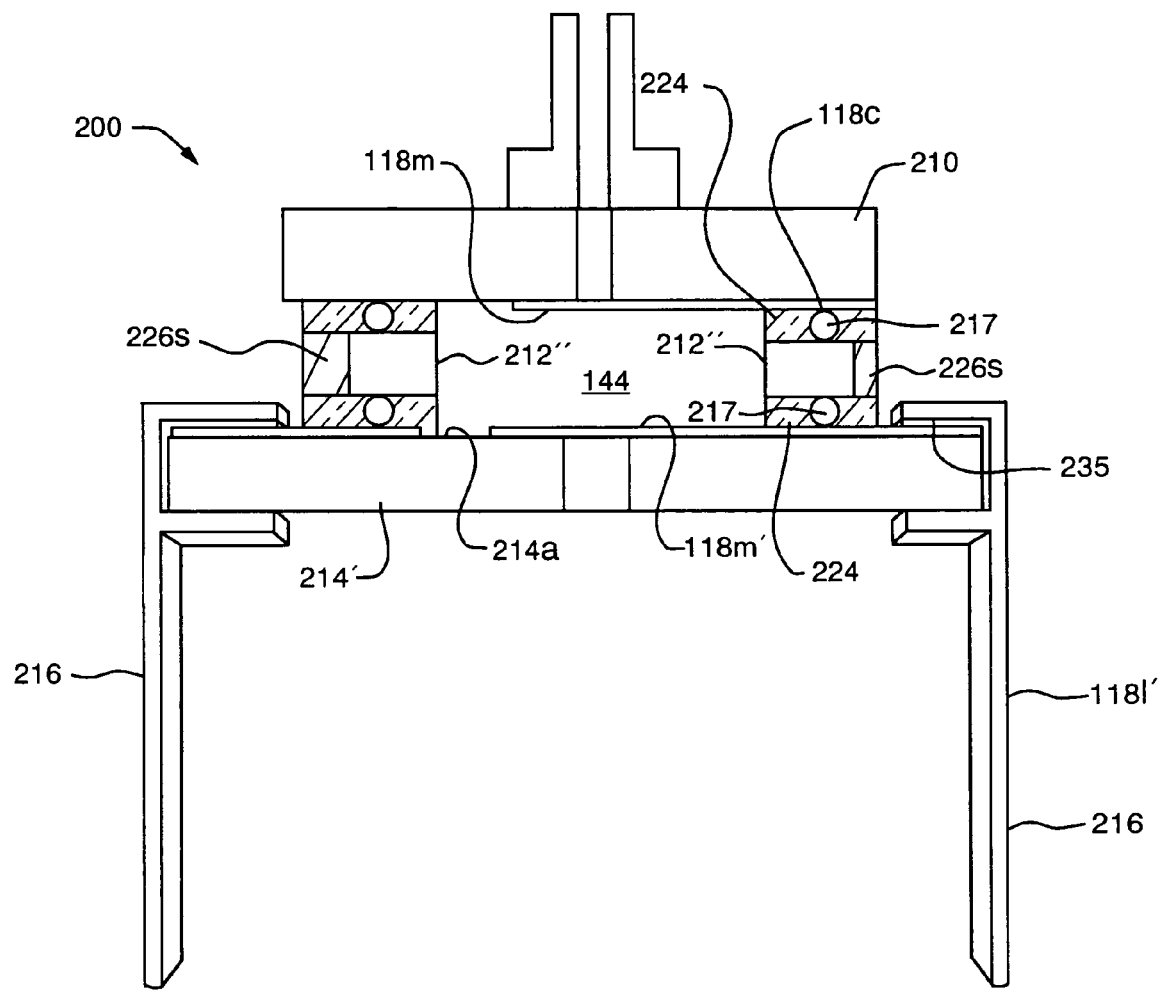
Figure 8R:
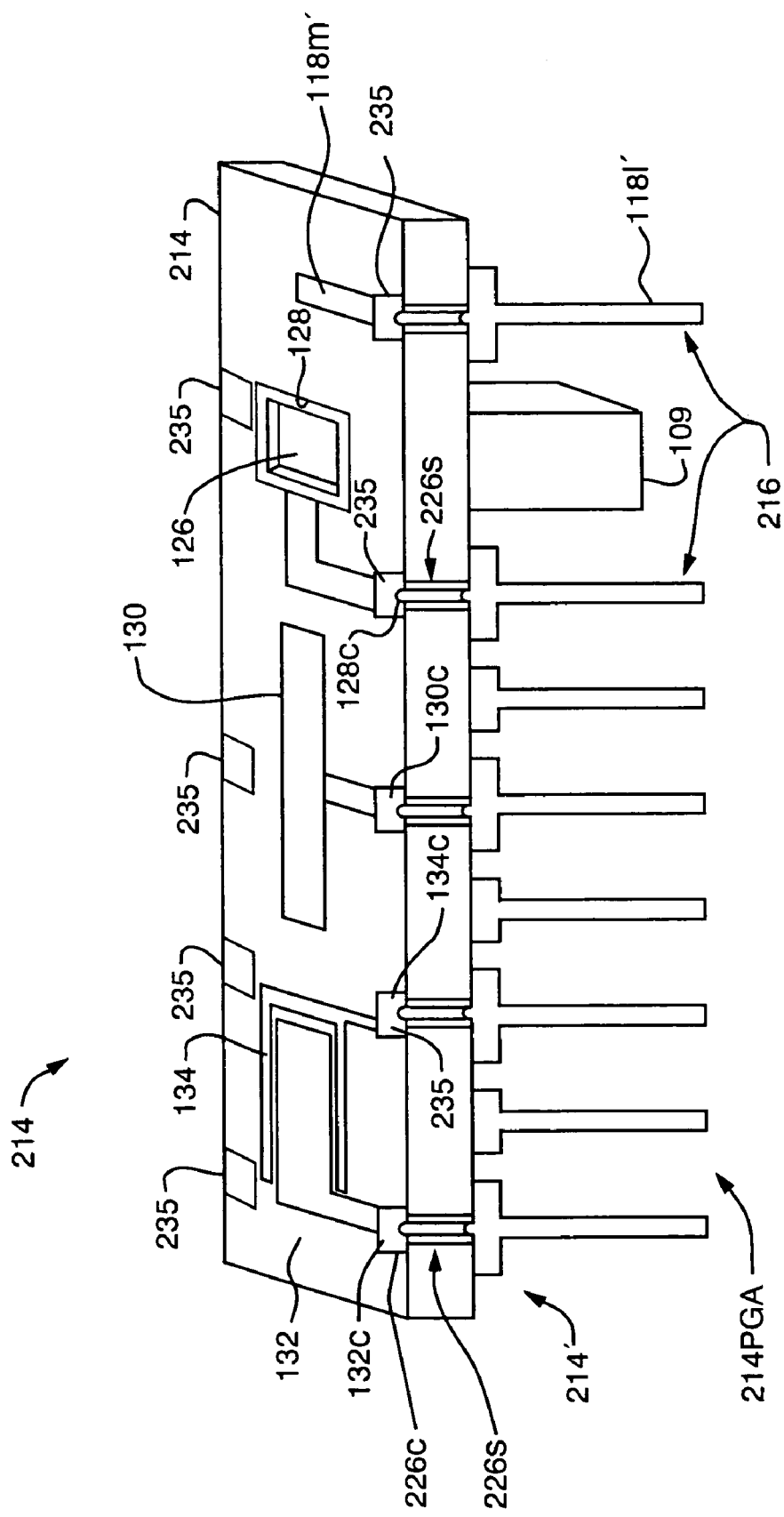
FIG. 8(r) is a perspective view of a chip assembly in practice of the invention.
Figure 8W:
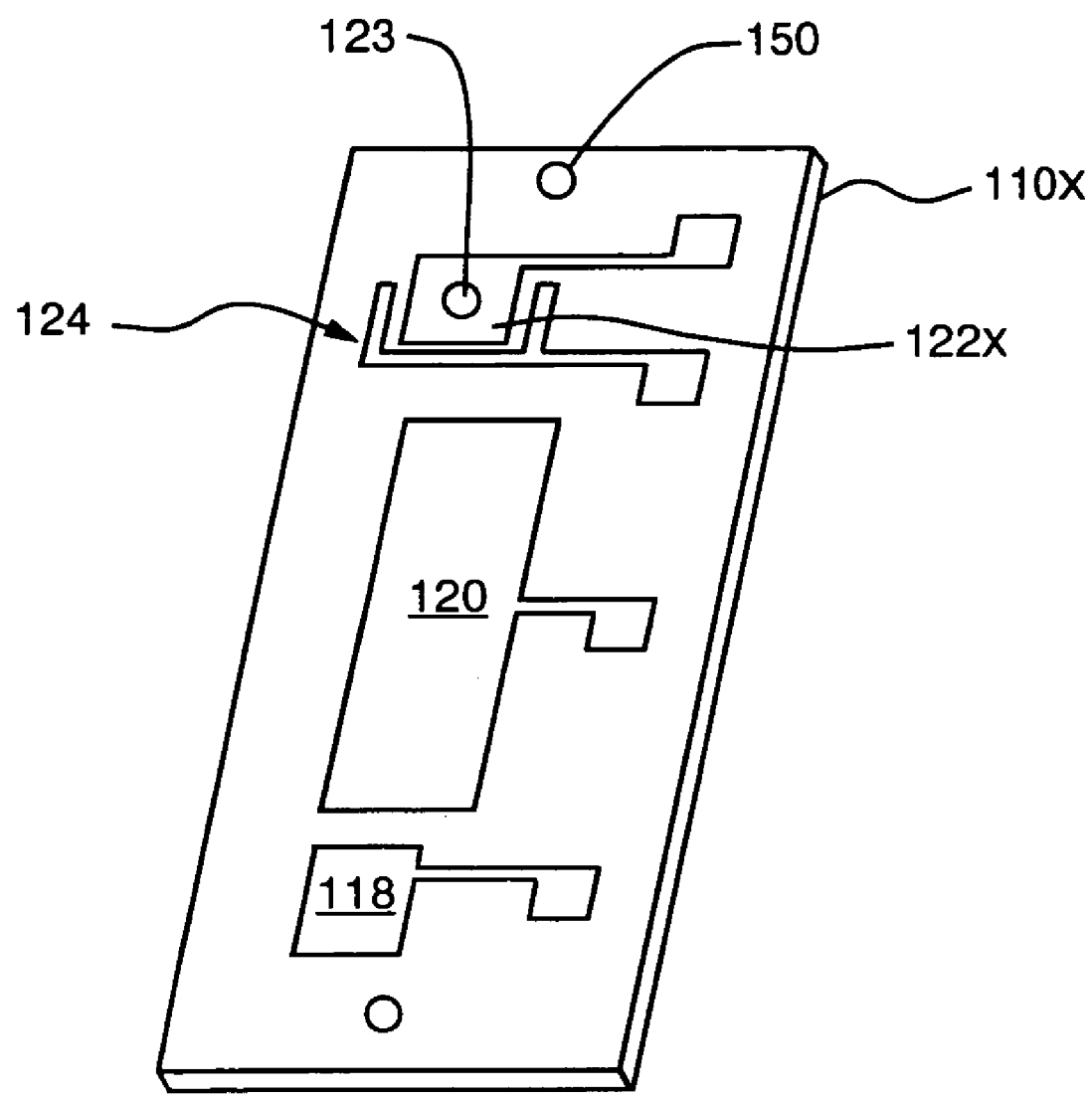
FIG. 8(w) is a perspective view of a substrate with electrodes and detector outlet port in practice of the embodiment of FIG. 8(v).
Figure 8X:
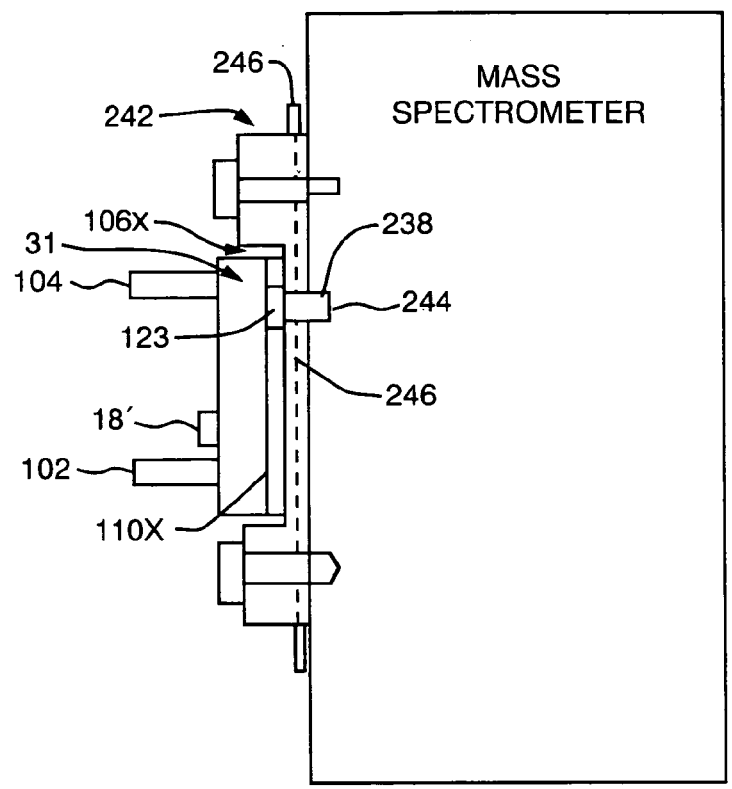
FIG. 8(x) is a side view of the embodiment of FIG. 8(v) mounted to a mass spectrometer.
Figure 8Y:
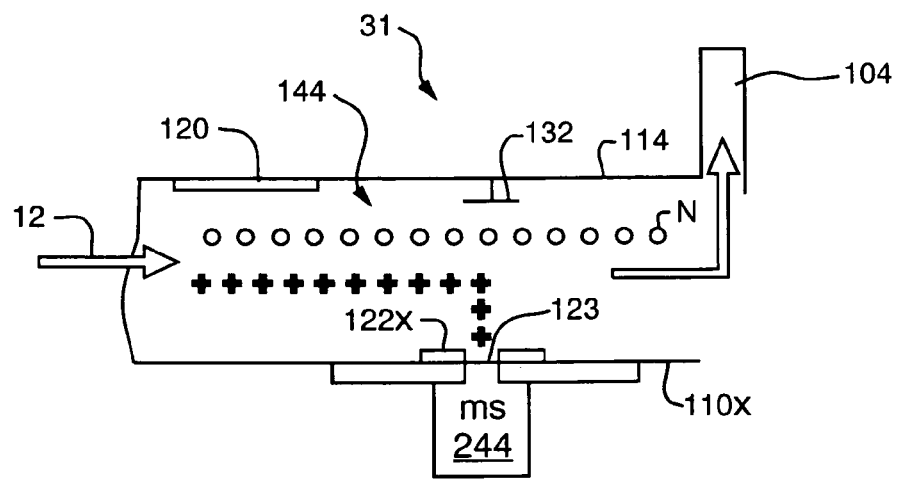
FIG. 8(y) is a schematic showing ion flow in the output region in the embodiment of FIG. 8(v) in practice of the invention.

In production of one embodiment of spacers 212, a die 212D is formed from insulating material and forms a plurality of spacers 212", each with a defined spacer channel 144, as shown in FIG. 8(s)(1–2). Die 212" has dicing lines 225 running through a series of vias 226, separating spacers 212". Each via is metalized with a metal conductor 226c to form a metalized sidewall 226s. Die 212D is diced and the result is a spacer 212" with metalized sidewall vias 226s. In FIG. 8(q) spacer 212" is placed on lower substrate 214 along with solder balls 217 and glass frit 224 and baked. In another embodiment, the pin grid array is formed as part of spacer 212 rather than as part of one of the substrates.

Referring now to the embodiments of FIGS. 8(q–r), upper substrate 210 has the electrode and bonding pad configuration of substrate 110 and lower substrate 214' has the electrode and bonding pad configuration of substrate 114 and also has additional bonding pads 235. The spacer has vias or castellations to provide electrical connection from one side of the spacer to the other, thus to enable communication from one substrate to the other through the spacer. The spacer is thus a mechanical separator, forming sidewalls of the device, a precision locator of the substrates that must face each other precisely across a gap established by the spacer, and an electrical connector or bridge enabling electrical communication through the spacer.

As shown in FIG. 8(q), upper substrate 210 is placed on spacer 212" with its bonding pads contacting metalized sidewalls 226s of the spacer 212" directly or with addition of solder ball bonding, and addition of sealing, preferably glass frit. After heating, the upper substrate is in communication with pins 216 on lower substrate 214'. For example, attraction electrode 118 on metalization portion 118m of upper substrate 210 presents bonding pad 118c for pinout. Bonding pad 118c couples to lead 118l' by way of the metalized path 226s of spacer 212" and metalization layer 118m' on lower substrate 214'. (This is a process that is followed at all contact or bonding locations needing connection such that conductors 226s on spacer 212" connect to bonding pads 235 on the lower substrate 214' for communication to leads 216, such as shown for lead 118l').

Additional items, such as circuit components and elements, may be formed on the outer surfaces of the substrates or spacer. For example, heater element 163 is shown in FIG. 8(1) formed on the outer surface of substrate 210, and having a via'd metal run 163' (for coupling to an assigned pinout not shown).

In a reduced-parts-count embodiment of the invention shown in FIG. 8(t)(1–2), substrate 210' is mounted to a combined spacer-substrate assembly 236. Assembly 236 defines integral spacer walls 236b and substrate 236a. Metalization patterns are formed on the substrates as needed. The lower surface 210a of upper substrate 210' (including metalization if present) is bonded with glass frit or the like to the top surface 236b' of the sidewalls 236b to form a hermetically sealed flow channel 144.

In a preferred embodiment, the spacer walls 236b cooperate with the substrates to define a flow channel 144', with the spacer walls 236b extending over the edges of the electrodes. For example, as shown in FIG. 8(t)(1), the spacer walls 236b form borders 236bx that overlap the sides of electrodes 128', 130', 132' and 134'. The effect of this overlap is to force all of the flowing sample and ions to pass over and between the electrodes, as well as reducing the flow channel volume. This assures that all ions are filtered and do not by-pass the filter.

Also, this reduced volume in turn reduces the required volume of carrier gas, without noticeable reduction in the volume of sample that can be carried. This smaller volume results in higher sample-to-carrier-gas ratio leading to higher operating sensitivity and operating efficiency. The lower volume also reduces reduced power requirements.

Metalization layers terminate in bonding pads, castellations or vias as needed to be accessed by external leads 116 or the like. For example, substrate 210' includes metalization layer 120m' which defines filter electrode 120' and bonding pad 120c' and substrate 236a includes metalization layer 130m' which defines filter electrode 130' and bonding pad 130c' which passes through wall 236b for connection to lead 116 or the like.

An additional reduced parts-count embodiment 300 of the invention is shown in FIG. 8(t)(3), where substrate 310 with shoulders 310a, 310b is mated to substrate 314 with shoulders 314a, 314b. Shoulders 310a, 314a and shoulders 310b and 314b cooperate to form a spacer or spacer assembly 312, performing the spacing function described for spacers above that assures a precise gap and a parallel relationship of the electrodes facing each other in the flow channel.

In addition, these shoulders extend into flanges 310af, 310bf, 314af, 314bf. When substrates 310, 314 are joined, the flanges are mated together with bonding agent, such as glass frit 315, and form hermetically sealed flow channel 344. Lips 316a, 316b provide for accurate alignment, mating and seating of substrate 310 with substrate 314 during assembly.

The mated flanges of the mated substrates form wings 300w1, 300w2. Metalization patterns are formed on these wings to forms edge connectors 300e1 and 300e2 with pinouts as needed. For example, metalization layer 320m terminates by way of castellations or vias 320v as needed to access external bonding pad 320c, to which external electrical connection may be made by attachment of leads or preferably directly by a cooperating socket, such as socket 350 shown in FIG. 8(t)(4). As a result, a low-parts count, high performance spectrometer can be cost-effectively produced in volume in practice of the invention.

In the above embodiments, the pinouts may vary as needed. Also the inlet tube and outlet tubes may be repositioned as needed. For example, chip 200u is shown in FIG. 8(u)(1) with side-mounting inlet tube 102 aligned with the longitudinal axis A of the chip assembly and extending within the chip to be in communication with flow channel 144. This arrangement permits side coupling of inputs. Outlet 104 may be side mounted as well.

An alternative side mounting embodiment of the invention is shown in FIG. 8(u)(2)(i–iv), where the chip 200u is physically tapered to define an inlet tube 202u as a longitudinal extension 202ux of the chip substrate assembly 200*up*, extending along longitudinal axis A. Extension 202*ux* forms a coupling mechanism and may have an external detail, such as a rib 202*r*, which assists coupling to an external connector, such as for connection to a GC outlet.

The chip is also tapered to define outlet 204*u* as a longitudinal extension 204*ux* extending along axis A. Extension 204*ux* forms a coupling mechanism and may have an external detail, such as a rib 204*r*, which assists coupling to an external connector, such as connector MS1 coupled to an MS intake.

Spacer 236*u* is formed with two spacer bars 236*b*1 and 236*b*2 that cooperate with the substrates to define the flow channel 244*u*, which are mated with glass frit or the like. The spacer bars perform the function of spacer walls 236*b* (see FIG. 8(*t*)(1)) by defining the area of the flow channel 244*u* and restricting the sample flow path to be over and between the electrode surfaces, such as shown and discussed with respect to FIG. 8(*t*)(1).

Heater elements 160, 162 and contact pads 160*c* may be formed on the outer surface of substrates 210*u* and 214*u*. The heater elements are preferably covered with a thermally insulating layer 164 to trap the heat generated by the heaters within the chip. Preferably the spacer is ceramic and substrates are ceramic, with electrode configurations such as those described earlier.

The mid-section of chip 200*u* extends laterally into package wings 200*u*' and 200*u*", formed by the substrate wings 210*u*' and 210*u*" and 214*u*' and 214*u*". These wings extend laterally beyond the spacer bars 236*b*1, 236*b*2. The area defined between each set of substrate wings 210*u*' with 214*u*' and 210*u*" with 214*u*" form wing areas W1 and W2. Bonding pads, for example pads 118*c*, 128*c*, 124*c*, 134*c*, are formed on the substrates in these wing areas and form edge connectors EC1*f* and EC2*f*. Corresponding mating edge connectors EC1*m* and EC2*m* mate into connectors EC1*f* and EC2*f* to facilitate off-chip connection such as to control and driver circuits as needed.

In yet other embodiments of the invention, shown in FIGS. 8(*v*–*y*), chip 200X is provided with coupling 238 on substrate 110*x* for coupling to an external detector such as a mass spectrometer. More particularly, substrate 110*x* includes a detector outlet port 123 formed as an orifice in the substrate through detector electrode 122*x* for output of ions to the MS intake 244. As before, shielding electrode 124 guards detector electrode 122*x* from the filter signal.

Chip 200*x* is mounted directly to the MS or preferably into socket 106*x* shown in FIG. 8(*x*) as part of a receiver assembly 242 mounted over the MS intake 244 with a plenum gas chamber 246 in between.

As shown in FIG. 8(*y*), ions "+" passed by the ion filter 120 are carried in the gas flow 12 along flow channel 144 into the output region 31. Electrode 132 on substrate 114 acts as a deflector electrode, in this example, positively biased, to deflect positively charged ions "+" to outlet port 123, which then flow into MS inlet port 244 for detection. The gas flow is exhausted along with neutrals "N" at outlet tube 104.

The ions are guided or focused by guiding electrode 122*x* and pass through port 123, and plenum gas chamber 246, into the MS inlet 244. Providing a low flow rate plenum gas into plenum chamber 246 prevents neutralized sample ions or solvent molecules from entering the mass spectrometer intake 244. Ions that are focused into the mass spectrometer intake are then detected according to standard mass spectrometer procedures.

The deflector electrode 132 and guiding electrode 122*x* can also be used as detector electrodes to generate PFAIMS detection information. This information can be combined in a set of orthogonal detection data that very accurately and reliably can be used to identify detected species.

Because of the small size of chip spectrometers in practice of the invention, the chip receiver assembly 242 is relatively small and compact. Even without the benefit of socket 106*x*, mounting of the present invention to an MS is quite simplified compared to connection of prior art spectrometers to an MS.

It will be appreciated that due to geometrical and physical considerations, the ions in known prior art cylindrical designs are distributed evenly in the flow channel cross-section and therefore only a fraction of ions are available in the output region near the MS intake. One prior art configuration of a cylindrical FAIMS allows a higher degree of delivery of ions to the mass spectrometer intake, see PCT/CA99/00715, incorporated herein by reference. But the problem, however, is that neutral sample molecules can also enter into the MS intake because there is no separation between the sample ions and neutral molecules, such as solvent molecules. This leads to significantly more complex spectra in the mass spectrometer, and degraded resolution.

The present invention overcomes these shortcomings wherein virtually all of the ions "+" entering the output region 31 are focused into the MS intake 244. This results in a dramatic increase in efficiency of detection and improved sensitivity of the system.

Further variations of the above embodiments are also within the scope of the invention. For example, as shown in FIG. 8(*z*)(1–2), a chip 100*z* is formed using a circuit board 250. Window 252 is formed within the circuit board. The circuit board thus forms spacer 112*z* with substrates 110*z* and 114*z* direct mounted and sealed over the window 252 on either side of the board 250 to form the spectrometer system of the invention. Other components (1–n) are added to the circuit board to meet driver (cir.1), control (cir.2), and i/o (cir.3) and other needs of the system, whose function and operation will be appreciated by a person skilled in the art.

The present invention enables analysis of compounds by high field asymmetric waveform ion mobility techniques in a compact package that can be manufactured using high volume techniques that result in low per chip costs and yet produces results comparable to expensive analytical equipment. The present low parts-count chip design further reduces assembly costs and more importantly lessens the opportunity for variability from chip to chip and system to system, thus improving product reliability. Chips and systems according to the invention are light-weight and yet provide the ability to apply highly effective analytical equipment in the field and in industry beyond the laboratory environment.

PFAIMS devices of the invention are small and compact, with minimized capacitance effects owing to the insulated substrates. In a preferred embodiment, devices in practice of the invention are able to rapidly produce accurate, real-time or near real-time, in-situ, orthogonal data for identification of a wide range of chemical compounds.

It will now be appreciated that the present invention discloses method and apparatus for high field asymmetric waveform ion mobility spectrometry in a planar device configuration. A preferred system includes an input section, an ion filter and detection section and a control section. Ideally ion filtering proceeds in a planar chamber under influence of high field asymmetric periodic signals, with detection integrated into the flow path, for producing accurate, real-time, data for identification of a broad range of chemical compounds.

Efforts on prior art FAIMS devices have focused on the cylindrical, coaxial electrode design. In the present invention, other than a planar external configuration is possible. Reference to a planar device in practice of the present invention at least refers to a generally planar flow path in a generally planar flow channel. Other components and external surfaces may be other than planar.

Various modifications of the specific embodiments set forth above are within the spirit and scope of the present invention. For example, other shapes or configurations of structures, such as electrodes, spacers, and substrates, are within the spirit and scope of the present invention. The specific construction techniques set forth above are not a limitation of the scope of the invention. Other techniques include those disclosed in U.S. Pat. Nos. 6,020,646, and 6,204,090, incorporated herein by reference, having a common inventor and common assignee.

The terms detector, spectrometer and sensor may be used interchangeably for purposes of this disclosure within the spirit and scope of the present invention. The terms drift tube, flow channel and flow path may be used interchangeably and remain within the spirit and scope of the invention. The terms contact pad and bonding pad likewise may be used interchangeably within the spirit of the invention. The terms upper lower inner and outer are relative, are used by way of illustration and not by way of limitation. Furthermore, the examples and embodiments disclosed herein are shown by way of illustration and not by way of limitation. It will be further appreciated that the present invention is operable with gas and liquid samples, even though for convenience the illustrative examples above refer to samples in a gas flow. The scope of these and other embodiments is limited only as set forth in the following claims.

While this invention has been particularly shown and described with references to preferred embodiments thereof, it will be understood by those skilled in the art that various changes in form and details may be made therein without departing from the scope of the invention encompassed by the appended claims.

What is claimed is:

1. Spectrometer system, comprising
a chip assembly formed having at least a pair of substrates separated by a spacer, forming an enclosed flow path, said flow path accommodating a flow of ions representative of a chemical sample,
said assembly having a plurality of electrical contacts, wherein a first said substrate has a filter electrode in communication with a first said contact and wherein a second said substrate has a filter electrode in communication with a second said contact, for forming a FAIMS ion filter enclosed in said flow path,
said substrates and spacer defining a multiple layer package wherein said filter electrodes are separated by an analytical gap in said flow path,
a control source for controlling said filter electrodes, one said substrate and said spacer forming a receiver assembly having electrical contacts, wherein said filter electrodes are in communication with said control source through a combination of said contacts,
one said substrate mounting into said receiver assembly for forming said flow path, and
said flow of ions flowing in said gap and being subjected to a compensated high-low varying asymmetric filter field between said filter electrodes for filtering ion species in said flow of ions for filtering the chemical sample.

2. Spectrometer of claim 1 wherein said chip assembly includes leads for electrical connection to a receiving socket further comprising bonding pads on said substrate mated with bonding pads on said receiver assembly for connection to said leads.

3. Spectrometer of claim 2 wherein said substrates and spacer cooperate to form a hermetically sealed flow channel, said flow channel having an inlet for introduction of a sample flow to said flow path.

4. Spectrometer of claim 2 further comprising a spectrometer chip housing for receipt of said assembly, wherein said substrates have planar exposed working surfaces, said surfaces and said spacer cooperating to form said spectrometer chip housing.

5. Spectrometer of claim 4 wherein said substrates include at least one detector electrode.

6. Spectrometer of claim 4 wherein said spacer is a planar co-fired ceramic and forms the flow channel side walls while acting as a spacer to establish separation between the ion filter electrodes.

7. Spectrometer of claim 4 wherein said spacer and one said substrate are formed as one piece.

8. Spectrometer of claim 4 wherein said spacer and one said substrate are bonded together to form one piece.

9. Spectrometer of claim 1 wherein said substrates and spacer are bonded together using glass frit as a bonding agent.

10. Spectrometer of claim 1 wherein said package includes an inlet tube and an outlet tube coupled to said flow path.

11. Spectrometer of claim 1 further including a pin grid array, wherein said spacer cooperates with one said substrate to provide electrical connection to another said substrate.

12. Spectrometer of claim 11, wherein said package is formed with said substrate and spacer sections and including a pin grid array formed as part of at least one of said sections.

13. Spectrometer of claim 1 wherein said spacer has communication parts to provide electrical connection from one side of said spacer to the other, to enable communication from one said substrate to the other through said spacer.

14. Spectrometer of claim 1 further comprising a socket for mounting on the sample inlet of a mass spectrometer, wherein at least one said substrate supports an electrical connector for connection of said package to said socket.

15. Spectrometer of claim 1 wherein one said substrate has bonding pads and said spacer has metalized sidewalls, wherein said substrate is placed on said spacer with said bonding pads contacting said metalized sidewalls, such that said one substrate is in communication with the other said substrate.

16. Spectrometer system, comprising
a chip assembly including an enclosed flow path for the flow of ions and including a FAIMS ion filter, said enclosed flow path being defined in said ion filter by cooperation of a spacer wall and a substrate mounted to a combined spacer-substrate assembly,
said spacer-substrate assembly defining a substrate having at least one integral spacer wall,
wherein said substrates define said ion filter including a pair of filter electrodes for supplying a compensated asymmetric high-low varying RF filter field for filtering said ion flow in said flow path, wherein said flow path is enclosed by surfaces of said walls and said substrates, and
wherein said enclosed flow path is for flow of an ionized chemical sample in said ion filter, wherein said filter field is generated between said substrates in said ion filter for filtering said ionized sample.

17. Spectrometer of claim 16 further comprising metalization patterns on said substrates forming electrodes, wherein the lower surface of the upper substrate is bonded to the top surface of the sidewalls to form a hermetically sealed flow channel.

18. Spectrometer of claim 17, wherein said spacer walls cooperate with said substrates to define said flow channel, with said spacer walls extending over the edges of said electrodes.

19. Spectrometer system comprising
a microelectronic housing package, including a pair of substrates,
said substrates mated via a spacer and having electrodes on said substrates facing each other over a gap, said spacer cooperating for defining said gap,
said substrates further including an electrical pinout for connection to a socket, said substrates and spacer defining a flow channel within said package,
wherein said spacer further includes sidewalls,
said sidewalls cooperating with said electrodes, and
said electrodes including FAIMS filter electrodes for supplying a compensated high-low varying asymmetric RF field in said gap, wherein ions of interest pass down said flow channel and pass between said filter electrodes and ions of interest are passed through said ion filter during said filtering while other ions in said ion flow are neutralized by contact with said filter electrodes.

20. System of claim 19 wherein one said substrate and said spacer form a substrate with shoulders, and this assembly is mated to a substrate with shoulders, wherein said shoulders cooperate to form a spacer assembly performing a spacing function that defines said gap and a parallel relationship of the electrodes facing each other in the flow channel.

21. System of claim 19 wherein said shoulders extend into flanges, wherein said substrates are joined and said flanges are mated together with bonding agent to form hermetically sealed flow channel.

22. System of claim 21 further comprising lips to provide for accurate alignment, mating and seating of said substrates.

23. System of claim of claim 22 wherein said mated flanges of said mated substrates form wings, further comprising metalization patterns formed on these wings and forming edge connectors with pinouts.

24. System of claim 23, wherein said substrates and spacer form a chip assembly, further comprising an inlet tube and outlet tube on said package.

25. System of claim 19, wherein said substrates and spacer form a chip assembly, said package tapered to define an inlet tube as a longitudinal extension of the chip assembly, extending along a longitudinal axis of said package.

26. System of claim 19, wherein said substrates and spacer form a chip assembly, said package tapered to define an outlet tube as a longitudinal extension of the chip assembly, extending along a longitudinal axis of said package.

27. System of claim 19 wherein said extension forms a coupling mechanism and having an external coupling detail to assist coupling to an external connector.

28. System of claim 19 wherein said spacer is formed with two spacer bars that cooperate with said substrates to define said flow channel.

29. System of claim 19 wherein said spacer includes extensions that define said flow channel and restrict said flow path to be between said electrodes in said gap.

30. System of claim 19 further comprising heater elements and contact pads formed on said substrates, wherein at least said heater elements are encapsulated in a thermally insulating layer.

31. System of claim 19 wherein said spacer and said substrates are ceramic.

32. System of claim 19 wherein said spacer and said substrates form a chip assembly and said package has a mid-section that extends laterally into package wings to form wing areas, further comprising bonding pads on said substrates for forming on-board at least one connector on said.

33. System of claim 32 further comprising an external connector for mating into said on-board at least one connector for connection of said microelectronic housing package to a mass spectrometer.

34. System of claim 19 further comprising a coupling on one said substrate for coupling to an external detector, wherein said substrate includes a detector outlet port formed as an orifice in said substrate.

35. The system of claim 34 further comprising a shielding electrode formed adjacent to said detector electrode to guard same from said RF field.

36. Spectrometer of claim 19 further comprising a circuit board, wherein said spacer is formed by said circuit board.

37. Spectrometer of claim 36 wherein said circuit board defines a window, wherein said substrates are mounted over said window facing each other forming the flow channel, said circuit board performing a spacing function that defines said gap and defines a parallel relationship of the electrodes on the substrates facing each other in the flow channel.

38. System of claim 37 wherein additional components are mounted on said circuit board, including control and i/o circuits.

* * * * *